(12) United States Patent
deLong et al.

(10) Patent No.: US 8,906,962 B2
(45) Date of Patent: *Dec. 9, 2014

(54) COMPOSITIONS AND METHODS FOR TREATING HAIR LOSS USING NON-NATURALLY OCCURRING PROSTAGLANDINS

(71) Applicant: Duke University, Durham, NC (US)

(72) Inventors: Mitchell A. deLong, Chapel Hill, NC (US); John M. McIver, Cincinnati, OH (US); Robert S. Youngquist, Mason, OH (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/034,372

(22) Filed: Sep. 23, 2013

(65) Prior Publication Data

US 2014/0024587 A1 Jan. 23, 2014

Related U.S. Application Data

(60) Continuation of application No. 12/535,513, filed on Aug. 4, 2009, now Pat. No. 8,541,466, which is a continuation of application No. 11/967,423, filed on Dec. 31, 2007, now abandoned, which is a continuation of application No. 11/138,097, filed on May 26, 2005, now Pat. No. 7,388,029, which is a division of application No. 09/774,557, filed on Jan. 31, 2001, now abandoned.

(60) Provisional application No. 60/193,645, filed on Mar. 31, 2000.

(51) Int. Cl.

| | |
|---|---|
| *A61K 31/16* | (2006.01) |
| *A61K 31/21* | (2006.01) |
| *A61K 31/215* | (2006.01) |
| *A61K 31/33* | (2006.01) |
| *A61K 31/38* | (2006.01) |
| *A61K 31/425* | (2006.01) |
| *A61K 31/435* | (2006.01) |
| *A61K 31/54* | (2006.01) |
| *A61K 31/559* | (2006.01) |
| *A61K 8/365* | (2006.01) |
| *A61K 8/37* | (2006.01) |
| *A61K 8/49* | (2006.01) |
| *A61K 31/19* | (2006.01) |
| *A61K 31/381* | (2006.01) |
| *A61K 31/5575* | (2006.01) |
| *A61Q 7/00* | (2006.01) |
| *A61K 45/06* | (2006.01) |

(52) U.S. Cl.
CPC ............... *A61K 31/559* (2013.01); *A61K 8/365* (2013.01); *A61K 8/37* (2013.01); *A61K 8/49* (2013.01); *A61K 8/4986* (2013.01); *A61K 31/19* (2013.01); *A61K 31/381* (2013.01); *A61K 31/5575* (2013.01); *A61Q 7/00* (2013.01); *A61K 45/06* (2013.01)
USPC ........ 514/530; 514/183; 514/222.2; 514/277; 514/367; 514/438; 514/506; 514/529

(58) Field of Classification Search
USPC .............. 514/183, 222.2, 277, 367, 438, 506, 514/529, 530, 613
See application file for complete search history.

(56) References Cited

U.S. PATENT DOCUMENTS

| | | | |
|---|---|---|---|
| 3,382,247 A | 5/1968 | Anthony | |
| 3,435,053 A | 3/1969 | Beal et al. | |
| 3,524,867 A | 8/1970 | Beal et al. | |
| 3,598,858 A | 8/1971 | Bergstrom et al. | |
| 3,636,120 A | 1/1972 | Pike | |
| 3,644,363 A | 2/1972 | Kim | |
| 3,691,216 A | 9/1972 | Bergstrom et al. | |
| 3,706,789 A | 12/1972 | Bergstrom et al. | |
| 3,723,427 A | 3/1973 | Susi | |
| 3,776,938 A | 12/1973 | Bergstrom et al. | |
| 3,776,939 A | 12/1973 | Bergstrom et al. | |
| 3,798,275 A | 3/1974 | Finch et al. | |
| 3,839,409 A | 10/1974 | Bergstrom et al. | |
| 3,852,337 A | 12/1974 | Bergstrom et al. | |
| 3,882,241 A | 5/1975 | Phariss | |
| 3,882,245 A | 5/1975 | DuCharme | |
| 3,896,156 A | 7/1975 | Beal et al. | |
| 3,928,588 A | 12/1975 | Robert | |
| 3,931,282 A | 1/1976 | Muchowski et al. | |
| 3,934,013 A | 1/1976 | Poulsen | |
| 3,966,792 A | 6/1976 | Hayashi et al. | |
| 3,974,213 A | 8/1976 | Hess et al. | |
| 3,984,424 A | 10/1976 | Schaff | |

(Continued)

FOREIGN PATENT DOCUMENTS

| | | |
|---|---|---|
| BE | 746615 | 7/1970 |
| CA | 1339132 | 7/1997 |

(Continued)

OTHER PUBLICATIONS

U.S. Appl. No. 11/174,420, filed Jul. 1, 2005, deLong et al.

(Continued)

*Primary Examiner* — Barbara P Badio

(74) *Attorney, Agent, or Firm* — Michael Best & Friedrich LLP

(57) ABSTRACT

A method for treating hair loss in mammals uses compositions containing prostaglandin F analogs. The compositions can be applied topically to the skin. The compositions can arrest hair loss, reverse hair loss, and promote hair growth.

29 Claims, No Drawings

(56) References Cited

U.S. PATENT DOCUMENTS

| | | |
|---|---|---|
| 3,984,455 A | 10/1976 | Beal et al. |
| 3,985,791 A | 10/1976 | Muchowski et al. |
| 4,004,020 A | 1/1977 | Skuballa et al. |
| 4,005,133 A | 1/1977 | Morozowich |
| 4,011,262 A | 3/1977 | Hess et al. |
| 4,018,812 A | 4/1977 | Hayashi et al. |
| 4,024,179 A | 5/1977 | Bindra et al. |
| 4,051,238 A | 9/1977 | Sokolowski |
| 4,061,671 A | 12/1977 | Beck et al. |
| 4,073,934 A | 2/1978 | Skuballa et al. |
| 4,089,885 A | 5/1978 | Husbands |
| 4,105,854 A | 8/1978 | Gibson |
| 4,116,989 A | 9/1978 | Nelson |
| 4,123,441 A | 10/1978 | Johnson |
| 4,128,577 A | 12/1978 | Nelson |
| 4,128,720 A | 12/1978 | Hayashi et al. |
| 4,139,619 A | 2/1979 | Chidsey, III |
| 4,152,527 A | 5/1979 | Hess et al. |
| 4,154,950 A | 5/1979 | Nelson |
| 4,158,667 A | 6/1979 | Axen |
| 4,171,331 A | 10/1979 | Biddlecom et al. |
| 4,206,151 A | 6/1980 | Grudzinskas |
| 4,217,360 A | 8/1980 | Vorbruggen et al. |
| 4,225,507 A | 9/1980 | Sih |
| 4,225,508 A | 9/1980 | Sih |
| 4,268,522 A | 5/1981 | Eggler et al. |
| 4,284,646 A | 8/1981 | Vorbruggen et al. |
| 4,296,504 A | 10/1981 | Lawson |
| 4,311,707 A | 1/1982 | Birnbaum et al. |
| 4,489,092 A | 12/1984 | Vorbruggen et al. |
| 4,499,293 A | 2/1985 | Johnson et al. |
| 4,543,353 A | 9/1985 | Faustini et al. |
| 4,596,812 A | 6/1986 | Chidsey, III et al. |
| 4,599,353 A | 7/1986 | Bito |
| 4,621,100 A | 11/1986 | Lund et al. |
| 4,704,386 A | 11/1987 | Mueller |
| 4,757,089 A | 7/1988 | Epstein |
| 4,812,457 A | 3/1989 | Narumiya et al. |
| 4,883,819 A | 11/1989 | Bito |
| 4,889,845 A | 12/1989 | Ritter et al. |
| 4,912,235 A | 3/1990 | Cooper et al. |
| 4,952,581 A | 8/1990 | Bito et al. |
| 4,968,812 A | 11/1990 | Wang et al. |
| 5,001,153 A | 3/1991 | Ueno |
| 5,041,439 A | 8/1991 | Kasting et al. |
| 5,063,057 A | 11/1991 | Spellman et al. |
| 5,166,178 A | 11/1992 | Ueno et al. |
| 5,194,429 A | 3/1993 | Ueno |
| 5,212,324 A | 5/1993 | Ueno et al. |
| 5,219,885 A | 6/1993 | Frolich et al. |
| 5,280,018 A | 1/1994 | Ritter et al. |
| 5,288,754 A | 2/1994 | Woodward et al. |
| 5,296,504 A | 3/1994 | Stjernschantz et al. |
| 5,302,617 A | 4/1994 | Ueno |
| 5,312,832 A | 5/1994 | Chan |
| 5,321,128 A | 6/1994 | Stjernschantz et al. |
| 5,332,730 A | 7/1994 | Chan |
| 5,340,813 A | 8/1994 | Klein et al. |
| 5,352,708 A | 10/1994 | Woodward et al. |
| 5,409,911 A | 4/1995 | Tyler et al. |
| 5,422,368 A | 6/1995 | Stjernschantz |
| 5,422,369 A | 6/1995 | Stjernschantz |
| 5,422,371 A | 6/1995 | Liao et al. |
| 5,426,115 A | 6/1995 | Ueno et al. |
| 5,431,881 A | 7/1995 | Palacios |
| 5,458,883 A | 10/1995 | Epstein |
| 5,464,868 A | 11/1995 | Frolich et al. |
| 5,480,900 A | 1/1996 | DeSantis, Jr. et al. |
| 5,500,230 A | 3/1996 | Nathanson |
| 5,508,303 A | 4/1996 | Isogaya et al. |
| 5,510,383 A | 4/1996 | Bishop |
| 5,516,652 A | 5/1996 | Abramovitz et al. |
| 5,567,079 A | 10/1996 | Felder |
| 5,576,315 A | 11/1996 | Hallinan et al. |
| 5,578,618 A | 11/1996 | Stjernschantz et al. |
| 5,578,640 A | 11/1996 | Hanson |
| 5,578,643 A | 11/1996 | Hanson |
| 5,587,391 A | 12/1996 | Burk |
| 5,605,814 A | 2/1997 | Abramovitz et al. |
| 5,605,931 A | 2/1997 | Hanson |
| 5,607,978 A | 3/1997 | Woodward et al. |
| 5,627,208 A | 5/1997 | Stjernschantz et al. |
| 5,641,494 A | 6/1997 | Cauwenbergh |
| 5,658,897 A | 8/1997 | Burk |
| 5,663,203 A | 9/1997 | Ekerdt et al. |
| 5,665,773 A | 9/1997 | Klimko et al. |
| 5,670,506 A | 9/1997 | Leigh et al. |
| 5,681,850 A | 10/1997 | Frolich et al. |
| 5,688,819 A | 11/1997 | Woodward et al. |
| 5,698,733 A | 12/1997 | Hellberg et al. |
| 5,703,108 A | 12/1997 | Cameron et al. |
| 5,716,609 A | 2/1998 | Jain et al. |
| 5,719,140 A | 2/1998 | Chandrakumar et al. |
| 5,741,810 A | 4/1998 | Burk |
| 5,759,789 A | 6/1998 | Abramovitz et al. |
| 5,770,759 A | 6/1998 | Ueno et al. |
| 5,773,472 A | 6/1998 | Stjernschantz |
| 5,792,851 A | 8/1998 | Schuster et al. |
| 5,834,498 A | 11/1998 | Burk |
| 5,840,847 A | 11/1998 | Abramovitz et al. |
| 5,849,791 A | 12/1998 | Stjernschantz et al. |
| 5,863,948 A | 1/1999 | Epstein et al. |
| 5,869,281 A | 2/1999 | Abramovitz et al. |
| 5,877,211 A | 3/1999 | Woodward |
| 5,885,766 A | 3/1999 | Mahe et al. |
| 5,885,974 A | 3/1999 | Danielov |
| 5,889,052 A | 3/1999 | Klimko et al. |
| 5,892,099 A | 4/1999 | Maruyama et al. |
| 5,958,723 A | 9/1999 | Abramovitz et al. |
| 5,972,965 A | 10/1999 | Taniguchi et al. |
| 5,973,002 A | 10/1999 | Frolich et al. |
| 5,977,173 A | 11/1999 | Wos et al. |
| 5,985,597 A | 11/1999 | Ford-Hutchinson et al. |
| 5,990,346 A | 11/1999 | Kataoka et al. |
| 5,994,397 A | 11/1999 | Selliah et al. |
| 6,013,823 A | 1/2000 | Mamarella et al. |
| 6,025,375 A | 2/2000 | Taniguchi et al. |
| 6,025,392 A | 2/2000 | Selliah et al. |
| 6,030,959 A | 2/2000 | Tremont et al. |
| 6,030,999 A | 2/2000 | Stjernschantz et al. |
| 6,031,001 A | 2/2000 | Stjernschantz et al. |
| 6,031,079 A | 2/2000 | Ford-Hutchinson et al. |
| 6,037,364 A | 3/2000 | Burk |
| 6,037,368 A | 3/2000 | Podos et al. |
| 6,043,264 A | 3/2000 | Ohtake et al. |
| 6,048,895 A | 4/2000 | Wos et al. |
| 6,107,338 A | 8/2000 | Wos et al. |
| 6,110,969 A | 8/2000 | Tani et al. |
| 6,121,253 A | 9/2000 | Han et al. |
| 6,124,344 A | 9/2000 | Burk |
| 6,126,957 A | 10/2000 | Epstein |
| 6,160,129 A | 12/2000 | Burk |
| 6,169,111 B1 | 1/2001 | Zinke et al. |
| 6,232,344 B1 | 5/2001 | Feng |
| 6,262,105 B1 | 7/2001 | Johnstone |
| 6,372,730 B1 | 4/2002 | deLong et al. |
| 6,403,649 B1 | 6/2002 | Woodward et al. |
| 6,410,780 B1 | 6/2002 | deLong et al. |
| 6,441,047 B2 | 8/2002 | DeSantis, Jr. |
| 6,444,840 B1 | 9/2002 | deLong et al. |
| 6,451,859 B1 | 9/2002 | deLong et al. |
| 6,534,082 B1 | 3/2003 | Epstein |
| 6,548,535 B2 | 4/2003 | Garcia et al. |
| 6,586,463 B2 | 7/2003 | deLong et al. |
| 6,716,876 B2 | 4/2004 | Burk |
| 6,894,175 B1 | 5/2005 | DeLong et al. |
| 7,045,634 B2 | 5/2006 | Krauss et al. |
| 7,070,768 B2 | 7/2006 | Krauss |
| 7,074,942 B2 | 7/2006 | deLong |
| 7,115,659 B2 | 10/2006 | DeLong |
| 7,157,590 B2 | 1/2007 | Gutman et al. |
| 7,288,029 B1 | 10/2007 | Lyon |
| 7,320,967 B2 | 1/2008 | Michelet et al. |
| 7,388,029 B2 | 6/2008 | deLong et al. |

(56) References Cited

U.S. PATENT DOCUMENTS

| | | |
|---|---|---|
| 7,407,987 B2 | 8/2008 | deLong et al. |
| 7,521,530 B2 | 4/2009 | Peri et al. |
| 7,589,233 B2 | 9/2009 | Chandran |
| 8,541,466 B2 | 9/2013 | deLong et al. |
| 8,618,086 B2 | 12/2013 | deLong et al. |
| 8,623,918 B2 | 1/2014 | deLong et al. |
| 8,722,739 B2 | 5/2014 | deLong et al. |
| 2001/0047025 A1 | 11/2001 | Garcia et al. |
| 2002/0013294 A1 | 1/2002 | deLong et al. |
| 2002/0037914 A1 | 3/2002 | deLong et al. |
| 2002/0044953 A1 | 4/2002 | Michelet et al. |
| 2002/0045659 A1 | 4/2002 | Michelet et al. |
| 2002/0052414 A1 | 5/2002 | Bernard et al. |
| 2002/0146439 A1 | 10/2002 | deLong et al. |
| 2002/0172693 A1 | 11/2002 | deLong et al. |
| 2003/0083381 A1 | 5/2003 | Kumagai et al. |
| 2003/0147823 A1 | 8/2003 | Woodward et al. |
| 2003/0165549 A1 | 9/2003 | Bernard et al. |
| 2003/0191173 A1 | 10/2003 | Garcia et al. |
| 2003/0199590 A1 | 10/2003 | Cagle |
| 2004/0082013 A1 | 4/2004 | Regan |
| 2004/0157151 A1 | 8/2004 | Old et al. |
| 2004/0167190 A1 | 8/2004 | Stjernschantz et al. |
| 2004/0171596 A1 | 9/2004 | Prokai et al. |
| 2005/0058614 A1 | 3/2005 | Krauss |
| 2005/0112075 A1 | 5/2005 | Hwang et al. |
| 2006/0106078 A1 | 5/2006 | Krauss et al. |
| 2006/0121069 A1 | 6/2006 | deLong et al. |
| 2006/0135609 A1 | 6/2006 | Toone et al. |
| 2006/0247214 A1 | 11/2006 | deLong et al. |
| 2007/0004620 A1 | 1/2007 | Jabbour et al. |
| 2007/0161699 A1 | 7/2007 | Epstein et al. |
| 2007/0254920 A1 | 11/2007 | deLong et al. |
| 2007/0282006 A1 | 12/2007 | Woodward et al. |
| 2008/0070988 A1 | 3/2008 | Woodward et al. |
| 2008/0096240 A1 | 4/2008 | Woodward et al. |
| 2008/0103184 A1 | 5/2008 | deLong et al. |
| 2009/0018204 A1 | 1/2009 | Brinkenhoff |
| 2009/0203659 A1 | 8/2009 | Woodward et al. |
| 2014/0031423 A1 | 1/2014 | deLong et al. |
| 2014/0099268 A1 | 4/2014 | deLong et al. |

FOREIGN PATENT DOCUMENTS

| | | |
|---|---|---|
| CA | 2401731 | 10/2001 |
| DE | 1801750 | 7/1969 |
| DE | 1617477 | 1/1970 |
| DE | 2255731 | 5/1973 |
| DE | 2355731 | 5/1974 |
| DE | 2409460 | 8/1974 |
| DE | 2460990 | 12/1974 |
| DE | 2365101 | 7/1975 |
| DE | 24 60 990 | 7/1976 |
| DE | 2605584 | 8/1976 |
| DE | 2605242 | 9/1976 |
| DE | 2517771 | 10/1976 |
| DE | 2737808 | 3/1978 |
| EP | 0170258 | 2/1986 |
| EP | 249194 | 6/1986 |
| EP | 0295092 | 12/1988 |
| EP | 0308135 | 3/1989 |
| EP | 0342003 | 11/1989 |
| EP | 572014 | 1/1993 |
| EP | 639563 | 2/1995 |
| EP | 648488 | 4/1995 |
| EP | 1008588 | 2/1998 |
| EP | 857718 | 8/1998 |
| EP | 1016660 | 9/1998 |
| EP | 911321 | 4/1999 |
| EP | 925787 | 6/1999 |
| EP | 970697 | 9/1999 |
| EP | 947500 | 10/1999 |
| EP | 1267807 | 1/2003 |
| EP | 1267806 | 12/2005 |
| FR | 2108027 | 9/1971 |
| FR | 2182928 | 12/1973 |
| FR | 2239458 | 2/1975 |
| FR | 2314712 | 1/1977 |
| FR | 2730811 | 2/1995 |
| GB | 1236227 | 6/1971 |
| GB | 1251750 | 10/1971 |
| GB | 1285371 | 8/1972 |
| GB | 1285372 | 8/1972 |
| GB | 1324737 | 7/1973 |
| GB | 1409841 | 11/1975 |
| GB | 1456512 | 11/1976 |
| GB | 1456513 | 11/1976 |
| GB | 1456514 | 11/1976 |
| GB | 1456838 | 11/1976 |
| GB | 1542569 | 3/1979 |
| GB | 1545411 | 5/1979 |
| GB | 2025413 | 1/1980 |
| GB | 2048254 | 12/1980 |
| GB | 2330307 | 4/1999 |
| JP | 49-069636 | 7/1974 |
| JP | 49-075558 | 7/1974 |
| JP | 49-093342 | 9/1974 |
| JP | 49-100071 | 9/1974 |
| JP | 49-101356 | 9/1974 |
| JP | 49-102647 | 9/1974 |
| JP | 50-95269 | 7/1975 |
| JP | 50-142539 | 11/1975 |
| JP | 50-157344 | 12/1975 |
| JP | 51-086449 | 7/1976 |
| JP | 52-5744 | 1/1977 |
| JP | 52-012919 | 1/1977 |
| JP | 52-053841 | 4/1977 |
| JP | 53-028160 | 3/1978 |
| JP | 58-029710 | 2/1983 |
| JP | 60-032763 | 2/1985 |
| JP | 61-218510 | 9/1986 |
| JP | 63-211231 | 9/1988 |
| JP | 02 022226 | 1/1990 |
| JP | 03-034934 | 2/1991 |
| JP | 3-83925 | 4/1991 |
| JP | 3-83926 | 4/1991 |
| JP | 4-300833 | 10/1992 |
| JP | 5-331025 | 12/1993 |
| JP | 9-295921 | 11/1997 |
| JP | 10-251225 | 9/1998 |
| JP | 10-287532 | 10/1998 |
| JP | 2003180399 | 7/2003 |
| WO | WO 86/00616 | 1/1986 |
| WO | WO 89/03384 | 4/1989 |
| WO | WO 90/02553 | 3/1990 |
| WO | WO 92/02495 | 2/1992 |
| WO | WO 94/08585 | 4/1994 |
| WO | WO 95/00552 | 1/1995 |
| WO | WO 95/11003 | 4/1995 |
| WO | WO 95/11033 | 4/1995 |
| WO | WO 95/18102 | 7/1995 |
| WO | WO 95/19165 | 7/1995 |
| WO | WO 95/19964 | 7/1995 |
| WO | WO 96/10407 | 4/1996 |
| WO | WO 96/36599 | 11/1996 |
| WO | WO 97/03973 | 2/1997 |
| WO | WO 97/09049 | 3/1997 |
| WO | WO 97/15319 | 5/1997 |
| WO | WO 97/23223 | 7/1997 |
| WO | WO 97/23225 | 7/1997 |
| WO | WO 97/23226 | 7/1997 |
| WO | WO 97/29735 | 8/1997 |
| WO | WO 97/31895 | 9/1997 |
| WO | WO 97/39754 | 10/1997 |
| WO | WO 98/00100 | 1/1998 |
| WO | WO 98/12175 | 3/1998 |
| WO | WO 98/13016 | 4/1998 |
| WO | WO 98/19680 | 5/1998 |
| WO | WO 98/20880 | 5/1998 |
| WO | WO 98/20881 | 5/1998 |
| WO | WO 98/21180 | 5/1998 |
| WO | WO 98/21181 | 5/1998 |
| WO | WO 98/21182 | 5/1998 |

(56) References Cited

FOREIGN PATENT DOCUMENTS

| | | |
|---|---|---|
| WO | WO 98/27976 | 7/1998 |
| WO | WO 98/28264 | 7/1998 |
| WO | WO 98/33497 | 8/1998 |
| WO | WO 98/39293 | 9/1998 |
| WO | WO 98/47515 | 10/1998 |
| WO | WO 98/50024 | 11/1998 |
| WO | WO 98/53809 | 12/1998 |
| WO | WO 98/57930 | 12/1998 |
| WO | WO 98/57942 | 12/1998 |
| WO | WO 98/58911 | 12/1998 |
| WO | WO 99/02165 | 1/1999 |
| WO | WO 99/12550 | 3/1999 |
| WO | WO 99/12551 | 3/1999 |
| WO | WO 99/12552 | 3/1999 |
| WO | WO 99/12553 | 3/1999 |
| WO | WO 99/12554 | 3/1999 |
| WO | WO 99/12555 | 3/1999 |
| WO | WO 99/12556 | 3/1999 |
| WO | WO 99/12557 | 3/1999 |
| WO | WO 99/12558 | 3/1999 |
| WO | WO 99/12559 | 3/1999 |
| WO | WO 99/12560 | 3/1999 |
| WO | WO 99/12561 | 3/1999 |
| WO | WO 99/12563 | 3/1999 |
| WO | WO 99/12895 | 3/1999 |
| WO | WO 99/12896 | 3/1999 |
| WO | WO 99/12897 | 3/1999 |
| WO | WO 99/12898 | 3/1999 |
| WO | WO 99/12899 | 3/1999 |
| WO | WO 99/19300 | 4/1999 |
| WO | WO 99/21562 | 5/1999 |
| WO | WO 99/22731 | 5/1999 |
| WO | WO 99/25357 | 5/1999 |
| WO | WO 99/25358 | 5/1999 |
| WO | WO 99/30675 | 6/1999 |
| WO | WO 99/30718 | 6/1999 |
| WO | WO 99/32441 | 7/1999 |
| WO | WO 99/32640 | 7/1999 |
| WO | WO 99/32641 | 7/1999 |
| WO | WO 99/33794 | 7/1999 |
| WO | WO 99/47497 | 9/1999 |
| WO | WO 99/50241 | 10/1999 |
| WO | WO 99/50242 | 10/1999 |
| WO | WO 99/61029 | 12/1999 |
| WO | WO 99/64621 | 12/1999 |
| WO | WO 99/65303 | 12/1999 |
| WO | WO 99/65527 | 12/1999 |
| WO | WO 00/02450 | 1/2000 |
| WO | WO 00/03736 | 1/2000 |
| WO | WO 00/03980 | 1/2000 |
| WO | WO 00/04898 | 2/2000 |
| WO | WO 00/04899 | 2/2000 |
| WO | WO 00/07627 | 2/2000 |
| WO | WO 00/09557 | 2/2000 |
| WO | WO 00/13664 | 3/2000 |
| WO | WO 00/15608 | 3/2000 |
| WO | WO 00/16760 | 3/2000 |
| WO | WO 00/51971 | 9/2000 |
| WO | WO 00/51979 | 9/2000 |
| WO | WO 00/51980 | 9/2000 |
| WO | WO 00/54810 | 9/2000 |
| WO | WO 01/10873 | 2/2001 |
| WO | WO 01/74307 | 10/2001 |
| WO | WO 01/74313 | 10/2001 |
| WO | WO 01/74314 | 10/2001 |
| WO | WO 01/74315 | 10/2001 |
| WO | WO 02/067901 | 9/2002 |
| WO | WO 02/096868 | 12/2002 |
| WO | WO 03/051822 | 6/2003 |
| WO | WO 03/066008 | 8/2003 |
| WO | WO 03/077910 | 9/2003 |
| WO | WO 2006/047466 | 5/2006 |
| WO | WO 2006/106311 | 10/2006 |
| WO | WO 2007/123818 | 11/2007 |
| WO | WO 2007/127639 | 11/2007 |
| WO | WO 2009/011744 | 1/2009 |
| WO | WO 2010/096123 | 8/2010 |
| WO | WO 2010/108012 | 9/2010 |

OTHER PUBLICATIONS

U.S. Appl. No. 90/009,430, filed Mar. 15, 2009, Woodward.
U.S. Appl. No. 90/009,431, filed Mar. 10, 2009, Johnstone.
Canadian Office Response from Reissue Board in Application No. 2,401,731 dated Nov. 25, 2013.
Chinese Patent Office Action dated Feb. 7, 2014 (12 pages) for Chinese Application No. 201010193487.1, claiming priority to International Application No. PCT/US01/10370 (WO 01/74315) filed Mar. 30, 2011 and U.S. Appl. No. 60/193,645, filed Mar. 31, 2000.
"Agents for Glaucoma," Journal of the American Pharmaceutical Association, New Drugs of 2001, http://www.edscape.com/viewarticle/436631_22 (2007) 4 pages.
"Bimatoprost (ophthalmic)" Medlineplus, Health information online (Jul. 24, 2001) 4 pages, www.nlm.nih.gov/medlineplus/druginfor/uspdi/500295.
"Phase III lumigan—AGN 192024—data presented at American Academy of Ophthalmology," Business Wire (Oct. 23, 2000) 3 pages.
Abramovitz, M. et al., "Cloning and expression of a cDNA for the human prostanoid FP receptor," J. Biol. Chem. (1994) 269:2632-2636.
Abramovitz, M. et al., "The utilization of recombinant prostanoid receptors to determine the affinities and selectivities of prostaglandins and related analogs," Biochimica et Biophysica Acta (2000) 1483(2):285-293.
ADIS, Adisinsight: ZD-6416, AstraZeneca (United Kingdom) Mar. 27, 2000, 1 page.
AGN-192024, Pharmaprojects, HB4 S1G (2006).
Allergan Clinical Study Report, Study No. 192024-008, "A multicenter, double-masked, unevenly randomized, parallel, active-controlled three-month study (with treatment extended to one year) of the safety and efficacy of once-daily or twice-daily administered AGN 192024 0.03% ophthalmic solution compared with twice-daily administered timolol 0.5% ophthalmic solution in subjects with glaucoma or ocular hypertension," (Aug. 1, 2000), vol. 1 of 32, 356 pages.
Allergan Clinical Study Report, Study No. 192024-009, "A multicenter, double-masked, randomized, parallel, 3-month study (with treatment extended to 1 year) of the safety and efficacy of AGN 192024 0.03% ophthalmic solution administered once-daily or twice-daily compared with Timolol 0.5% ophthalmic solution administered twice-daily in subjects with glaucoma or ocular hypertension" (Aug. 2, 2000) 34 pages.
Allergan Clinical Study Report, Study No. 192024-010-01, "A multicenter, investigator-masked, randomized, parallel study of the safety and efficacy of AGN 192024 0.03% ophthalmic solution compared with Latanoprost 0.005% ophthalmic solution administered once-daily in subjects with glaucoma or ocular hypertension" (May 9, 2001) 38 pages.
Allergan Press Release, "Phase III Lumigan? (AGN 192024) data presented at American Academy of Ophthalmology," Mar. 1, 2000, 5 pages.
Alm et al., "Effects on intraocular pressure and side effects of 0.005% latanoprost applied once daily, evening or morning," Ophthalmology (1995) 102(12):1743-1752.
Alm, A. et al., "Phase III latanoprost studies in Scandanavia, the United Kingdom and the United States," Surv. Ophthalmol. (1997) 41(Suppl 2):S105-S110.
Alm, A. et al., "Uveoscleral outflow—a review," Exp. Eye Res. (2009) 88(4):760-768, Epub Jan. 3, 2009.
Alm, A., "The potential of prostaglandin derivates in glaucoma therapy; prostaglandins and derivates," Curr. Opin. Opthalmol. (1993) 4(11):44-50.
Al-Sereiti, M.R., et al., "Pharmacology of Rosemary (*Rosmarinus officinalis* Linn.) and Its Therapeutic Potentials," Indian Journal of Experimental Biology, vol. 37, Feb. 1999, pp. 124-130.
Anonymous, "Alprostadil (nexmed):Alprox-TD, Befar, Femprox, Prostaglandin E1 (nexmed)," Drugs R&D (1999) 2(6):413-414.

(56) References Cited

OTHER PUBLICATIONS

Audoly, L.P. et al., "Identification of specific EP receptors responsible for the hemodynamic effects of PGE2," Am. J. Physiol. (1999) 46(3):H924-930.
Badawy, S.I. et al., "Salt selection for pharmaceutical compounds," Adeyeye, J. editor, Preformulation in Solid Dosage Form Development, Informa Healthcare (2008) Chapter 2.3, 63-80.
Bartman, W., et al., "Leutolytic Prostaglandins Synthesis and Biological Activity", Prostaglandins, vol. 17, No. 2, pp. 301-311, 1979.
Bastin, R.J. et al., "Salt selection and optimisation procedures for pharmaceutical new chemical entities," Organic Process R&D (2000) 4(5):427-435.
Bean, G.W., "Commercially available prostaglandin analogs for the reduction of intraocular pressure: similarities and differences," Survey of Ophthalmology (2008) 53(1):569-84.
Berge, S.M. et al., "Pharmaceutical salts," J. Pharm. Sci. (1997) 66(1):1-19.
Berglund, B.A. et al., "Investigation of structural analogs of prostaglandin amides for binding to and activation of CB1 and CB2 cannabinoid receptors in rat brain and human tonsils," Adv. Exp. Med. Biol. (1999) 469:527-533.
Bialer, M. et al., "Pharmacokinetics of valpromide after oral administration of a solution and a tablet to healthy volunteers," Eur. J. Clin. Pharma. (1984) 27:501-503.
Bito, L., "A new approach to the medical management of glaucoma, from the bench to the clinic, and beyond," The Proctor Lecture (2001) 42(6):1126-1133.
Bito, L.Z. et al., "Long-term maintenance of reduced intraocular pressure by daily or twice daily topical application of psotaglandins to cat or rhesus monkey eyes," Invest. Ophthalmol. Vis. Sci. (1983) 24(3):312-319.
Bito, L.Z. et al., "The ocular pharma-cokinetics of eicosanoids and their derivatives," Exp. Eye Res. (1987) 44:217-226.
Bockaert, J. et al., "Molecular tinkering of G protein-coupled receptors: an evolutionary success," Eur. Molecular Biol. Org. (1999) 18:1723-1729.
Brandt, J.D. et al., "Comparison of once-or twice-daily bimatoprost with twice-daily timolol in pateints with elevated IPO. A three month clinical tril," Ophthalmology (2001) 108(6):1023-1031.
Brown, M.M. et al., "Improper topical self-administration of ocular medication among patients with glaucoma," Can. J. Ophthal. (1984) 19(1):2-5.
Brubaker, R.F. et al., "Effects of AGN 192024, a new ocular hypotensive agent, on aqueous dynamics," Am. J. Opthal. (2001) 131(1):19-24.
Buck, F. et al., "Characterization of N- and C-terminal deletion mutants of the rat serotonin HT2 receptor in *Xenopus laevis* oocytes," Biochem. Biophys. Res. Comm. (1991) 178, 1421-1428.
Bundy, G. L., and Lincoln, F. H., "Synthesis of 17-Phenyl-18, 19, 20-Trinoprostaglandins 1. The PG, Series," Prostaglandins, vol. 9, No. 1, (Jan. 1975), pp. 1-4.
Cadet, P. et al., "Molecular identification and functional expression of mu3, a novel alternatively apliced variant of the human mu opiate receptor gene," J. Immunol. (2003) 170(10):5118-5123.
Camras, C.B. et al. "Bimatoprost, the prodrug of a prostaglandin analogue," Br. J. Ophthalmol. (2008) 92:862-863.
Camras, C.B. et al., "Latanoprost, a prostaglandin analog, for glaucoma therapy," Ophthalmology (1996) 103(11):1916-1924.
Camras, C.B. et al., "Multiple dosing of prostaglandin F2alpha or epinephrine on cynomolgus monkey eyes," Invest. Ophthalmol. Vis. Sci. (1987) 28(3):463-469.
Camras, C.B. et al., "Multiple dosing of prostaglandin F2alpha or epinephrine on cynomolgus monkey eyes," Invest. Ophthalmol. Vis. Sci. (1987) 28(6):921-926.
Camras, C.B. et al., "Multiple dosing of prostaglandin F2alpha or epinephrine on cynomolgus monkey eyes," Invest. Ophthalmol. Vis. Sci. (1988) 29(9):1428-1436.
Camras, C.B. et al., "Reduction of intraocular pressure by prostaglandins applied topically to the eyes of conscious rabbits," Invest. Ophthal & Vis. Sci. (1977) 16, 1125-1134.
Camras, C.B. et al., "Reduction of intraocular pressure in normal and glaucomatous primate (*Aotus trivirgatus*) eyes by topically applied prostaglandin F2alpha," Curr. Eye Res. (1981) 1(4):205-209.
Camras, C.B., "Comparison of latanoprost and timolol in patients with ocular hypertension and glaucoma," Ophthalmology (1996) 103(1):138-147.
Camras, C.B., "Detection of the free acid of bimatoprost in aqueous humor samples from human eyes treated with bimatoprost before cataract surgery," American Academy of Ophthalmology (2004) 2193-2198.
Cantor, L.B. et al., "Levels of bimatoprost acid in the aqueous humour after bimatoprost treatment of patients with cataract," Br. J. Ophthalmol. (2007) 91:629-632.
Cantor, L.B., "Reply—bimatoprost, the prodrug of a prostaglandin analogue," Br. J. Ophthalmol. (2008) 92:863-864.
CAS RN 155206-00-1 (May 20, 1994).
Cayatte, A.J. et al., "The thromboxane A2 receptor antagonist S18886 decreases atheroschlerotic lesions and serum intracellular adhesion molecule-1 in the Apo E knockout mouse," Circulation (1998) 96:115.
Center for Drug Evaluation and Research, "Medical Officer's Review of NDA, Application No. 21-275," Mar. 14, 2001; 120-day safety update Jan. 23, 2001; Mar. 2, 2001; Sep. 18, 2000, 63 pages.
Chen, J. et al., "AGN 191129: a neutral prostaglandin F-2 alpha (PGF2a) analog that lacks the mitogenic and uterotonic effects typical of FP receptor agonists," IOVS (1999) 40:3562-B420, p. S675.
Chen, J. et al., "Replacement of the carboxylic acid group of prostaglandin F2alpha (PGH2alpha) with certain non-ionizable substituents results in pharmacologically unique ocular hypotensive agents," 11th International Conference Advances Prostaglandins and Leuotremic Res. Basic Sci. & New Clinical Applications—Abstract book (2000) 48.
Chen, J. et al., "Structure-based dissociation of a type I polyketide synthase module," Chem. Biol. (2007) 14, 784-792.
Chen, J. et al., "Studies on the pharmacology of prostamide F2alpha a naturally occurring substance," Br. J. Pharm. (2001) 133, 63p.
Chen, J. et al., "Studies using isolated uterine and other preparations show Bimatoprost and prostanoid FP agents have different activity profiles," Br. J. Pharm. (2005) 144, 493-501.
Chowdhury, U.R. et al., "Proteome analysis of human aqueous humor," Biochem. Mol. Biol. (2010) 51(10):4921-4931.
Chrai, S.S. et al., "Drop size and initial dosing frequency problems of topically applied ophthalmic drugs," J. Pharm. Sci. (1974) 63:333-338.
Chyun, Y.S. et al., "Stimulation of bone formation by prostaglandin E2," Prostaglandins (1984) 27:97-103.
Ciruela, F. et al., "Immunologicla identification of A1 adenosine receptors in brain cortex," J. Neurosci. Res. (1995) 42, 818-828.
Clissold, D., "The potential for prostaglandin pharmaceuticals," Spec. Publ.-R. Soc. Chem. (1999) 244:115-129.
Coleman, R.A. et al., "Prostanoids and their receptors," Comprehensive Med. Chem., Membranes and Receptors (1990) 3:643-714.
Coleman, R.A. et al., "VIII. International Union of Pharmacology. Classification of prostanoid receptors: properties, distribution, and structure of the receptors and their subtypes," Pharmacol. Rev. (1994) 46(2):205-229.
Collins, P.W. et al., "Synthesis of therapeutically useful prostaglandin and prostacyclin analogs," Chem. Rev. (1993) 93:1533-1564.
Colombe, L. et al., "Prostanoid receptors in anagen human hair follicles," Exp. Derm. (2007) 17:63-72.
Corsini, A. et al., "(5Z)-Carbacyclin discriminates between prostacyclin receptors coupled to adenylate cyclase in vascular smooth muscle and platelets," Br. J. Pharmacol. (1987) 90:255-261.
Crowston, J.G. et al., "Effect of bimatoprost on intraocular pressure in prostaglandin FP receptor knockout mice," Invest. Ophthal. Vis. Sci. (2005) 46:4571-4577.
Cummings, J. et al., "Enzymology of mitomycin C metabolic activation in tumour tissue: implications for enzyme-directed bioreductive drug development," Biochem. Pharmacol. (1998) 56:405-414.
Cyr, C. et al., "Prolonged desensitization of the human endothelin a receptor in *Xenopus oocytes*," J. Biol. Chem. (1993) 268, 26071-26074.

(56) References Cited

OTHER PUBLICATIONS

Darnell, J. et al., "Cell-to-cell signaling: hormones and receptors," Mol. Cell. Biol. (1990) 738-743.

Davies, S.S., "Hydrolysis of bimatoprost (lumigan) to its free acid by ocular tissue in vitro," J. Ocular Pharm. Thera. (2003) 19(1):45-54.

Dean, T.R. et al., "Improvement of optic nerve head blood flow after one-week topical treatment with travoprost (AL-06221) in the rabbit," IOVS (1999) 40(4):2688-B563, p. S509.

Del Toro, F. et al., "Characterization of prostaglandin E2 receptors and their role in 24,25-(OH)2D2-mediated effects on resting zone chondrocytes," J. Cell Physiol. (2000) 182(2):196-208.

Delong, M.A., "Prostaglandin receptor ligands: recent patent activity," Drugs (2000) 3(9):1039-1052.

Depperman, W.J., Jr., "Up-to-date scalp tonic," New Eng. J. Med. (1970) 283(2):1115.

Dirks, M. et al., "Efficacy and safety of the ocular hyotensive lipid 192024 in patients with elevated IOP: a 30-day comparison with Latanoprost," Invest. Opthal. Visual Sci. (2000) 41(4):2737-B983.

Draelos, Z.D., "Special considerations in eye cosmetics," Clinics in Dermatology (2001) 19, 424-430.

DuBiner, H. et al., "Efficacy and safety of bimatoprost in patients with elevated intraocular pressure: a 30-day comparison with latanoprost," Survey of Ophthal. (2001) 45(S4):S353-S360.

Easthope, S.E. et al., "Topical bimatoprost: a review of its use in open-angle glaucoma and ocular hypertension," Drugs Aging (2002) 19(3):231-248.

Eisenberg, D.L. et al., "A preliminary risk-benefit assessment of latanoprost and unoprostone in open-angle glaucoma and ocular hypertension," Drug Safety (1999) 20(6):505-514.

Ellis, C. K., et al., "Metabolism of Prostaglandin D2 in the Monkey," J. of Biological Chem., vol. 254, No. 10, pp. 4152-4163 (1979).

Ernst, O.P. et al., "Mutation of the fourth cytoplasmic loop of Rhodopsin affects binding of transducin and peptides derived from the carboxyl-terminal sequences of transducin α and γ subunits," J. Biol. Chem. (2000) 275, 1937-1943.

Fagot, D. et al., "Mitogenic signaling by prostaglandins in chemically transformed mouse fibroblasts: comparison with phorbol esters and insulin," Endocrinology (1993) 132(4):1729-1734.

Fall, P. M., et al "Inhibition of Collagen Synthesis by Prostaglandins in the Immortalized Rat Osteoblastic Cell Line Pyla: Structure-Activity Relations and Signal Transduction Mechanisms," J. Bone Miner. Res. (1994) 9:1935-1943 (abstract).

Fan, T. et al., "A role for the distal carboxyl tails in generating the novel pharmacology and G protein activation profile of μand δ opioid receptor hetero-oligomers," J. biol. Chem. (2005) 280, 38478-38488.

Faulkner, R., "Aqueous humor concentrations of bimatoprost free acid, bimatoprost and travoprost free acid in cataract surgical patients administered multiple topical ocular doses of Lumigan® or Travatan®," J. Ocular Pharm. Thera. (2010) 26(2):147-156.

FDA Consumer Magazine, "New Drugs for Glaucoma" (May-Jun. 2001) 35(3), 4.

FDA Consumer, "New drugs for glaucoma (Lumigan and Travatan)" May 2001, available at http://www.highbeam.com/doc/1G1-75608860.html/print.

FDA Eye Cosmetic Safety at http://www.fda.gov/cosmetics/productandingredientsafety/productinformation/ucm137241.htm, (Aug. 1, 2001) 2 pages.

FDA Label for Approved NDA 22-184—Lumigan 0.01% and Lumigan 0.03% (Aug. 31, 2010) 5 pages.

FDA Press Release, "FDA News" of Mar. 16, 2001 entitled "FDA approves two new intraocular pressure lowering drugs for the management of glaucoma," 2 pages.

Fiscella, R.G., "Peek into the drug pipeline," Review of Optometery Online, Jan. 15, 2001, pp. 1-5.

Fitzpatrick, F. A., "Separation of Prostaglandins and Thromboxanes by Gas Chromatography with Glass Capillary Columns," Analytical Chemistry, vol. 50, No. 1, pp. 47-52, 1978.

Fletcher, D.G. et al., "Synthesis and biological acivity of 16, 17-configurationally-ridig-17-aryl 18, 19, 20-trinorprostaglandins," Prostaglandins (1976) 12(4):493-500.

Flisiak, R. et al., "Effect of misoprostol on the course of viral hepatitis B," Hepato-Gastroenterology (1997) 44(17):1419-1425.

Fowler, C.J., "The contribution of cydooxygenase-2 to endocannabinoid metabolism and action," Br. J. Pharmacol. (2007) 152:594-601.

Frenkel, R.E. et al., "Evaluation of circadian control of intraocular pressure after a single drop of bimatoprost 0.03% or travoprost 0.004%," Curr. Med. Res. Opin. (2008) 24(4):919-923, epub Feb. 8, 2008.

Funk, C.D. et al., "Cloning and expression of a cDNA for the human prostaglandin E receptor EP1 subtype," J. Biol. Chem. (1993) 268:26767-26772.

Gandolfi, S.A. et al., "Effect of Bimatoprost on patients with primary open-angle glaucoma or ocular hypertension who are nonresponders to Latanoprost," Ophthal. (2003) 110:609-613.

Gandolfini, S. et al., "Three-month comparison of bimatoprost and latanoprost in patients with glaucoma and ocular hypertension," Adv. In Therapy (2001) 18(3):110-121.

Garadi, R. et al., "Travoprost: a new once-daily dosed prostaglandin for the reduction of elevated intraocular pressure," IOVS (1999) 40(4):4378-B181, p. S831.

Garza, L.A. et al., "Prostaglandin 02 inhibits hair growth and is elevated in bald scalp of men with androgenetic alopecia," Sci. Transl. Med. (2012) 4:1-11.

Gaynes, B.I. et al., "Topical ophthalmic NSAIDs: a discussion with focus on Nepfenac ophthalmic suspension," Clin. Ophthal. (2008) 2, 355-368.

Geng, L. et al., "Topical or systemic 16,16 dm-prostaglandin E2 or WR-2721 (WR-1065) protects mice and alopecia after fractionated irradiation," Int. J. Radiat. Biol. (1992) 61(4):533-537.

Geng, L., Malkinson, F.D., Hanson, W.R., "Misoprostol, A PGE1 Analog that is Radioprotective for Murine Intestine and Hair, Induces Widely Different Cytokinetic Changes in these Tissues," Journal of Investigative Dermatology, 1996, vol. 106, No. 4, p. 858.

Gerth, J. et al., "Drug makers reap profits on tax-backed research," New York Times, Apr. 23, 2000, 10 pages.

Giuffre, G., "The effects of prostaglandin F2alpha in the human eye," Graefe's Arch. Clin. Exp. Ophthalmol. (1985) 222:139-141.

Glaucoma Foundation, Treatment update, New drug approved by Food and Drug Administration. Unoprostone isopropyl ophthalmic solution, 15%, Eye to Eye Newsletter, (Fall 2000) 11, p. 10.

Griffin, B.W. et al., "AL-8810: a novel prostaglandin F2a analog with selective antagonist effects at the prostaglandin F2a (FP) receptor," J. Pharmacol. Exp. Ther. (1999) 290(3):1278-1284.

Gupta, R. et al., "Evaluating eye drop instillation technique in glaucoma patients," J. Glaucoma (2012) 21:189-192.

Haj-Yehia, A. et al., "Structure-pharmacokinetic rleationships in a series of short fatty acid amides that possess anticonvulsant activity," J. Pharm. Sci. (1990) 79, 719-24.

Hall, A., Smith, W. H. T., "Clinprost Teijin," Current Opinion in Cardiovascular, Pulmonary & Renal Investigation Drugs, 1999, 1(5), pp. 605-610.

Hallinan, E.A. et al., "Aminoacetyl moiety as a potential surrogate for diacylhydrazine group of SC-51089, a potent PGE2 antagonist, and its analogs," J. Med. Chem. (1996) 39:609-613.

Hanson, W.R. et al., "16,16 dm prostaglandin 2 protects from acute radiation-induced alopecia in mice," Clin. Res. (1988) 36(6):906a.

Hanson, W.R. et al., "Misoprostol, a PGE1 Analog that is Radioprotective for Murine Intestine and Hair, Induces Widely Different Cytokinetic Changes in these Tissues," J. Invest. Dermatol. (1996) 106(4):858.

Hanson, W.R. et al., "Subcutaneous or topical administration of 16,16 dimethyl prostaglandin E2 protects from radiation-induced alopecia in mice," Int. J. Radiat. Oncol. Biol. Phys. (1992) 23(2):333-337.

Hartke, J.R. et al., "Prostanoid FP agonists build bone in the ovariectomized rat," J. Bone Min. Res. (1999) 14(T326):S207.

Hayashi, M. et al., "Prostaglandin Analogues Possessing Antinidatory Effects. 1. Modification of the ω Chain," J. Med. Chem. (1980) 23(5):519-524.

Hecker, M. et al., "Studies on the interaction of minoxidil with prostacyclin synthase in-vitro," Biochem. Pharmacol. (1988) 37(17):3363-3365.

(56) References Cited

OTHER PUBLICATIONS

Hellberg, M.R. et al., "Identification and characteristics of the ocular hypotensive efficacy of Travoprost, a potent and selective prostaglandin receptor agonist and AL-6598, a DP prostaglandin receptor agonist," Surv. Ophthal. (2002) 47:S13-33.
Hellberg, M.R. et al., "The hydrolysis of the prostaglandin analog prodrug bimatoprost to 17-phenyltrinor PGF2a by human and rabbit ocular tissue," J. Ocular Pharmacol. Ther. (2003) 19:97-103.
Higginbotham, E.J. et al., "One-year randomized study comparing bimatoprost and timololin in glaucoma and ocular hypertension," Arch. Ophthal. (2002) 120(10):1286-1293.
Hirata, T. et al., "Prostanoid receptors," Chem. Rev. (2011) 111(10):6209-6230.
Ho, N.F.H., "Physical model approach to the design of drugs with improved intestinal absorption," in Design of Biopharmaceutical Properties Through Prodrugs and Analogs, Roche ed, (1977) Chapter 8, pp. 136, 177-182.
Hoen, P.A.C. et al., "mRNA degradation controls differentiation state-dependent differences in transcript and splice variant abundance," Nuc. Acids Res. (2010) 39, 556-566.
Honohan, T. et al., "Duration of the activity of the acid, methyl ester and amide of an orally active platelet aggregation inhibitory prostanoid in the rat," Prost. (1980) 19(1):139-153.
Honohan, T. et al., "Hydrolysis of an orally active platelet inhibitory prostanoid amide in the plasma of several species," Prostaglandins (1980) 19(1):123-138.
Hori, H. et al., "The thickness of human scalp: normal and bald," J. Invest. Derm. (1972) 58, 396-399.
Hosoda, M. et al., "Do glaucoma patients use eye drops correctly?" J. Glaucoma (1995) 4:202-206.
Houssay, A.B. et al., "Effects of prostaglandins upon hair growth in mice," Acta Physiol. Let. Am. (1976) 266(3):186-191.
Huang, A. et al., "Different modes of inhibition of increase in cytosolic calcium and aggregation of rabbit platelets by two thromboxane A2 antagonists," Asia Pacific Journal of Pharmacology (1994) 9:163-171.
Hulan, H.W. et al., "The development of dermal lesions and alopecia in male rats fed grapeseed oil," Can. J. Physiol. Pharmacol. (1976) 54(1):1-6.
Hulan, H.W. et al., "The effect of long-chain monoenes on prostaglandin E2 synthesis by rat skin," Lipids (1977) 12(7):604-609.
Hwang, K. et al., "Thickness of Korean upper eyelid skin at different levels," J. Craniofacial Surgery (2006) 17, 54-56.
Ichhpujani, P. et al., "Comparison of human ocular distribution of dimatoprost and latanoprost," J. Ocular Pharm. Thera. (2012) 28:134-145.
Ichikawa, E.A. et al., "Molecular aspects of the structures and functions of the prostaglandin E receptors," J. Lipid Mediators Cell Signaling (1996) 14:83-87.
Inoue, H., "Thromboxane A2 receptor antagonists," Farumashia (1996) 32(1):1221-1225 (no English translation available).
Jakobsson, P.J. et al., "Membrane-associated proteins in eicosanoid and glutathione metabolism (MAPEG)—a widespread protein superfamily," Am J. Resp. Crit. Care Med. (2000) 161:S20-S24.
Jimenez De Asua, L. et al., "The stimulation of the initiation of DNA synthesis and cell division in Swiss mouse 3T3 cells by prostaglandin F2alpha requires specific functional groups in the molecule," J. Biol. Chem. (1983) 256(14):8774-8780.
Jimenez, J.J. et al., "Stimulated monocyte-conditioned media protect for cytosine arabinoside-induced alopecia in rat," Clin. Res. (1990) 38(4):973a.
Johnstone, M.A. et al., "Prostaglandin-induced hair growth," Surv. Ophth. (2002) 47(1):S185-202.
Johnstone, M.A., "Hypertrichosis and increased pigmentation of eyelashes and adjacent hair in the region of the ipsilateral eyelids of patients treated with unilateral topical latanoprost," Amer. J. Ophthal. (1997) 544-547.
Johnstone, M.A., Brief latanoprost Rx induces hypertrichosis, IOVS (1998) 39(4):1180-B61.

Joost, P. et al., "Phylogenetic analysis of 277 human G-protein-coupled receptors as a tool for the prediction of orphan receptor ligands," Genome Biol. (2002) 3(11):0063.1-16.
Jordan, B.A. et al., "G-protein coupled receptor heterodimerization modulates receptor function," Nature (1999) 399(6737):697-700.
Karim, S.M.M. et al., "Prostaglandins and human respiratory tract smooth muscle: structure activity relationship," Adv. Prostaglandin Thromboxane Res. (1980) 7:969-980.
Kass, M.A. et al., "Madarosis in chronic epinephrine therapy," Arch. Ophthal. (1972) 88:429-431.
Kaufman, P.L., "Effects of intracamerally infused prostaglandins on outflow facility in cynomolgus monkey eyes with intact or retrodisplaced ciliary muscle," Exp. Eye Res. (1986) 43:819-827.
Kaupmann, K. et al., "GABA(B)-receptor subtypes assemble into functional heteromeric complexes," Nature (1998) 396, 683-687.
Ke, T-L et al., "Nepafanac, a unique nonsteroidal prodrug with potential utility in the treatment of trauma-induced ocular inflammation," Inflammation (2000) 24, 371-384.
Kelly, C.R et al., "Real-time intracellular Ca2+ mobilization by travoprost acid, bimatoprost, unoprostone an dother analogs via endogenous mouse, rat and cloned human Fp prostaglandin receptors," J. Pharm. Exp. Ther. (2003) 304(1):238-245.
Kende, et, al., "Prostaglandin Phosphonic Acids Through Homolytic Halodecarboxylation of Prostaglandins Flα and F2α," Tetrahedron Letters, vol. 40, pp. 8189-8192 (1999).
Kerstetter, J.R. et al., "Prostaglandin F2 alpha- 1 -isopropylester lowers intraocular pressure without decreasing aqueous humor flow," Am. J. Ophthalmology (1988) 105:30-34.
Kiriyama, M. et al., "Ligand binding specificities of the eight types and subtypes of the mouse prostanoid receptors expressed in Chinese hamster ovary cells," Br. J. Pharm. (1997) 122:217-224.
Kluender, H.C. et al., "The Synthesis of Diethylphosphonoprostaglandin Analogs" Prostaglandins and Medicine (1979) 2(6):441-444.
Kobilka, B.K. et al., "Chimeric alpha2-, beta2-adrenergic receptors: delineration of domains in volved in effector coupling and ligand binding specificity," Science (1988) 240:1310-1316.
Kolker, A.E., Discussion, Ophthalmology (2001) 108(6):1032.
Krauss, A.H.P. et al., "Evidence for human thromboxane receptor heterogeneity using a novel series of 9,11-cyclic carbonate derivatives of prostaglandin-F2-alpha," Br. J. Pharmacol. (1996) 117(6):1171-1180.
Kvedar, J.C. et al., "Topical minoxidil in the treatment of male pattern alopecia," Pharmacotherapy (1987) 7(6):191-197.
La Du, B.N., "Pharmacogenetics: defective enzymes in relation to reactions to drugs," Ann. Rev. Med. (1972) 23, 453-468.
Lachgar, S. et al., "Effect of VEGF and minoxidil on the production of arachidonic acid metabolites by cultured hair, dermal papilla cells," Eur. J. Dermatol. (1996) 6(5):365-368.
Lachgar, S. et al., "Hair dermal papilla cell metabolism is influenced by minoxidil," Fundam. Clin. Pharmacol. (1997) 11(2):178.
Lachgar, S. et al., "Modulation by minoxidil and VEGF of the production of inflammatory mediators by hair follicle dermal papilla cells," J. Invest. Derm. (1995) 104(1):161.
Lardy, C. et al., "Antiaggregant and antivasospastic properties of the new thromboxane A2 receptor antagonist sodium 4-[[1-[[[(4-chlorophenyl) sulfonyl]amino] methyl] cyclopentyl] methyl] benzeneacetate," Arzneim.-Forsch./Drug Res. (1994) 44(11):1196-1202.
Latisse (Bimatoprost Ophthalmic Solution) 0.03% Label (2001).
Lederer, C.M. et al., "Drop size of commercial glaucoma medications," Am. J. Ophthal. (1986) 101:691-694.
Lee, P.-Y. et al., "The effect of prostaglandin F2alpha on intraocular pressure in mormotensive human subjects," Invest. Ophthalmol. Vis. Sci. (1988) 29(10):1474-1477.
Lee, V.H.L. et al., "Improved ocular drugs delivery with prodrugs," in Prodrugs: Topical and Ocular Drug Delivery, Marcel Dekker, New York (1992) 221-297.
Lee, V.H.L. et al., "Review: topical ocular drug delivery: recent developments and future challenges," J. Ocular Pharm. (1986) 2:67-108.

(56) References Cited

OTHER PUBLICATIONS

Letter from Bernadette Attinger at Sandoz Inc. To the General Counsels at Allergan, Inc. and Duke University regarding Notice of Certification Under 21 USC Sect. 355(j)(2)(b) of Federal Food, Drug and Cosmetic Act) and 21 CFR Sect. 314.95, regarding Sandoz Inc.'s ANDA 202719, dated Mar. 3, 2011 (21 pages).
Letter from Bernice Tao at Apotex, Inc. to the General Counsels at Allergan, Inc. and Duke University regarding "Apotex Bimatoprost Topical Solution 0.03% Paragraph IV Certification—U.S. Patent Nos. 7,351,404 and 7,388,029" (Jul. 26, 2010) 49 pages.
Letter from Joanne Curri at Hi-Tech Pharmacal Co., Inc. to Duke University regarding Abbreviated New Drug Application in Accordance with Section 505(j)(2)(b) of the Food, Drug and Cosmetic Act dated Jun. 29, 2011 (22 pages)
Letter from Joyce Delgaudio at Watson Laboratories, Inc. to the General Counsels at Allergan, Inc. and Duke University regarding Notification of Certification for U.S. Patent Nos. 7,351,404; 7,388,029; 8,038,988; and 8,101,161 Pursuant to §505(j)(2)(B)(iv) of the Federal Food, Drug, and Cosmetic Act dated Feb. 28, 2012 (42 pages), redacted.
Liang, Y. et all., "Identification and pharmacological characterization of the prostaglandin FP receptor and FP receptor varian complexes," Br. J. Pharmacol. (2008) 154:1079-1093.
Liljebris, C., Selen, G., Resul, B. Stjernschantz, J., and Hacksell, U., "Derivatives of 17-Phenyl-18, 19, 20 Trinorprostaglan F2a Isopropyl Ester: Potential Antiglaucoma Agents," Journal of Medicinal Chemistry, vol. 38, No. 2, (1995), pp. 289-304.
Ling, G. et al., "16,16 dm prostaglandin E2 protects mice from fractionated radiation-induced alopecia," Clin. Res. (1990) 38(3):858a.
Lumigan (Bimatoprost Opthalmic Solution) 0.03% Package Insert, Mar. 2001.
Lumigan 6-month phase 3 data presented at American Glaucoma Society Meeting, Mar. 2, 2001, Business Wire, 3 pages.
Lundy, M.W. et al., "Restoration of cancellous architecture and increased bone strength in aged osteopenic rats treated with fluprostenol, "J. Bone Min. Res. (1999) 1(4)SA368:S401.
Maddox, Y.T. et al., "Amide and L-amino derivatives of F prostaglandins as prostaglandin antagonists," Nature (1978) 273:549-552.
Maggio, R. et al., "Reconstitution of functional muscarinic receptors by co-expression of amino- and carboxyl-terminal receptor fragments," Fed. Eur. Biochem. Soc. Left. (1993) 319, 195-200.
Malkinson, F.D. et al., "Prostaglandins protect against murine hair injury produced by ionizing radiation or doxorubicin," J. Invest. Dermatol. (1993) 101(1, Suppl):135S-137S.
Mansberger, S.L. et al., "Eyelash formation secondary to latanoprost treatment in a patient with alopecia," Arch. Ophthalmol. (2000) 118:718-719.
Maruyama, T. et al., "EP1 receptor antagonists suppress tactile allodynia in rats," Prostaglandins Lipid Mediat. (1999) 59:217.
Matias et al., "Prostaglandin ethanolamides (Prostamides): in vitro pharmacology and metabolism," J. Pharm. Exp. Thera. (2004) 309:745-757.
Matsumura, H., "Prostaglandins and Sleep," Saishin No to Shinkai Kagaku Shiritzu 10, 1998, pp. 79-89 (no English translation available).
Maw, G.N., "Pharmacological therapy for the treatment of erectile dysfunction," Annu. Rep. Med. Chem. (1999) 34:71-80.
Maxey, K.M., "The hydrolysis of bimatoprost in corneal tissue generates a potent prostanoid FP receptor agonist," Survey of Ophthalmology (2002) 47(1):S34-40.
McCullough, P.A., "Ridogrel,"Current Opinion in Anti-inflammatory & Immunomodulatory Investigation Drugs (1999) 1(3):265-276.
Mentlein, R. et al., "Hydrolysis of ester- and amide-type drugs by purified isoenzymes of nonspecific carboxylesterase from rat liver," Biochem. Pharm. (1984) 33:1243-1248.
Michelet, J.F. et al., "Activation of cytoprotective prostaglandin synthase-1 by minoxidil as a possible explanation for its hair growth-stimulation effect," J. Invest. Dermatol. (1997) 108(2):205-209.

Mihele, D., "The Testing of the Hepatoprotective Action of Some New Synthetic Prostaglandins," Farmacia (Bucharest) vol. 47 (5), 1999, pp. 43-58 (Abstract in English).
Millar, R.P. et al., "Diversity of actions of GnRHs mediated by ligand-induced selective signaling," Frontiers in Neuroendocrinology (2008) 29, 17-35.
Millikan, L.E., "Treatment of alopecia," J. Clin. Pharmacol. (1987) 27(9):715.
Millikan, L.E., "Treatment of male pattern baldness," Drug Therapy (1989) 19(3):62-73.
Mishima, H.K. et al., "A comparison of latanoprost and timolol in primary open-angle glaucoma and ocular hypertension," Arch. Ophthalmol. (1996) 114:929-932.
Mishima, S. et al., "Determination of tear volume and tear flow," Invest. Ophthal. (1966) 5(3):264-276.
Miyamoto, T., et al., "A comparison in the Efficacy and Safety between Ramatroban (BAY u 3405) and Ozargrel HC1 for Bronchial Asthma: A Phase III, Multi-Center, Randomized, Double-Blind, Group Comparative Study," 13, 1997, pp. 599-639 Abstract (in English).
Mori, S. et al., "Effects of prostaglandin E2 on production of new cancellous bone in the axial skeleton of overlectomized rats," Bone (1990) 11:103-113.
Morris, C.L. et al., "The role of bimatoprost eyelash gel in chemotherapy-induced madarosis: an analysis of efficacy and safety," Int. J. Trichology (2011) 3, 84-91.
Murakami, T. et al., "Effect of isocarbacyclin methyl ester incorporated in lipid microspheres on experimental models of peripheral obstructive disease," Arzheim.-Forsh/Drug Res. (1995) 45(Ii)(9):991-994.
Narumiya, S., "Roles of prostanoids in health and disease, lessons from receptor-knockout mice," Int. Congr. Ser. (1999) 1181:261-269.
Neau, S.H., "Pharmaceutical salts," Water-Insoluble Drug Formulation, Rong Liu editor, CRC Press (2008) 15:417-435.
Negishi, M. et al., "Molecular mechanisms of diverse actions of prostanoid receptors," Biochimica et Biophysica Acta (1995) 1259:109-120.
Ng, G.Y.K., "Phosphorylation and palmitoylation of the human D2L dopamine receptor in Sf9 cells," J. Neurochem. (1994) 63:1589-1595.
Norridin, R.W. et al., "The role of prostaglandins in bone in vivo," Prostaglandins, Leukotrienes and Essential Fatty Acids (1990) 41:139-149.
Ohashi, P.S. et al., "Reconstitution of an active surface T3/T-cell antigen receptor by DNA transfer," Nature (1985) 316:606-609.
Olsen, E.A. et al., "Transdermal viprostol in the treatment of male pattern baldness," J. Amer. Acad. Dermatol. (1990) 23(3 Part 1):470-472.
Orlicky, D.J., "Negative regulatory activity of a prostaglandin F2a receptor associated protein (FPRP)," Prostaglandins, Leukotrienes and Essential Fatty Acids (1996) 54(4):247-259.
Ortonne, J-P. et al., "Hair melanin's and hair color: ultrastructural and biochemical aspects," J. Soc. Inv. Derm. (1993) 82S-89S.
Ota, T. et al., "The effects of prostaglandin analogues on IOP in prostanoid FP receptor-deficient mice," Invest. Ophthal. Vis. Sci. (2005) 46, 4159-4163.
Ota, T. et al., The effects of prostaglandin analogues on prostanoid EP1, EP2, and EP3 receptor deficient mice, Invest. Ophthal. Vis. Sci. (2006) 47, 3395-3399.
Ozawa, A. et la., "Deorphanization of novel peptides and their receptors," Am. Assc. Pharm. Sci. (2010) 12(3):378-384.
Patton, T.F. et al., "Quantitative precorneal disposition of topically applied pilocarpine nitrate in rabbit eyes," J. Pharm. Sci. (1976) 65:1295-1301.
Pfeiffer, N., "New developments in glaucoma drug therapy," Ophthalmologist (1992) 89:W1-W13.
Phamaprojects, No. 6321, Merck & Co. (2006) 1 page.
Physician's Desk Reference (2001) Supplement A, "Lumigan" (Mar. 2001) 3 pages.
Pierce, K.L. et al., Cloning of a carboxyl-terminal isoform of the prostanoid FP receptor, J. Biol. Chem. (1997) 272, 883-887.
Pierce, K.L. et al., "Prostanoid receptor heterogeneity through alternative mRNA splicing," Life Sci. (1998) 62:1479-1483.

(56) References Cited

OTHER PUBLICATIONS

Pin, J-P et al., "Alternative splicing generates metabotropic glutamate receptors inducing different patterns of calcium release in *Xenopus oocytes*," Proc. Natl. Acad. Sci. (1992) 89, 10331-10335.

Powell, W.S. et al., "Prostaglandin F2alpha receptor in ovine *Corpora lutea*," Eur. J. Biochem. (1974) 41:103-107.

Poyer, J.F. et al., "Prostaglandin F2 alpha effects on isolated rhesus monkey ciliary muscle," Invest. Ophthalmol. Vis. Sci. (1995) 36(12):2461-2465.

Preparation of '404 patent documents for European Patent Office; Defendant Peter Thomas Roth Labs LLC and Peter Thomas Roth, Inc.,'s Invalidity Contentions Pursuant to Patent Local Rule 3-3 (Jun. 26, 2009).

Preparation of '404 Patent Documents for European patent Office; Defendants Metics LLC, Product Innovations LLC; Stella International LLC; and Nutra-Luxe, M.D. LLC's; Local Patent rule 3-3 Preliminary Invalidity Contentions (Jun. 26, 2009).

Rampton, D.S., Carty, E., Van Nueten, L., Anti-Inflammatory Profile in Vitro of Ridogrel, a Putative New Treatment for Inflammatory Bowel Disease, Gastroenterology, 1999, (116) G3477, p. 801.

Ramsey, D. et al., "Homo- and hetero-oligomeric interactions between G-protein-coupled receptors in living cells monitored by two variants of bioluminescence resonance energy transfer (BRET): Hetero-oligomers between receptor subtypes form more efficiently than between less closely related sequences," Biochem. J. (2002) 365:429.

Rath, C.M. et al., "Meta-omic characterization fo the marine invertebrate microbial consortium that produces the chemotherapeutic nature product ET-743," ACS Chem. Biol. (2011) 6, 1244-1256.

Regan, J.W. et al., "Cloning of a novel human prostaglandin receptor with characteristics of the pharmacologically defined EP2 subtype," Mol. Pharm. (1994) 46, 213-220.

Response from the Food and Drug Administration to Pfizer's Citizen Petition and a Supplement (Aug. 31, 2010) at 23 (Exhibit 5), 26 pages.

Resul, B. et al., "Phenyl-substituted prostaglandins: potent and selective antiglaucoma agents," J. Med. Chem. (1993) 36(2):243-248.

Roenigk, H.H., "New topical agents for hair growth," Clinics in Dermatology (1988) 6(4):119-121.

Romano, M.R., "Evidence for the involvement of cannabinoid CB1 receptors in the bimatoprost-induced contractions on the human isolated ciliary muscle," Invest. Opthal. Vis. Sci. (2007) 48(8):3677-3682.

Roof, S.L. et al., "mRNA expression of prostaglandin receptors EP1, EP2, EP3 and EP4 in human osteoblast-like cells and 23 human tissues," J. Bone Min. Res. (1996) 11:S337.

Rouzer, C.Z. et al., "Endocannabinoid oxygenation by cyclooxygenases, lipoxygenases, and cytochromes P450: cross-talk between the eicosanoid and endocannabinoid signaling pathways," Chem. Rev. (2011) 111:5899-5921.

Ruel, R. et al., "New class of biphenylene dibenzazocinones as potent ligands for the human EP1 prostanoid receptor," Bioorg. Med. Chem. Left. (1999) 9:2699-2704.

Saito, O. et al., "Expression of the prostaglandin F receptor (FP) gene along the mouse genitourinary tract," AJP-Renal Physiol. (2003) 284:F1164-1170.

Sakuma, Y. et al., "Crucial involvement of the PE4 subtype of prostaglandin E receptor in osteoclast formation by proinflammatory cytokines and lipopolysaccharide," J. Bone Min. Res. (2000) 15(2):218-227.

Salim, K. et al., "Oligomerization of G-protein-coupled receptors shown by selective co-immunoprecipitation," J. Biol. Chem. (2002) 277:15482-15483.

Satoh, T. et al., "The mammalian carboxylesterases: from molecules to functions," Ann. Rev. Pharmacol. & Toxicol. (1998) 38:257-288.

Sauk, J.J. et al., "Influence of prostaglandin E-1 prostaglandin E-2 and arachidonate on melanosomes in melanocytes and keratinocytes of anagen bulbs in-vitro," J. Invest. Dermatol. (1975) 64(5):332-337.

Scarselli, M. et al., "Reconsitution of functional dopamine D2s receptor by co-expression of amino- and carboxyl-terminal receptor fragments," Eur. J. Pharma. (2000) 397, 291-296.

Schaaf, T.K. et al., "Synthesis and biological activity of carboxyl-terminus modified prostaglandin analogues," J. med. Chem. (1979) 22:1340-1346.

Schachtsschabel, U. et al., "The mechanism of action of prostaglandins on oveosclerol outflow," Curr. Op. Ophthal. (2000) 11, 112-115.

Shanbhag, V.r. et al., "Ester and amide prodrugs of ibuprofen and naproxen: synthesis, anti-inflammatory activity, and gastrointestinal toxicity," J. Pharm. Sci. (1992) 81, 149-154.

Sharif, N.A. et al., "3H AL-5848 ([3H]9 beta-(+)-fluprostenol). Carboxylic acid of travoprost (AL-6221), a novel FP prostaglandin to study the pharmacology and autoradiographic localization of the FP receptor," J. Phar. Pharmacol. (1999) 51(6):685-694.

Sharif, N.A. et al., "Agonist activity of Bimatoprost, Tavoprost, Latanoprost, Unoprosone, Isopropyl Ester and other prostaglandin analogs at the cloned human ciliary body FP prostaglandin receptor," J. ocular Pharmacol. Therap. (2002) 18, 313-324.

Sharif, N.A. et al., "Bimatoprost (Lumigan) is an agonist at the cloned human ocular FP prostaglandin receptor: real-time FLIPR-based intracellular Ca2+ mobilization studies," Prostaglandin Leukotrienes & Essential Fatty Acids (2003) 68:27-33.

Sharif, N.A. et al., "Bimatoprost and its free acid are prostaglandin FP receptor agonists," Eur. J. Pharmacol. (2001) 432(2-3):211-213.

Sharif, N.A. et al., "Cat iris sphincter smooth-muscle contraction: comparison of FP-class prostaglandin analog agonist activities," J. Ocul. Pharmacol. Ther. (2008) 24(2):152-163.

Sharif, N.A. et al., "Human ciliary muscle cell responses to FP-class prostaglandin analogs: phosphoinositide hydrolysis, intracellular Ca2+ mobilization and MAP kinase activation," J. Ocul. Pharmacol. Ther. (2003) 19:437-455.

Sharif, N.A. et al., "Human trabecular meshwork cell responses induced by bimatoprost, travoprost, unoprostone, and other FP prostaglandin receptor agonist analogues," Invest. Ophthalmol. Vis. Sci. (2003) 44:715-721.

Sharif, N.A., "Ocular hypotensive FP prostaglandin (PG) analogs: PG receptor subtype binding affinities and selectivities, and agonist potencies at FP and other PG receptors in cultured cells," J. Ocular Pharm. Thera. (2003) 19(6):501-515.

Sharif, N.A., "Update and commentary on the pro-drug bimatoprost and a putative 'prostamide receptor'," Expert Rev. Ophthalmol. (2009) 4(5):477-489.

Sheerer, P. et al., "Crystal structure of opsin in its G-protein-interacting conformation," Nature (2008) 455, 497-502.

Shell, J.W., "Ophthalmic drug delivery systems," Survey Ophthal. (1984) 29(2):117-128.

Shell, J.W., "Pharmacokinetics of topically applied ophthalmic drugs," Surv. Ophthal. (1982) 26(4):207-218.

Sherwood, M. et al., "Six-month comparison of bimatoprost once-daily and twice-daily with timomol twice-daily in patients with elevated intraocular pressure," Surv. Ophthal. (2001) 45(4):5361-5368.

Shih, M.S. et al., "PGE2 induces regional remodeling changes in Haversian envelope: a histomorphometric study of fractured ribs in beagles," Bone and Mineral (1986) 1:227-234.

Shimazaki, A., et al. "New Ethacrynic Acid Derivatives as Potent Cytoskeletal Modulators in Trabecular Meshwork Cells," Biol. Pharm. Bull. vol. 27, No. 6, 2004, pp. 846-850.

Shimazaki, A., et al., "Effects of the New Ethacrynic Acid Derivative SA9000 on Intraocular Pressure in Cats and Monkeys," Biol Pharm. Bull. vol. 27, No. 7, 2004, pp. 1019-1024.

Singer, I.I. et al., "CCR5, CXCR4, and CD4 are clustered and closely apposed on microvilli of human macrophages and T cells," J. Virol. (2001) 75(8):3779-3790.

Sjoquist, B. et al., "Ocular and systemic pharmacokinetics of latanoprost in humans," Surv. Ophthalmol. (2002) 47(Supp 1):S6-12.

Sjoquist, B. et al., "Pharmacokinetics of latanoprost in the cynomolgus monkey. 3rd communication: tissue distribution after topical administration on the eye studied by whole body autoradiography, Glacoma research laboratories," Arzneimittelforschung (1999) 49:240-249.

(56) References Cited

OTHER PUBLICATIONS

Sorbera, L.A. et al., "Travoprost" Drugs of the Future (2000) 25(1):41-45.
Souillac, P. et al., "Characterization of delivery systems, differential scanning calorimetry," Encyclopedia of Controlled Drug Delivery, John Wiley & Sons (1999) 212-227.
Spada, C.S. et al., "Bimatoprost and prostaglandin F(2 alpha) selectively stimulate intracellular calcium signaling in different cat iris sphincter cells," Exp. Eye Res. (2005) 80(1):135-145.
Sredni, B. et al., "The protective role of the immunomodulator AS101 against chemotherapy-induced alopecia studies on human and animal models," Int. J. Cancer (1996) 65(1):97-103.
Stahl, P.H. et al., editors, Handbook of Pharmaceutical Salts, Properties, Selection and Use, Wiley-Vch (2008) Chapter 12, 265-327.
Stamer, W.D. et al., "Cellular basis for bimatoprost effects on human conventional outflow," Invest. Ophthalmol. Vis. Sci. (2010) 51(10):5176-5181, Epub Apr. 30, 2010.
Stern, F.A. et al., "Comparison of the hypotensive and other ocular effects of prostaglandins E2 and F2 alpha on cat and rhesus monkey eyes," Invest. Ophthal & Vis. Sci. (1982) 22, 588-598.
Stjernschantz et al., "Preclinical pharmacology of Latanoprost, a phenyl-substituted PGF2alpha analogue," Adv. Prostagldin Thromboxane & Leukotriene Res. (1995) 23:513-518.
Stjernschantz, J. et al., "Phenyl substituted prostaglandin analogs for glaucoma treatment," Drugs of the Future (1992) 17(8):691-704.
Stjernschantz, J., "Studies on ocular inflammation and development of a prostaglandin analogue for glaucoma treatment," Exp. Eye Res. (2004) 78(4):759-766.
Stjernschantz, J.W., "From PGF2alpha-isopropyl ester to latanoprost: a review of the development of Xalatan: the Proctor lecture," Invest. Ophthalmol. Vis. Sci. (2001) 42(6):1134-1145.
Stulting, R.D. et al., "Diagnosis and management of tear film dysfunction," in Corneal Disorders; Clinical Diagnosis and Management (Leibowitz et al. eds) (1998) Chapter 16, 482-500.
Svensson, et al., "The design and bioactivation of presystemically stable prodrugs," Drug Metabolism Rev. (1988) 19(2):165-194.
Swarbrick, J. et al., editors, Encyclopedia of Pharmaceutical Technology, Marcel Dekker, Inc. (1988) 13:453-499.
Tauchi, M. et al., "Characterization of an in vivo model for the study of eyelash biology and trichomegaly: mouse eyelash morphology, development, growth cycle and anagen prolongation by bimatoprost," Br. J. Derm. (2010) 162, 1186-1197.
Tereda, N. et al., "Effect of a thromboxane A2 receptor antagonist, ramatroban (BAY U3405), on inflammatory cells, chemical mediators and non-specific nasal hyperactivity after allergen challenge in patients with perennial allergic rhinitis," Allergology Int. (1998) 47(1):59-67.
The Newsletter of the Glaucoma Foundation, Fall 2000, vol. 11, No. 2, 11 pages.
Thomas, W. et al., "Stable expression of a truncated AT1A receptor in CHO-K1 cells," J. Biol. Chem. (1995) 270:207-213.
Tomasz, M., "Mitomycin C: small, fast and deadly (but very selective)," Chem. Biol. (1995) 2, 575-579.
Tomita, Y. et al., "Melanocyte-stimulating properties of arachidonic acid metabolites: possible role in postinflammatory pigmentation," Pigm. Cell Res. (1992) 5(5, Pt. 2):357-361.
Toris, C.B. et al., "Update on the mechanism of action of topical prostaglandins for intraocular pressure reduction," Surv. Ophthal. (2008) 53, S107-S120.
Travatan (Travoprost Opthalmic Solution) 0.04% Product Insert (Published Mar. 16, 2001), 7 pages.
Trinkaus-Randall, V. et al., "Corneal structure and function," in Corneal Disorders: Clinical Diagnosis and Management, Howard M. Leibowitz et al. eds., (1998) 2nd Edition, p. 2-31.
Trueb, R.M., "Chemotherapy—induced alopecia," Seminars Cutaneous Med. & Surg. (2009) 28, 11-14.
Ueda, K. et al., "Brief clinical and laboratory observations: coritical hyperostosis following long-term administration of prostaglandin E1 in infants with cyanotic congenital heart disease," J. Pediatrics (1980) 97:834-836.

Ungrin, M.D. et al., "Key structural features of prostaglandin E2 and prostanoid analogs involved in binding and activation of the human EP1 prostanoid receptor," Mol. Pharm. (2001) 59, 1446-1456.
Van Alphen, G.W.H.M. et al., "The effect of prostaglandins on the isolated internal muscles of the mammalian eye, including man," Documenta Ophthalmologica (1977) 42(2):397-415.
Van Santvliet, L. et al., "Determinants of eye drop size," Surv. Ophthal. (2004) 49(2):197-213.
Vandenburgh, A.M. et al., "A one-month dose-response study of AGN 192024, a novel antiglaucoma agent, in patients with elevated intraocular pressure," IOVS (1999) 40(4):4373-B176, p. S830.
Vandenburgh, A.M., reply to Alan L. Robin, "An accurate comparison of Bimatoprost's efficacy and adverse effects," Arch. Ophthal. (2002) 120:1000.
Vassilatis, D. et al., "The G protein-coupled receptor repertoires of human and mouse," Proc. Natl. Acad. Sci. USA (2003) 100, 4903-4908.
Vayssairat, M., Preventive Effect of an Oral Prostacyclin Analog, Beraprost Sodium, on Digital Necrosis in Systemic Scierosis, J. of Rheumatol., 1999, 26(10), pp. 2173-2178.
Vengerovsky, A.I. et al., "Hepatoprotective action of prostaglandins," Eksp. Klin. Farmakof. (1997) 60(5):78-82.
Verbeuren, T., et al., "The TP-Receptor Antagonist S 18886 Unmasks Vascular Relaxation and Potentiates the Anti-Platelet Action of PGD2," Journal of the International Society Thrombosis and Haemostasis, Jun. 6-12, 1997, p. 693.
Vielhauer, G.A. et al., "Cloning and localization of hFP(S): a six-transmembrane mRNA splice variant of the human FP prostanoid receptor," Arch. Biochem. Biophys. (2004) 421(2):175-185.
Villumsen, J. et al., "Prostaglandin F2alpha-isopropylester eye drops: effect on intraocular pressure in open-angle glaucoma," Br. J. Ophthalmol. (1989) 73:975-979.
Vincent, J.E., "Prostaglandin synthesis and selenium deficiency a hypothesis," Prostaglandins (1974) 8(4):339-340.
Vippagunta, "Crystalline solids," Adv. Drug Del. Rev. (2001) 48:3-26.
Voss, N.G. et al., "Induction of anagen hair growth in telogen mouse skin by topical latanoprost application," IOVS (1999) 40:3570-B428, p. S676.
Waddell, K. A., et al., "Combined Capillary col. Gas Chromatography Negative Ion Chemical Ionization Mass Spectrometry of Prostanoids," Biomed. Mass Spectrom., vol. 10, No. 2, pp. 83-88 (1983).
Walsh, D.A. et al., "Anti-inflammatory agents, syntheses and biological evaluation of potential prodrugs of 2-amino-3-benzoylbenzeneacetic acid and 2-amino-3-(4-chlorobenzoyl)benzeneacetic acid," J. Med. Chem. (1990) 33:2296-2304.
Wan, Z. et al., "Bimatoprost, prostamide activity, and conventional drainage," Invest. Ophthal. Vis. Sci. (2007) 48, 4107-4115.
Wand, M., "Latanoprost and hyperpigmentation of eyelashes," Archives of Ophthalmology (1997) 115(9):1206-1208.
Wang, Y. et al., "The design and synthesis of 13, 14-dihydro prostaglandin F1a analogs as potent and selective ligands for the human FP receptor," J. Med. Chem. (2000) 43(5):945-952.
Warne, T. et al., "Expression and purification of truncated, non-glycosylated Turkey beta-adrenergic receptors for crystallization," Biochimica et Biophysica Acta—Biomembranes (2003) 1610, 133-140.
Warne, T. et al., "Structure of a beta1-adrenergic G-protein-coupled receptor," Nature (2008) 454:486-491.
Watson et al., "A six-month, randomized, double-masked study in comparing latanoprost with timolol in open-angle glaucoma and ocular hypertension," Ophthalmology (1996) 103:126-137.
Weber, A. et al., "Formation of prostamides from anandamide in FAAH knockout mice analyzed by HPLC with tandem mass spectrometry," J. Lipid Res. (2004) 45, 757-763.
White, J.H. et al., "Heterodimerization is required for the formation of a functional GABA(B) receptor," Nature (1998) 396(6712):679-682.
Whitson, J.T., "Travoprost—a new prostaglandin analogue for the treatment of glaucoma," Exp. Op. Pharmacotherapy (2002) 3(7):965-977.

(56) References Cited

OTHER PUBLICATIONS

Wilson, S.J. et al., "Dimerization of the human receptors for prostacyclin and thromboxane facilitates thromboxane receptor-mediated cAMP generation," J. Biol. Chem. (2004) 279(51):53036-53047.
Winfield, A.J. et al., "A study of the causes of non-compliance by patients prescribed eyedrops," Br. J. Ophthal. (1990) 74:477-480.
Witkowski, A. et al., "Head-to-head coiled arrangement of the subunits of the animal fatty acid synthase," Chem. Biol. (2004) 11, 1667-1676.
Woodward, D., "Replacement of carboxylic acid group of prostaglandin F2a with a hydroxyl or methoxy substituent provides biologically unique compounds," Br. J. Pharma. (2000) 130(8):1933-1943.
Woodward, D.F. et al., "Bimatoprost effects on aqueous humor dynamics in monkeys," J. Ophthalmol. (2010) Article ID 926192, 5 pages.
Woodward, D.F. et al., "Bimatoprost: a novel antiglaucoma agent," Cardiovasc. Drug Rev. (2004) 22(2):103-120.
Woodward, D.F. et al., "Emerging evidence for additional prostanoid receptor subtypes," Curr. Top. Pharmacol. (1998) 4:153-163.
Woodward, D.F. et al., "Identification of an antagonist that selectively blocks the activity of prostamides (prostaglandin-ethanolamides) in the feline iris," Br. J. Pharmacol. (2007) 150:342-352.
Woodward, D.F. et al., "Molecular characterization and ocular hypotensive properties of the prostanoid EP2 receptor," J. Oc. Pharm. Therap. (1995) 11(3):447-454.
Woodward, D.F. et al., "Pharmacological characterization of a novel anti-glaucoma agent," J. Pharmacol. Exp. Ther. (2003) 305:772-785.
Woodward, D.F. et al., "Prostaglandins F2alpha (PGF2alpha) 1-ethanolamide: a pharmacologically unique local hormone biosynthesized from anandamide," 11th Int. Conf. Advances Prostaglandin & Leukotrine Res: Basic Sci and New Clinical Applications—abstract book (2000) 27.
Woodward, D.F. et al., "Studies on the ocular effects of a pharmacologically novel agent prostaglandin F2 alpha 1-OCH3 (AGN 191129) N-S," Arch. Pharmacol. (1998) 358(1):P1713.
Woodward, D.F. et al., "The pharmacology of bimatoprost (Lumigan)," Surv. Ophthalmol. (2001) 45(Suppl 4):S337-45.
Xalatan (Latanoprost Opthalmic Solution) 0.005% product insert (Published Jun. 6, 2001), 5 pages.
Yamaji, K. et al., "Prostaglandins El and E2, but not F2alpha or latanoprost, inhibit monkey ciliary muscle contraction," Curr. Eye Res. (2005) 30(8):661-665.
Yang, W. et al., "Enzymatic formation of prostamide F2alpha from anandamide involves a newly identified intermediate metabolite, prostamide H2," J. Lipid Res. (2005) 46, 2745-2751.
Yoshida, K. et al., "Synthesis and pharmacological activities of the new TXA2 receptor antagonist Z-335 and related compounds," AFMC (1995) 95:53.
Yuan, X. et al., "Quantitative proteomics: comparison of the macular bruch membrane/choroid complex from age-related macular degeneration and normal eyes," Mol. Cell Proteomics (2010) 9:1031-1046.
Zeigler, T., "Old drug, new use: new research shows common cholesterol-lowering drug reduces multiple sclerosis symptoms in mice," Natl. Institute of Neurological Disorders and Stroke (2003) 2 pages.
Zimbric, M.L. et al., "Effects of latanoprost of hair growth in the bald scalp of stumptailed macaques," IOVS (1999) 40:3569-B427, p. S676.
Zioptan (Tafluprost Opthalmic Solution) 0.0015% product insert (Published Feb. 10, 2012), 12 pages.
International Search Report for Application No. PCT/US00/05301 (WO 00/51980) dated Jul. 21, 2000 (3 pages).
Written Opinion for Application No. PCT/US00/05301 (Wo 00/51980) dated Oct. 20, 2000 (7 pages).
International Preliminary Examination Report for Application No. PCT/US00/05301 (WO 00/51980) dated Mar. 16, 2001 (6 pages).
International Search Report for Application No. PCT/US00/20851 (WO 01/10873) dated Nov. 7, 2000 (4 pages).
Written Opinion for Application No. PCT/US00/20851 (WO 01/10873) dated Jul. 10, 2001 (9 pages).
International Preliminary Examination Report for Application No. PCT/US00/20851 (WO 01/10873) dated Oct. 12, 2001 (8 pages).
International Search Report for Application No. PCT/US98/18339 (WO 99/12895) dated Dec. 3, 1998 (2 pages).
International Preliminary Examination Report for Application No. PCT/US98/18339 (WO 99/12895) dated Jun. 28, 1999 (4 pages).
International Search Report for Application No. PCT/US98/18340 (WO 99/12896) dated Dec. 8, 1998 (3 pages).
Written Opinion for Application No. PCT/US98/18340 (WO 99/12896) dated Aug. 2, 1999 (7 pages).
International Preliminary Examination Report for Application No. PCT/US98/18340 (WO 99/12896) dated Dec. 6, 1999 (7 pages).
International Search Report for Application No. PCT/US98/18594 (WO 99/12898) dated Dec. 3, 1998 (3 pages).
Written Opinion for Application No. PCT/US98/18594 (WO 99/12898) dated May 25, 1999 (5 pages).
International Preliminary Examination Report for Application No. PCT/US98/18594 (WO 99/12898) dated Sep. 7, 1999 (5 pages).
International Search Report for Application No. PCT/IB99/00478 (WO 99/50241) dated Jul. 12, 1999 (3 pages).
Written Opinion for Application No. PCT/IB99/00478 (WO 99/50241) dated Feb. 21, 2004 (4 pages).
International Preliminary Examination Report for Application No. PCT/IB99/00478 (WO 99/50241) dated Jun. 23, 2000 (5 pages).
International Search Report for Application No. PCT/IB99/00480 (WO 99/50242) dated Jun. 25, 1999 (3 pages).
Written Opinion for Application No. PCT/IB99/00480 (WO 99/50242) dated Jan. 18, 2000 (6 pages).
International Search Report for Application No. PCT/US00/05299 (WO 99/51979) dated Jul. 28, 2000 (3 pages).
Written Opinion for Application No. PCT/US00/05299 (WO 99/51979) dated Oct. 20, 2000 (7 pages).
International Preliminary Examination Report for Application No. PCT/US00/05299 (WO 99/51979) dated Mar. 16, 2001 (7 pages).
International Search Report for Application No. PCT/US01/10368 (WO 01/74313) dated Nov. 7, 2001 (3 pages).
International Preliminary Examination Report for Application No. PCT/US01/10368 (WO 01/74313) dated Jun. 14, 2002 (2 pages).
International Search Report for Application No. PCT/US01/10369 (WO 01/74314) dated Nov. 7, 2001 (3 pages).
International Preliminary Examination Report for Application No. PCT/US01/10369 (WO 01/74314) dated Jun. 14, 2001 (3 pages).
International Search Report for Application No. PCT/US01/10370 (WO 01/74315) dated Nov. 7, 2001 (3 pages).
International Preliminary Examination Report for Application No. PCT/US01/10370 (WO 01/74315) dated Jun. 14, 2002 (2 pages).
International Search Report for Application No. PCT/US01/10547 (WO 01/74307) dated Jan. 2, 2002 (2 pages).
International Preliminary Examination Report for Application No. PCT/US01/10547 (WO 01/74307) dated Jun. 14, 2002 (2 pages).
Invitation to Pay Additional Fees and Partial International Search for Application No. PCT/US2009/062590 (WO 2010/096123) dated Aug. 19, 2010 (5 pages).
International Search Report and Written Opinion for Application No. PCT/US2009/062590 (WO 2010/096123) dated Nov. 16, 2010 (16 pages).
Invitation to Pay Additional Fees and Partial International Search for Application No. PCT/US2010/43701 dated Sep. 28, 2010 (2 pages).
International Search Report and Written Opinion for Application No. PCT/US2010/43701 dated Dec. 7, 2010 (10 pages).
International Search Report and Written Opinion for Application No. PCT/US2010/27831 (WO 2010/108012) dated Apr. 26, 2010 (8 pages).
Chinese Office Action dated Jun. 22, 2007 (7 pages) for Chinese Application No. 01807355.7, claiming priority to International Application No. PCT/US01/10370 (WO 01/74315) filed Mar. 30, 2001 and U.S. Appl. No. 60/193,645, filed Mar. 31, 2000.
Chinese Office Action dated Feb. 4, 2005 (9 pages) for Chinese Application No. 01807355.7, claiming priority to International Application No. PCT/US01/10370 (WO 01/74315) filed Mar. 30, 2001 and U.S. Appl. No. 60/193,645, filed Mar. 31, 2000.

(56) References Cited

OTHER PUBLICATIONS

Canadian Office Action dated Nov. 28, 2005 (2 pages) for Canadian Application No. 2401731, claiming priority to International Application No. PCT/US01/10370 (WO 01/74315) filed Mar. 30, 2001 and U.S. Appl. No. 60/193,645, filed Mar. 31, 2000.
Canadian Office Action for Canadian Application No. 2401731 dated Oct. 1, 2004 (3 pages), claiming priority to International Application No. PCT/US01/10370 (WO 01/74315) filed Mar. 30, 2001 and U.S. Appl. No. 60/193,645, filed Mar. 31, 2000.
Chinese Patent Office Action dated Nov. 13, 2009 (9 pages) for Chinese Application No. 200810081548.8, claiming priority to International Application No. PCT/US01/10370 (WO 01/74315) filed Mar. 30, 2001 and U.S. Appl. No. 60/193,645, filed Mar. 31, 2000.
Chinese Patent Office Action dated May 23, 2011 (13 pages) for Chinese Application No. 201010193487.1, claiming priority to International Application No. PCT/US01/10370 (WO 01/74315) filed Mar. 30, 2011 and U.S. Appl. No. 60/193,645, filed Mar. 31, 2000.
Chinese Patent Office Action dated Jul. 6, 2012 (6 pages) for Chinese Application No. 201010193487.1, claiming priority to International Application No. PCT/US01/10370 (WO 01/74315) filed Mar. 30, 2011 and U.S. Appl. No. 60/193,645, filed Mar. 31, 2000.
Chinese Patent Office Action dated Feb. 6, 2013 (12 pages) for Chinese Application No. 201010193487.1, claiming priority to International Application No. PCT/US01/10370 (WO 01/74315) filed Mar. 30, 2011 and U.S. Appl. No. 60/193,645, filed Mar. 31, 2000.
European Patent Office Action dated May 13, 2004 (4 pages) for European Application No. 01926506.5, claiming priority to International Application No. PCT/US01/10370 (WO 01/74315) filed Mar. 30, 2001 and U.S. Appl. No. 60/193,645, filed Mar. 31, 2000.
Japanese Patent Office Action dated Jun. 7, 2011 (10 pages) for Application No. 2001-572061, claiming priority to International Application No. PCT/US01/10370 (WO 01/74315 filed Mar. 30, 2001 and U.S. Appl. No. 60/193,645, filed Mar. 31, 2000.
Japanese Patent Office Action dated Apr. 30, 2013 (10 pages—Including English Translation) for Application No. 2011-262344, claiming priority to International Application No. PCT/US01/10370 (WO 01/74315 filed Mar. 30, 2001 and U.S. Appl. No. 60/193,645, filed Mar. 31, 2000.
Complaint for Patent Infringement, U.S. District Court for Middle District of North Carolina, *Allergan, Inc. et al.*, v. *Hi-Tech Pharmacal Co., Inc.*, Case No. 1:11-CV-650, filed Aug. 17, 2011 (11 pages).
Hi-Tech Pharmacal Co., Inc.'s Answer to Allergan, Inc.'s and Duke University's Complaint Against Hi-Tech for Patent Infringement, U.S. District Court for Middle District of North Carolina, *Allergan, Inc. et al.* v. *Hi-Tech Pharmacal Co., Inc.*, Case No. 1:11-CV-650, filed Oct. 7, 2011 (18 pages).
Allergan, Inc. and Duke University's Answer to Counterclaims of Hi-Tech Pharmacal Co., Inc., U.S. District Court for Middle District of North Carolina, *Allergan, Inc. et al.* v. *Hi-Tech Pharmacal Co., Inc.*, Case No. 1:11-CV-650, filed Oct. 31, 2011 (8 pages).
Defendant Hi-Tech Pharmacal Co., Inc's Responses to Plaintiffs First Set of Interrogatories, U.S. District Court for the Middle District of North Carolina, *Allergan, Inc. et al.*, v. *Hi-Tech Pharmacal Co., Inc.*, Case No. 1:11-CV-650 dated Feb. 21, 2012 (14 pages).
Complaint for Patent Infringement, U.S. District Court, North Carolina Middle District, *Allergan, Inc. et al* v. *Sandoz, Inc.*, Case No. 1:11-cv-00298-CCE -WWD, filed Apr. 15, 2011 (12 pages).
Defendant Sandoz Inc.'s Answer, Affirmative Defenses and Counterclaim, U.S. District Court, North Carolina Middle District, *Allergan, Inc. et al* v. *Sandoz, Inc.*, Case No. 1:11-cv-00298-CCE -WWD, filed May 27, 2011 (29 pages).
Allergan, Inc. and Duke University's Answer to Counterclaims of Sandoz Inc., U.S. District Court, North Carolina Middle District, *Allergan, Inc. et al* v. *Sandoz, Inc.*, Case No. 1:11-cv-00298-CCE -WWD, filed Jun. 20, 2011 (6 pages).
Defendants Apotex Inc., Apotex Corp., Sandoz, Inc. and Hi-Tech Pharmacal Co., Inc.'s Supplemental Joint Submission Concerning Inquiry by the Court During the Claim Construction Hearing, U.S. District Court for the Middle District of North Carolina, *Allergan, Inc. et al.* vs. *Apotex Inc.* et al., Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Aug. 2, 2012 (7 pages).
Defendant Sandoz Inc.'s First Set of Supplemental Responses to Plaintiffs' First Set of Interrogatories (Nos. 5, 6, and 11), U.S. District Court for the Middle District of North Carolina, *Allergan, Inc.* et al. v. *Apotex Inc. et al.* and *Allergan, Inc. et al.* v. *Sandoz, Inc.*, Case Nos. 1:10-CV-681-CCE-PTS and 1:11-CV-298-CCE-PTS dated Feb. 7, 2012 (39 pages).
Expert Report of Dr. David H. Sherman, Ph.D., Pursant to Federal Rule of Civil Procedure 26(a)(2)(B), U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Apr. 27, 2012, redacted (81 pages).
Expert Report of Howard M. Leibowitz, M.D., Pursant to Federal Rule of Civil Procedure 26(a)(2)(B), U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co.*, Inc., Case No. 1:11-CV-650 dated Apr. 27, 2012, redacted (43 pages).
Reply Expert Report of Vesna Petronic-Rosic, M.D., Pursant to Federal Rule of Civil Procedure 26(a)(2)(B), U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Jun. 19, 2012, redacted (10 pages).
Reply Expert Report of Dr. David H. Sherman, Ph.D., Pursant to Federal Rule of Civil Procedure 26(a)(2)(B), U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Jun. 19, 2012, redacted (79 pages).
Apotex's Fifth Supplemental and/or Amended Responses and Objections to Allergan, Inc.'s and Duke University's First Set of Interrogatories to Defendants Apotex Inc. and Apotex Corp. (Interrogatory Nos. 5 and 6), U.S. District Court for the Middle District of North Carolina, *Allergan, Inc. et al.*, v. *Apotex Inc. et al.*, Case No. 1:10-CV-681 dated Aug. 24, 2012, redacted (46 pages).
Defendant Sandoz Inc.'s Second Set of Supplemental Responses to Plaintiffs' First Set of Interrogatories (Nos. 5 and 6), U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Sep. 10, 2012, redacted (80 pages).
Defendant Hi-Tech Pharmacal Co., Inc.'s Supplemental Responses to Plaintiffs First Set of Interrogatories, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650, redacted, dated Sep. 13, 2012 (44 pages).
Plaintiffs' Opening Brief in Support of Plaintiffs' Motion in Limine No. 1 to Exclude Expert Opinions on Anticipation and Obviousness Not Disclosed in Expert Reports, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Sep. 10, 2012 (13 pages).
Deposition Transcript of Howard M. Leibowitz, M.D. taken Jul. 26, 2012, portions thereof, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650, filed Sep. 10, 2012 (7 pages).
Defendants Apotex, Sandoz, and Hi-Tech's Brief in Opposition to Plaintiffs' Motion in Limine No. 1, U.S. District Court for the Middle District of North Carolina, *Allergan, Inc. et al.* vs. *Apotex Inc. et al.*,

(56) References Cited

OTHER PUBLICATIONS

Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Oct. 4, 2012 (18 pages).
Deposition of Howard M. Leibowitz, M.D., taken Jul. 26, 2012, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 submitted Oct. 4, 2012, (332 pages).
Stipulated Facts, U.S. District Court for the Middle District of North Carolina, *Allergan, Inc.* et al. vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Oct. 26, 2012 (9 pages).
Plaintiffs' Brief in Opposition to Defendants' Motion in Limine No. 1 on the Alleged Invention Dates for the Patents-in-suit, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Nov. 1, 2012 (14 pages).
Excerpts of Transcript of Deposition of Timothy L. MacDonald dated Aug. 22, 2012, pp. 1, 26-27, 34-36, and 164-166 in *Allergan, Inc.* v. *Apotex, Inc.*, Case No. 1:10CV681 (M.D. North Carolina).
Trial Transcript Day 5—Nov. 9, 2012—Testimony of Howard Leibowitz, and Dr. David Howard Sherman in *Allergan, Inc.* v. *Apotex, Inc.*, Case No. 1:10CV681 (M.D. North Carolina).
Trial Transcript Day 6—Nov. 13, 2012—Testimony of Dr. David Howard Sherman, Robert Noecker, Robert Rhatigan, Dr. John Regan, in *Allergan, Inc.* v. *Apotex, Inc.*, Case No. 1:10CV681 (M.D. North Carolina).
Trial Transcript Day 7—Nov. 19, 2012—Testimony of Dr. John Regan, Dr. Valerie Randall, Dr. Timothy MacDonald, in *Allergan, Inc.* v. *Apotex, Inc.*, Case No. 1:10CV681 (M.D. North Carolina).
Trial Transcript Day 8—Nov. 20, 2012—Testimony of Dr. Timothy MacDonald, David H. Sherman, Harry Charles Boghigian, in *Allergan, Inc.* v. *Apotex, Inc.*, Case No. 1:10CV681 (M.D. North Carolina).
Defendants' Memorandum in Support of Their Motion for Partial Judgment Under Federal Rule of Civil Procedure 52(c) that Plaintiffs Have Failed to Prove Alleged Conception Dates Earlier Than the Priority Filing Dates for the Patents-in-Suit, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Nov. 25, 2012 (21 pages).
Claim Construction Order, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Nov. 27, 2012 (3 pages).
Designated Excerpts From Brandt Deposition Submitted by Defendants at Trial (DTX 1035), U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (29 pages).
Plaintiffs' Brief in Opposition to Defendants' "Motion for Partial Summary Judgment Under Federal Rule of Civil Procedure 52(c) that Plaintiffs have Failed to Prove Alleged Conception Dates Earlier than the Priority Filing Dates for the Patents-in-Suit," U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (23 pages).
Defendants' Opening Post-Trial Brief, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (61 pages).
Appendix A of Defendants' Opening Post-Trial Brief, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (2 pages).
Appendix B of Defendants' Opening Post-Trial Brief, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (7 pages).
Appendix C of Defendants' Opening Post-Trial Brief, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (10 pages).
Appendix D of Defendants' Opening Post-Trial Brief, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (6 pages).
Appendix E of Defendants' Opening Post-Trial Brief, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (11 pages).
Appendix F of Defendants' Opening Post-Trial Brief, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*,v. *Hi-Tech Pharmacol Co., Inc.*, Case No. 1:11-CV-650 dated Dec. 10, 2012 (3 pages).
Appendix G of Defendants' Opening Post-Trial Brief, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (8 pages).
Appendix H of Defendants' Opening Post-Trial Brief, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (12 pages).
Appendix I of Defendants' Opening Post-Trial Brief, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (17 pages).
Defendants' Findings of Fact and Conclusions of Law, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (89 pages).
Defendants' Responsive Post-Trial Brief, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 10, 2012 (33 pages).
Defendants' Reply Memorandum in Support of Their Motion for Partial Judgment Under Federal Rule of Civil Procedure 52(c) that Plaintiffs have Failed to Prove Alleged Conception Dates Prior to the

(56) References Cited

OTHER PUBLICATIONS

Priority Filing Dates for the Patents-in-Suit, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Dec. 21, 2012 (14 pages).
Judgment, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc.* et al., v. *Hi-Tech Pharmacol Co., Inc.*, Case No. 1:11-CV-650 dated Jan. 25, 2013 (2 pages).
Memorandum Opinion and Order Upholding Validity of Parent U.S. Patent No. 7,388,029, U.S. District Court for the Middle District of North Carolina, *Allergan, Inc. et al.* vs. *Apotex Inc. et al.*, Case No. 1:10-CV-681; *Allergan, Inc. et al.*, v. *Sandoz Inc.*, Case No. 1:11-CV-298; and *Allergan, Inc. et al.*, v. *Hi-Tech Pharmacol Co., Inc.*, Case No. 1:11-CV-650 dated Jan. 24, 2013, (25 pages).
Complaint for Patent Infringement, U.S. District Court, Middle Court of North Carollina, *Allergan, Inc. et al.*, v. *Apotex Inc. et al.*, Case No. 1:10-CV-681, Document 1, filed Sep. 8, 2010, 12 pages.
Answer, Defenses and Counterclaims of Defendants Apotex Inc. And Apotex Corporation, U.S. District Court, Middle Court of North Carolina, *Allergan, Inc. et al.*, v. *Apotex Inc. et al.*, Case No. 1:10-CV-681, Document 24, filed Nov. 22, 2010, 20 pages.
Allergan, Inc. and Duke University's Answer to Counterclaims of Apotex, Inc. and Apotex Corporation, U.S. District Court, Middle Court of North Carolina, *Allergan, Inc. et al.* v. *Apotex Inc. et al.*, Case No. 1:10-CV-681, Document 26, filed Jan. 7, 2011, 6 pages.
Complaint for Patent Infringement, Demand for Jury Trial, U.S. District Court, Central District of California (Southern Division), *Allergan, Inc. et al.* v. *Athena Cosmetics Inc. et al.*, Case No. 8:09-cv-00328-JVS-RNB, Document 1, Filed Apr. 27, 2009 (126 pages).
Defendant Metics, LLC's Answer to Complaint for Patent Infringement, U.S. District Court, Central District of California (Southern Division), *Allergan, Inc. et al.* v. *Athena Cosmetics Inc. et al.*, Case No. 8:09-cv-00328-JVS-RNB, Document 25, Filed Apr. 7, 2009 (13 pages).
Defendant Peter Thomas Roth Labs LLC's Answer to Complaint for Patent Infringement, U.S. District Court, Central District of California (Southern Division), *Allergan, Inc. et al.* v. *Athena Cosmetics Inc. et al.*, Case No. 8:09-cv-00328-JVS-RNB, Document 48, Filed Apr. 27, 2009 (12 pages).
Answer and Counterclaims of Defendants Athena Cosmetics, Inc. to Plaintiffs Allergan, Inc., Murray A. Johnstone, and Duke University's Complaint and Demand for Jury Trial, U.S. District Court, Central District of California (Southern Division), *Allergan, Inc. et al.* v. *Athena Cosmetics Inc. et al.*, Case No. 8:09-cv-00328-JVS-RNB, Document 54, Filed Apr. 27, 2009 (170 pages).
Answer and Counterclaims of Defendant Pharma Tech International., Inc. to Plaintiffs Allergan, Inc., Murray A. Johnstone, and Duke University's Complaint and Demand for Jury Trial, U.S. District Court, Central District of California (Southern Division), *Allergan, Inc. et al.* v. *Athena Cosmetics Inc. et al.*, Case No. 8:09-cv-00328-JVS-RNB, Document 55, Filed Apr. 27, 2009 (19 pages).
Answer and Counterclaims of Defendant Pharma Tech International, Inc. to Plaintiffs Allergan, Inc., Murray A. Johnstone, and Duke University's Complaint and Demand for Jury Trial, U.S. District Court, Central District of California (Southern Division), *Allergan, Inc. et al.* v. *Athena Cosmetics Inc. et al.*, Case No. 8:09-cv-00328-JVS-RNB, Document 56, Filed Apr. 28, 2009 (19 pages).
Answer and Counterclaims of Defendants Athena Cosmetics, Inc. to Plaintiffs Allergan, Inc., Murray A. Johnsone, and Duke University's complaint and Demand for Jury Trial, U.S. District Court, Central District of California (Southern Division), *Allergan, Inc. et al.* v. *Athena Cosmetics Inc. et al.*, Case No. 8:09-cv-00328-JVS-RNB, Document 57, Filed Apr. 28, 2009 (170 pages).
Defendants Peter Thomas Roth Labs LLC and Peter Thomas Roth, Inc.'s first Amended Answer to Complaint for Patent Infringement, U.S. District Court, Central District of California (Southern Division), *Allergan, Inc. et al.* v. *Athena Cosmetics Inc. et al.*, Case No. 8:09-cv-00328-JVS-RNB, Document 61, Filed May 7, 2009 (13 pages).
Answer of Defendants Lifetech Resources LLC and Rocasuba Inc. to Complaint for Patent Infringement, U.S. District Court, Central District of California (Southern Division), *Allergan, Inc. et al.* v. *Athena Cosmetics Inc. et al.*, Case No. 8:09-cv-00328-JVS-RNB, Document 64, Filed May 8, 2009 (13 pages).
First Amended Answer and Counterclaims of Defendant Athena Cosmetics, Inc., to Plaintiffs Allergan, Inc., Murray A. Johnstone, and Duke University's Complaint and Demand for Jury Trial, U.S. District Court, Central District of California (Southern Division), *Allergan, Inc. et al.* v. *Athena Cosmetics Inc. et al.*, Case No. 8:09-cv00328-JVS-RNB, Document 65, Filed May 7, 2009 (65 pages).
First Amended Complaint for Patent Infringement, Violation of California Business and Professions Code Section 17200 et seq., and Demand for Jury Trial, U.S. District Court, Central District of California (Southern Division), *Allergan, Inc. et al.* v. *Athena Cosmetics Inc. et al.*, Case No. 8:09-cv-00328-JVS-RNB, Document 86, Filed Aug. 10, 2009 (129 pages).
Answer of Defendants Lifetech Resources, LLC and Rocasuba, Inc. to First Amended Complaint for Patent Infringement, Violation of California Business and Professions Code Section 17200 et seq., and Demand for Jury Trial, U.S. District Court, Central District of California (Southern Division), *Allergan, Inc. et al.* v. *Athena Cosmetics Inc. et al.*, Case No. 8:09-cv-00328-JVS-RNB, Document 89, Filed Sep. 8, 2009 (18 pages).
Answer of Defendants Cosmetic Alchemy, LLC; Metics, LLC; Product Innovations, LLC; and Stella International, LLC to Amended Complaint, U.S. District Court, Central District of California (Southern Division), *Allergan, Inc. et al.* v. *Athena Cosmetics Inc. et al.*, Case No. 8:09-cv-00328-JVS-RNB, Document 90, Filed Sep. 11, 2009 (14 pages).
Answer of Defendant Nutra-Luxe MD to Amended Complaint, U.S. District Court, Central District of California (Southern Division), *Allergan, Inc. et al.* v. *Athena Cosmetics Inc. et al.*, Case No. 8:09-cv-00328-JVS-RNB, Document 91, Filed Sep. 11, 2009 (14 pages).
First Amended Complaint for Patent Infringement, Violation of California Business and Professions Code Section 17200 et seq., and Demand for Jury Trial, U.S. District Court, Central District of California (Southern Division), *Allergan, Inc. et al.* v. *Athena Cosmetics Inc. et al.*, Case No. 8:09-cv-00328-JVS-RNB, Document 95, Filed Oct. 22, 2009 (128 pages).
Order Entering Final Judgment Pursuant to Federal Rule of Civil Procedure 54(b) on Plaintiff Allergan, Inc.'s Fourth Claim for Relief in Favor of Defendants and Stay of Trial Court Proceedings Pending Appeal, U.S. District Court, Central District of California (Southern Division), *Allergan, Inc. et al.* v. *Athena Cosmetics Inc. et al.*, Case No. 8:09-cv-00328-JVS-RNB, Document 101, filed May 5, 2010 (2 pages).
Complaint for Patent Infringement and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 1, Filed Nov. 7, 2007 (12 pages).
First Amended Complaint for Patent Infringement and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 7, Filed Dec. 20, 2007 (8 pages).
Defendant Jan Marini Skin Research Inc.'s Answer to Plaintiff Allergan, Inc.'s Second Amended Complaint for Patent Infringement, U.S. District Court, Central District of California (Southern Division), *Allergan, Inc. et al.* v. *Cayman Chemical Company et al.*, Case No. 8:07-cv-01316-JVS-RNB, Document 75, Filed Apr. 2, 2008 (11 pages).
Answer and Counterclaims of Defendant Athena Cosmetics, Inc. to Plaintiffs Allergan, Inc. and Murray A. Johnstone's Second Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 79, Filed Apr. 2, 2008 (15 pages).

(56) References Cited

OTHER PUBLICATIONS

Second Amended Complaint for Patent Infringement and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 87, Filed May 8, 2008 (38 pages).

Third Amended Complaint for Patent Infringement and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 90, Filed May 15, 2008 (52 pages).

Answer to Third Amended Complaint and Additional Defenses of Defendant Photomedex, Inc., U.S. District Court, Central District of California (Southern Division), *Allergan, Inc. et al.* v. *Cayman Chemical Company et al.*, Case No. 8:07-cv-01316-JVS-RNB, Document 91, Filed May 23, 2008 (8 pages).

Answer to Third Amended Complaint by Beauty Society, Inc., Formerly Intuit Beauty, Inc. and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 92, Filed May 23, 2008 (11 pages).

Defendant Jan Marini Skin Research Inc.'s Answer to Plaintiff Allergan, Inc.'s Third Amended Complaint for Patent Infringement, U.S. District Court, Central District of California (Southern Division), *Allergan, Inc. et al.* v. *Cayman Chemical Company et al.*, Case No. 8:07-cv-01316-JVS-RNB, Document 94, Filed May 23, 2008 (12 pages).

Answer and Counterclaims of Defendant Athena Cosmetics, Inc. to Plaintiffs Allergan, Inc. and Murray A. Johnstone's Third Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 98, Filed May 23, 2008 (20 pages).

Amended Answer and Counterclaims of Defendant Athena Cosmetics, Inc. to Plaintiffs Allergan, Inc., and Murray A. Johnstone's Third Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 111, Filed Jun. 12, 2008 (20 pages).

Defendant Cosmetic Alchemy, LLC's Answer to Third Amended Complaint, U.S. District Court, Central District of California (Southern Division), *Allergan, Inc. et al.* v. *Cayman Chemical Company et al.*, Case No. 8:07-cv-01316-JVS-RNB, Document 116, Filed Jul. 2, 2008 (10 pages).

Allergan, Inc. and Murray A. Johnstone, M.D.'s Answer to Amended Counterclaims by Defendant Athena Cosmetics, Inc., U.S. District Court, Central District of California (Southern Division), *Allergan, Inc. et al.* v. *Cayman Chemical Company et al.*, Case No. 8:07-cv-01316-JVS-RNB, Document 118, Filed Jul. 3, 2008 (10 pages).

Response of Procyte Corporation to the Third Amended Complaint, U.S. District Court, Central District of California (Southern Division), *Allergan, Inc. et al.* v. *Cayman Chemical Company et al.*, Case No. 8:07-cv-01316-JVS-RNB, Document 122, Filed Jul. 14, 2008 (5 pages).

Defendant Cayman Chemical Company's Answer and Counterclaim to Third Amended Complaint, U.S. District Court, Central District of California (Southern Division), *Allergan, Inc. et al.* v. *Cayman Chemical Company et al.*, Case No. 8:07-cv-01316-JVS-RNB, Document 126, Filed Jul. 24, 2008 (19 pages).

Joint Claim Construction and Prehearing Statement Under Patent Local Rule 4-3, U.S. District Court, Central District of California (Southern Division), *Allergan, Inc. et al.* v. *Cayman Chemical Company et al.*, Case No. 8:07-cv-01316-JVS-RNB, Document 175, Filed Nov. 13, 2008 (45 pages).

Allergan, Inc. and Murray A. Johnstone, M.D.'s Opening Claim Construction Brief, U.S. District Court, Central District of California (Southern Division), *Allergan, Inc. et al.* v. *Cayman Chemical Company et al.*, Case No. 8:07-cv-01316-JVS-RNB, Document 185, Filed Dec. 15, 2008 (622 pages).

Defendant Athena Cosmetics, Inc.'s Opening Claim Construction Brief, U.S. District Court, Central District of California (Southern Division), *Allergan, Inc. et al.* v. *Cayman Chemical Company et al.*, Case No. 8:07-cv-01316-JVS-RNB, Document 188, Filed Dec. 15, 2008 (84 pages).

Plaintiffs Allergan, Inc. and Murray A. Johnstone, M.D.'s Opening Claim Construction Brief, U.S. District Court, Central District of California (Southern Division), *Allergan, Inc. et al.* v. *Cayman Chemical Company et al.*, Case No. 8:07-cv-01316-JVS-RNb, Document 229, Filed Feb. 13, 2009 (594 pages).

Defendant Athena Cosmetics, Inc.'s Opening Claim Construction Brief, U.S. District Court, Central District of California (Southern Division), *Allergan, Inc. et al.* v. *Cayman Chemical Company et al.*, Case No. 8:07-cv-01316-JVS-RNB, Document 233, Filed Feb. 13, 2009 (135 pages).

Fourth Amended Complaint for Patent Infringement and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 248, Filed Mar. 11, 2009 (54 pages).

Plaintiffs Allergan, Inc. and Murray A. Johnstone, M.D.'s Opposition Claim Construction Brief, U.S. District Court, Central District of California (Southern Division), *Allergan, Inc. et al.* v. *Cayman Chemical Company et al.*, Case No. 8:07-cv-01316-JVS-RNB, Document 252, Filed Mar. 13, 2009 (34 pages).

Amended Answer and Counterclaims of Defendant Athena Cosmetics, Inc. to Plaintiffs Allergan, Inc., and Murray A. Johnstone's Fourth Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 273, Filed Mar. 24, 2009 (26 pages).

Defendant Cosmetic Alchemy, LLC's Answer to Fourth Amended Complaint, U.S. District Court, Central District of California (Southern Division), *Allergan, Inc. et al.* v. *Cayman Chemical Company et al.*, Case No. 8:07-cv-01316-JVS-RNB, Document 275, Filed Mar. 31, 2009 (11 pages).

Plaintiffs Answer to Counterclaims by Defendant Athena Cosmetics, Inc. to Plaintiffs' Fourth Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 280, Filed Apr. 2, 2009 (11 pages).

Answer and Counterclaims of Defendant Pharma Tech International, Inc. to Plaintiffs Allergan, Inc. et al. and Murray A. Johnstone's Fourth Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 290, Filed Apr. 13, 2009 (25 pages).

Plaintiffs' Answer to Counterclaims by Defendant Pharma Tech International, Inc. to Plaintiffs' Fourth Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 291, Filed Apr. 16, 2009 (11 pages).

Answer of Defendants Lifetech Resources LLC and Rocasuba Inc. to Complaint for Patent Infringement, U.S. District Court, Central District of California (Southern Division), *Allergan, Inc. et al.* v. *Cayman Chemical Company et al.*, Case No. 8:07-cv-01316-JVS-RNB, Document 298, Filed May 8, 2009 (13 pages).

Defendant Nutra-Luxe M.D.'s Answer to Complaint for Patent Infringement filed in Case No. SACV09-328-JVS, U.S. District Court, Central District of California (Southern Division), *Allergan, Inc. et al.* v. *Cayman Chemical Company et al.*, Case No. 8:07-cv-01316-JVS-RNB, Document 310, Filed May 26, 2009 (13 pages).

Second Amended Answer and Counterclaims of Defendant Athena Cosmetics, Inc. to Plaintiffs Allergan, Inc., Murray A. Johnstone, and Duke University's Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 328, Filed Jul. 13, 2009 (56 pages).

Supplemental Joint Claim Construction and Prehearing Statement Regarding the '105 and the '404 Patents Under Patent Local Rule 4-3,

(56) References Cited

OTHER PUBLICATIONS

U.S. District Court, Central District of California (Southern Division), *Allergan, Inc. et al.* v. *Cayman Chemical Company et al.*, Case No. 8:07-cv-01316-JVS-RNB, Document 355, Filed Aug. 24, 2009 (17 pages).
Defendants Peter Thomas Roth Labs LLC and Peter Thomas Roth, Inc.'s Answer to Plaintiffs' First Amended Complaint for Patent Infringement, U.S. District Court, Central District of California (Southern Division), *Allergan, Inc. et al.* v. *Cayman Chemical Company et al.*, Case No. 8:07-cv-01316-JVS-RNB, Document 370, Filed Sep. 8, 2009 (15 pages).
Answer of Defendants Lifetech Resources, LLC and Rocasuba, Inc. to First Amended Complaint for Patent Infringement, Violation of California Business and Prfessions Code Section 17200 et seq., and Demand for Jury Trial filed in Case No. SACV09-328-JVS, U.S. District Court, Central District of California (Southern Division), *Allergan, Inc. et al.* v. *Cayman Chemical Company et al.*, Case No. 8:07-cv-01316-JVS-RNB, Document 371, Filed Sep. 8, 2009 (18 pages).
Answer and Counterclaims of Defendant Pharma Tech . Johnstone, and Duke University's First Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 374, Filed Sep. 8, 2009 (21 pages).
Answer and Counterclaims of Defendant Northwest Cosmetic Laboratories, LLC to Plaintiffs Allergan, Inc., Murray A. Johnstone, and Duke University's First Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 376, Filed Sep. 8, 2009 (28 pages).
Answer and Counterclaims of Defendant Athena Cosmetics, Inc. to Plaintiffs Allergan, Inc., Murray A. Johnstone, and Duke University's First Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 377, Filed Sep. 8, 2009 (161 pages).
Lifetech Defendants' Opening Claim Construction Brief, U.S. District Court, Central District of California (Southern Division), *Allergan, Inc. et al.* v. *Cayman Chemical Company et al.*, Case No. 8:07-cv-01316-JVS-RNB, Document 379, Filed Sep. 14, 2009 (24 pages).
Declaration of Elizabeth A. Zidones in Support of Lifetech Defendants' Opening Claim Construction Brief, U.S. District Court, Central District of California (Southern Division), *Allergan, Inc. et al.* v. *Cayman Chemical Company et al.*, Case No. 8:07-cv-01316-JVS-RNB, Document 380, Filed Sep. 14, 2009 (314 pages).
Plaintiffs Allergan, Inc., Murray A. Johnstone, M.D. and Duke University's Supplemental Opening Claim Construction Brief Regarding the '105 and the '404 Patents, U.S. District Court, Central District of California (Southern Division), *Allergan, Inc. et al.* v. *Cayman Chemical Company et al.*, Case No. 8:07-cv-01316-JVS-RNB, Document 381, Filed Sep. 14, 2009 (195 pages).
Defendants Peter Thomas Roth, Inc. and Peter Thomas Roth Labs LLC's Opening Claim Construction Brief, U.S. District Court, Central District of California (Southern Division), *Allergan, Inc. et al.* v. *Cayman Chemical Company et al.*, Case No. 8:07-cv-01316-JVS-RNB, Document 382, Filed Sep. 14, 2009 (22 pages).
Declaration of Dr. Brian M. Stoltz in Support of Ptr Defendants' Opening Claim Construction Brief, U.S. District Court, Central District of California (Southern Division), *Allergan, Inc. et al.* v. *Cayman Chemical Company et al.*, Case No. 8:07-cv-01316-JVS-RNB, Document 383, Filed Sep. 14, 2009 (221 pages).
Declaration of Bryan J. Sinclair in Support of PTR Defendants' Opening Claim Construction Brief, U.S. District Court, Central District of California (Southern Division), *Allergan, Inc. et al.* v. *Cayman Chemical Company et al.*, Case No. 8:07-cv-01316-JVS-RNB, Document 384, Filed Sep. 14, 2009 (31 pages).

Opening Markman Brief of Defendants Metics, LLC; Product Innovations, LLC; and Stella International, LLC, U.S. District Court, Central District of California (Southern Division), *Allergan, Inc. et al.* v. *Cayman Chemical Company et al.*, Case No. 8:07-cv-01316-JVS-RNB, Document 385, Filed Sep. 14, 2009 (11 pages).
Opening Markman Brief/Joinder of Defendant Nutra-Luxe, MD, U.S. District Court, Central District of California (Southern Division), *Allergan, Inc. et al.* v. *Cayman Chemical Company et al.*, Case No. 8:07-cv-01316-JVS-RNB, Document 386, Filed Sep. 14, 2009 (12 pages).
Supplemental Claim Construction Brief of Cosmetics Alchemy, U.S. District Court, Central District of California (Southern Division), *Allergan, Inc. et al.* v. *Cayman Chemical Company et al.*, Case No. 8:07-cv-01316-JVS-RNB, Document 387, Filed Sep. 14, 2009 (33 pages).
Athena Cosmetics, Inc.'s Supplemental Claim Construction Brief Re U.S. Patent No. 6,262,105 and U.S. Patent No. 7,351,404, U.S. District Court, Central District of California (Southern Division), *Allergan, Inc. et al.* v. *Cayman Chemical Company et al.*, Case No. 8:07-cv-01316-JVS-RNB, Document 388, Filed Sep. 14, 2009 (145 pages).
First Amended Answer of Defendants Lifetech Resources, LLC and Recasuba, Inc. to First Amended Complaint for Patent Infringement, Violation of California Business and Professions Code Section 17200 et seq. and Demand for Jury Trial filed in Case No. SACV09-328-JVS, U.S. District Court, Central District of California (Southern Division), *Allergan, Inc. et al.* v. *Cayman Chemical Company et al.*, Case No. 8:07-cv-01316-JVS-RNB, Document 401, filed Sep. 29, 2009 (17 pages).
Defendants Peter Thomas Roth, Inc. and Peter Thomas Roth Labs LLC's First Amended Answer to Plaintiffs' First Amended Complaint for Patent Infringement, U.S. District Court, Central District of California (Southern Division), *Allergan, Inc. et al.* v. *Cayman Chemical Company et al.*, Case No. 8:07-cv-01316-JVS-RNB, Document 405, Filed Oct. 1, 2009 (18 pages).
Amended Answer and Counterclaims of Defendant Northwest Cosmetic Laboratories, LLC to Plaintiffs Allergan, Inc., Murray A. Johnstone, and Duke University's First Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 411, filed Oct. 6, 2009 (34 pages).
First Amended Answer and Counterclaims of Defendant Athena Cosmetics, Inc. to Plaintiffs Allergan, Inc., Murray A. Johnstone, and Duke University's First Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 412, Filed Oct. 6, 2009 (56 pages).
Amended Answer and Counterclaims of Defendant Pharma Tech International, Inc. to Plaintiffs Allergan, Inc., Murray A. Johnstone, and Duke University's First Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 413, Filed Oct. 6, 2009 (22 pages).
First Amended Answer of Defendants Cosmetic Alchemy, LLC; Metics, LLC; Product Innovations, LLC; and Stella International, LLC to Amended Complaint, U.S. District Court, Central District of California (Southern Division), *Allergan, Inc. et al.* v. *Cayman Chemical Company et al.*, Case No. 8:07-cv-01316-JVS-RNB, Document 416, Filed Oct. 9, 2009 (14 pages).
First Amended Answer of Defendant Nutra-Luxe MD to Amended Complaint, U.S. District Court, Central District of California (Southern Division), *Allergan, Inc. et al.* v. *Cayman Chemical Company et al.*, Case No. 8:07-cv-01316-JVS-RNB, Document 417, Filed Oct. 9, 2009 (16 pages).
Plaintiffs Allergan, Inc. and Murray A. Johnstone, M.D.'s Reply Claim Construction Brief Regarding the '105 and the '404 Patents, U.S. District Court, Central District of California (Southern Division), *Allergan, Inc.* et al. v. *Cayman Chemical Company* et al., Case No. 8:07-cv-01316-JVS-RNB, Document 418, Filed Oct. 13, 2009 (290 pages).

(56) References Cited

OTHER PUBLICATIONS

Defendants Peter Thomas Roth, Inc. and Peter Thomas Roth Labs LLC's Reply Claim Construction Brief, U.S. District Court, Central District of California (Southern Division), *Allergan, Inc. et al.* v. *Cayman Chemical Company et al.*, Case No. 8:07-cv-01316-JVS-RNB, Document 419, Filed Oct. 13, 2009 (15 pages).
Lifetech Defendants' Reply Brief in Opposition to Plaintiffs' Opening and Supplemental Claim Construction Briefs, U.S. District Court, Central District of California (Southern Division), *Allergan, Inc. et al.* v. *Cayman Chemical Company et al.*, Case No. 8:07-cv-01316-JVS-RNB, Document 423, Filed Oct. 13, 2009 (32 pages).
Declaration of Ryan J. Fletcher in Support of Lifetech Defendants' Brief in Opposition to Plaintiffs' Opening and Supplemental Claim Construction Briefs, U.S. District Court, Central District of California (Southern Division), *Allergan, Inc. et al.* v. *Cayman Chemical Company et al.*, Case No. 8:07-cv-01316-JVS-RNB, Document 424, Filed Oct. 13, 2009 (59 pages).
Plaintiffs' Answer to Counterclaims by Northwest Cosmetic Laboratories, LLC to Plaintiffs' First Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 432, Filed Oct. 23, 2009 (8 pages).
Plaintiffs' Answer to Counterclaims by Pharma Tech International, Inc. to Plaintiffs' First Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 433, Filed Oct. 23, 2009 (6 pages).
Plaintiffs' Answer to Counterclaims by Defendant Athena Cosmetics, Inc. To Plaintiffs' First Amended Complaint and Demand for Jury Trial, U.S. District Court, Central District of California (Southern Division), *Allergan, Inc. et al.* v. *Cayman Chemical Company et al.*, Case No. 8:07-cv-01316-JVS-RNB, Document 434, Filed Oct. 23, 2009 (21 pages).
Joint Claim Construction and Prehearing Statement Regarding U.S. Pat. No. 7,388,029 Under Patent Local Rule 43, U.S. District Court, Central District of California (Southern Division), *Allergan, Inc. et al.* v. *Cayman Chemical Company et al.*, Case No. 8:07-cv-01316-JVS-RNB, Document 435, Filed Oct. 23, 2009 (4 pages).
Second Amended Answer of Defendant Nutra-Luxe MD to Amended Complaint, U.S. District Court, Central District of California (Southern Division), *Allergan, Inc. et al.* v. *Cayman Chemical Company et al.*, Case No. 8:07-cv-01316-JVS-RNB, Document 439, Filed Oct. 30, 2009 (17 pages).
Second Amended Answer of Defendants Cosmetic Alchemy, LLC; Metics, LLC; Product Innovations, LLC; and Stella International, LLC to Amended Complaint, U.S. District Court, Central District of California (Southern Division), *Allergan, Inc. et al.* v. *Cayman Chemical Company et al.*, Case No. 8:07-cv-01316-JVS-RNB, Document Filed Oct. 30, 2009 (14 pages).
Second Amended Answer of Defendants Lifetech Resources, LLC and Recasuba, Inc. To First Amended Complaint for Patent Infringement, Violation of California Business and Professions Code Section 17200 et seq. and Demand for Jury Trial Filed in Case No. SACV09-328-JVS, U.S. District Court, Central District of California (Southern Division), *Allergan, Inc. et al.* v. *Cayman Chemical Company et al.*, Case No. 8:07-cv-01316-JVS-RNB, Document Filed Oct. 30, 2009 (18 pages).
Minutes of Markman/Claim Construction Hearing, U.S. District Court, Central District of California (Southern Division), *Allergan, Inc. et al.* v. *Cayman Chemical Company et al.*, Case No. 8:07-cv-01316-JVS-RNB, Document Filed Oct. 26, 2009 (1 page).
Minutes of in Chambers Final Order re Claim Construction, U.S. District Court, Central District of California (Southern Division), *Allergan, Inc. et al.* v. *Cayman Chemical Company et al.*, Case No. 8:07-cv-01316-JVS-RNB, Document 446, Filed Nov. 16, 2009 (49 pages).
Stipulation for Defendants Cosmetic Alchemy, LLC; Metics, LLC; Product Innovations, LLC; Stella International, LLC; and Nutra-Luxe MD to Amend Their Second Amended Answers to Plaintiffs' First Amended Complaint, U.S. District Court, Central District of California (Southern Division), *Allergan, Inc. et al.* v. *Cayman Chemical Company et al.*, Case No. 8:07-cv-01316-JVS-RNB, Document 448, Filed Dec. 7, 2009 (3 pages).
Third Amended Answer of Defendant Nutra-Luxe Md to Amended Complaint, U.S. District Court, Central District of California (Southern Division), *Allergan, Inc. et al.* v. *Cayman Chemical Company et al.*, Case No. 8:07-cv-01316-JVS-RNB, Document 449, Filed Dec. 7, 2009 (17 pages).
Third Amended Answer of Defendants Cosmetic Alchemy, LLC; Metics, LLC; Product Innovations, LLC; and Stella International, LLC to Amended Complaint, U.S. District Court, Central District of California (Southern Division), *Allergan, Inc. et al.* v. *Cayman Chemical Company et al.*, Case No. 8:07-cv-01316-JVS-RNB, Document 450, Filed Dec. 7, 2009 (15 pages).
Plaintiffs Allergan, Inc. and Duke University's Opening Claim Construction Brief Regarding U.S. Patent No. 7,388,029, U.S. District Court, Central District of California (Southern Division), *Allergan, Inc. et al.* v. *Cayman Chemical Company et al.*, Case No. 8:07-cv-01316-JVS-RNB, Document 451, Filed Dec. 7, 2009 (241 pages).
Athena Cosmetics, Inc., Pharma Tech International, Inc. and Northwest Cosmetic Laboratories, LLC's Opening Claim Construction Brief Ref U.S. Patent No. 7,388,029, U.S. District Court, Central District of California (Southern Division), *Allergan, Inc. et al.* v. *Cayman Chemical Company et al.*, Case No. 8:07-cv-01316-JVS-RNB, Document 452, Filed Dec. 7, 2009 (213 pages).
Plaintiffs' Allergan, Inc. and Duke University's Reply Claim Construction Brief Regarding U.S. Patent No. 7,388,029, U.S. District Court, Central District of California (Southern Division), *Allergan, Inc. et al.* v. *Cayman Chemical Company et al.*, Case No. 8:07-cv-01316-JVS-RNB, Document 454, Filed Dec. 21, 2009 (72 pages).
Athena Cosmetics, Inc., Pharma Tech International, Inc. and Northwest Cosmetic Laboratories, LLC's Reply Claim Construction Brief Re U.S. Patent No. 7,388,029, U.S. District Court, Central District of California (Southern Division), *Allergan, Inc. et al.* v. *Cayman Chemical Company et al.*, Case No. 8:07-cv-01316-JVS-RNB, Document 455, Filed Dec. 21, 2009 (24 pages).
Minutes from Markman/Claim Construction Hearing on the '029 Patent, U.S. District Court, Central District of California (Southern Division), *Allergan, Inc. et al.* v. *Cayman Chemical Company et al.*, Case No. 8:07-cv-01316-JVS-RNB, Document 462, Filed Jan. 11, 2010 (1 page).
Minutes in Chambers Order re Claim Construction on the '029 Patent, U.S. District Court, Central District of California (Southern Division), *Allergan, Inc. et al.* v. *Cayman Chemical Company et al.*, Case No. 8:07-cv-01316-JVS-RNB, Document 463, Filed Jan. 12, 2010 (16 pages).
Order Entering Final Judgment Pursuant to Federal Rule of Civil Procedure 54(b) on Plaintiff Allergan, Inc.'s Fourth Claim for Relief in Favor of Defendants and Stay of Trial Court Proceedings Pending Appeal, U.S. District Court, Central District of California (Southern Division), *Allergan, Inc. et al.* v. *Cayman Chemical Company et al.*, Case No. 8:07-cv-01316-JVS-RNB, Document 526, filed May 5, 2010 (2 pages).
Defendants' Invalidity Contentions Pursuant to Patent Local Rule 3-3, U.S. District Court, Central District of California (Southern Division), *Allergan, Inc. et al.* v. *Cayman Chemical Company et al.*, Case No. 8:07-cv-01316-JVS-RNB, dated Sep. 22, 2008 (315 pages).
Defendants Athena Cosmetics, Inc., Pharma Tech International, Inc., and Northwest Cosmetic Laboratories, Inc.'s Preliminary Invalidity Contentions Pursuant to Patent Local Rule 3-3, U.S. District Court, Central District of California (Southern Division), *Allergan, Inc. et al.* v. *Cayman Chemical Company et al.*, Case No. 8:07-cv-01316-JVS-RNB, dated Aug. 24, 2009 (102 pages).
Defendant Athena Cosmetics, Inc.'s Supplemental Invalidity Contentions Pursuant to Patent Local Rule 3-3, U.S. District Court, Central District of California (Southern Division), *Allergan, Inc. et al.* v. *Cayman Chemical Company et al.*, Case No. 8:07-cv-01316-JVS-RNB, dated Feb. 9, 2009 (38 pages).
Defendant Athena Cosmetics, Inc.'s Supplemental Invalidity Contentions Pursuant to Patent Local Rule 3-3, U.S. District Court, Central District of California (Southern Division), *Allergan, Inc. et*

(56) References Cited

OTHER PUBLICATIONS al. v. *Cayman Chemical Company et al.*, Case No. 8:07-cv-01316-JVS-RNB, dated Feb. 20, 2009 (320 pages).
Plaintiffs' Responses to Athena Cosmetics, Inc.'s Second Set of Interrogatories (Nos. 3-7), U.S. District Court, Central District of California (Southern Division), *Allergan, Inc. et al. v. Cayman Chemical Company et al.*, Case No. 8:07-cv-01316-JVS-RNB, dated Feb. 1, 2010 (14 pages).
Defendants Athena Cosmetics, Inc., PharmaTech International, Inc., and Northwest Cosmetic Laboratories, Inc.'s Supplemental Invalidity Contentions Pursuant to Northern District Patent Local Rules 3-3 and 3-7, U.S. District Court, Central District of California (Southern Division), *Allergan, Inc. et al. v. Cayman Chemical Company et al.*, Case No. 8:07-cv-01316-JVS-RNB, dated Mar. 18, 2010 (25 pages).
Brief of Defendant-Appellants Apotex Inc., Apotex Corp., Sandoz, Inc., and Hi-Tech Pharmacal Co., Inc. in the United States Court of Appeals for the Federal Circuit, Case No. 2013-1245, -1246, -1247, filed May 13, 2013 (198 pages).
Appellees' Responsive Brief in the United States Court of Appeals for the Federal Circuit, Case No. 2013-1245, -1246, -1247, filed Jul. 29, 2013 (80 pages).
B. W. Griffin et al., FP Prostaglandin Receptors Mediating Inositol Phosphates Generation and Calcium Mobilization in Swiss 3T3 Cells: A Pharmacological Study, J. Pharmacol. Exp. Ther. (1997) 281(2):845-854.
C.S. Harmon et al., Protein Kinase C Inhibits Human Hair Follicle Growth and Hair Fibre Production in Organ Culture, Br. J. Derm. (1995) 133:686-693.
Carl B. Camras, Mechanism of the Prostaglandin-Induced Reduction of Intraocular Pressure in Humans, in Advances in Prostaglandin, Thromboxane, and Leukotriene Res. 519-525 (B. Samuelsson et al., eds., vol. 23, 1995).
Charles Mark Ensor and Hsin-Hsiung Tai, 15-Hydroxyprostaglandin Dehydrogenase, J. Lipid Mediators Cell Signalling (1995) 12: 313-319.
Gerald R. Zins, The History of the Development of Minoxidil, Clinics in Derm. (1988) 6(4):132-147.
Gerd Linder et al., Involvement of Hepatocyte Growth Factor/Scatter Factor and Met Receptor Signaling in Hair Follicle Morphogenesis and Cycling, 14 FASEB J. 313-319 (2000).
Hiroyuki Toh et al., Molecular Evolution of Receptors for Eicosanoids, 361 Fed. Eur. Biochem. Soc. 17:21 (1995).
International Publication No. WO 92/02496 (Feb. 20, 1992).
J. Chen et al., AGN 191129: A Neutral Prostaglandin F2α (PGF2α) Analog That Lacks the Mitogenic and Uterotonic Effects Typical of FP Receptor Agonists, 40 IOVS S675 (Abstract 3562-B420) (1999).
J.L.Burton & A. Marshall, Hypertrichosis Due to Minoxidil, 101 Br. J. Derm. 593-595 (1979).
J.W. Regan et al., Cloning of a Novel Human Prostaglandin Receptor with Characteristics of the Pharmacologically Defined EP2 Subtype, 46 Molecular Pharm. 213-220 (1994).

James P. Bennett, Jr., Methods in Binding Studies, in Neurotransmitter Receptor Binding, (H.I. Yamamura et al., eds., 1978) 57-90.
Jonathan Hadgraft, Prodrugs and Skin Absorption, in Design of Prodrugs (H. Bungaard ed., 1985) 271-289.
K.S. Stenn & R. Paus, Controls of Hair Follicle Cycling, 81 Physiol. Rev. 449 (Jan. 2001).
L.E. Anderson et al., Prostaglandin Moieties that Determine Receptor Binding Specificity in the Bovine Corpus Lutem, 116 J. Reproduction Fertility 133-141 (1999).
Laszlo Z. Bito, Prostaglandins: A New Approach to Glaucoma Management with a New, Intriguing Side Effect, 41(2):S1-14 Sur. Ophthalmol. (1997).
Marianne Nelson O'Donoghue, Eye Cosmetics, 18 Derm. Aspects Cosmetics 633-639 (2000).
Masayuki Nakajima et al., Effects of Prostaglandin D2 and its Analogue, BW245C, on Intraocular Pressure in Humans, 229 Graefe'S Arch. Clin. Exp. Ophthalmol. 411-413 (1991).
Michael R. Goldberg, Clinical Pharmacology of Pinacidil, A Protype for Drugs That Affect Potassium Channels, 12(Supp 2):541-547 J. Cardio. Pharm. (1988).
Per J. Wistrand et al., The Incidence and Time-Course of Latanoprost-Induced Iridial Pigmentation as a Function of Eye Color, 41(2):S129-138 Sur. Ophthalmol.(1997).
Peter J. Koblenzer & Lester Baker, Hypertrichosis Lanuginosa Associated with Diazoxide Therapy in Prepubertal Children: A Clinicopathologic Study, 150 Annals NY Acad. Sci. 373-382 (1968).
Richard B. Silverman, Drug Metabolism, in The Organic Chemisty of Drug Design and Drug Action 277 (1992).
Richard B. Silverman, Prodrugs and Drug Delivery Systems, in the Organic Chemisty of Drug Design and Drug Action 352 (1992) 352-401.
Richard A. F. Dixon et al., Cloning of the Gene and cDNA for Mammalian β-Adrenergic Receptor and Homology with Rhodopsin, 321 Nature 75-79 (1986).
Shuh Narumiya et al., Prostanoid Receptors: Structures, Properties, and Functions, 79 Physiol. Rev. (1999) 1193-1226.
Yasumasa Goh et al., Prostaglandin D2 Reduces Intraocular Pressure, 72 Br. J. Ophthalmol. 461-464 (1988).
Yukihiko Sugimoto et al, Failure of Parturtion in Mice Lacking the Prostaglandin F Receptor, 277 Science 681-683 (1997).
Khidhir, K.G. et al., "The prostamide-related glaucoma therapy, bimatoprost, offers a novel approach for treating scalp alopecias," The FASEB J. (2013) 27:11p.
Opinion of the United States Court of Appeals for the Federal Circuit, *Allergan, Inc. et al. v. Apotex Inc. et al.*, Case No. 13-1245, decided Jun. 10, 2014 (41 pages).
Notice of Entry of Judgment of the United States Court of Appeals for the Federal Circuit, *Allergan, Inc. et al. v. Apotex Inc. et al.*, Case No. 13-1245, decided Jun. 10, 2014 (1 page).
Corrected Combined Petition of Plaintiffs-Appellees Allergan, Inc. And Duke University for Panel or Enbanc Rehearing, United States Court of Appeals of the Federal Circuit, *Allergan, Inc. et al. v. Apotex Inc. et al.*, Case No. 13-1245, filed Aug. 12, 2014 (62 pages).
Joint Status Report in the United States District Court for the Middle District of North Carolina, *Allergan, Inc. et al. v. Apotex Inc. et al.*, Case No. 1:10-CV-681 dated Jul. 21, 2014 (13 pages).

COMPOSITIONS AND METHODS FOR TREATING HAIR LOSS USING NON-NATURALLY OCCURRING PROSTAGLANDINS

This application is a continuation of U.S. patent application Ser. No. 12/535,513, filed Aug. 4, 2009, which is a continuation of U.S. patent application Ser. No. 11/967,423, filed Dec. 31, 2007, now abandoned, which is a continuation of U.S. patent application Ser. No. 11/138,097, filed May 26, 2005, now U.S. Pat. No. 7,388,029, which is a divisional of U.S. patent Ser. No. 09/774,557, filed Jan. 31, 2001, now abandoned, which claims priority to U.S. Provisional Application No. 60/193,645, filed Mar. 31, 2000, all of which are incorporated hereby by reference in their entirety.

FIELD OF THE INVENTION

This invention relates to compositions and methods for treating hair loss in mammals. More particularly, this invention relates to compositions and methods for arresting or reversing hair loss, or both, and promoting hair growth.

BACKGROUND OF THE INVENTION

Hair loss is a common problem which is, for example, naturally occurring or chemically promoted through the use of certain therapeutic drugs designed to alleviate conditions such as cancer. Often such hair loss is accompanied by lack of hair re-growth which causes partial or full baldness.

Hair growth on the scalp does not occur continuously, but rather occurs by a cycle of activity involving alternating periods of growth and rest. This cycle is divided into three main stages; anagen, catagen, and telogen. Anagen is the growth phase of the cycle and is characterized by penetration of the hair follicle deep into the dermis with rapid proliferation of cells which are differentiating to form hair. The next phase is catagen, which is a transitional stage marked by the cessation of cell division, and during which the hair follicle regresses through the dermis and hair growth ceases. The next phase, telogen, is characterized as the resting stage during which the regressed follicle contains a germ with tightly packed dermal papilla cells. At telogen, the initiation of a new anagen phase is caused by rapid cell proliferation in the germ, expansion of the dermal papilla, and elaboration of basement membrane components. When hair growth ceases, most of the hair follicles reside in telogen and anagen is not engaged, thus causing the onset of full or partial baldness.

Attempts to invoke the re-growth of hair have been made by, for example, the promotion or prolongation of anagen. Currently, there are two drugs approved by the United States Food and Drug Administration for the treatment of male pattern baldness: topical minoxidil (marketed as ROGAINE® by Pharmacia & Upjohn), and oral finasteride (marketed as PROPECIA® by Merck & Co., Inc.). However, the search for efficacious hair growth inducers is ongoing due to factors including safety concerns and limited efficacy.

The thyroid hormone thyroxine ("T4") converts to thyronine ("T3") in human skin by deiodinase I, a selenoprotein. Selenium deficiency causes a decrease in T3 levels due to a decrease in deiodinase I activity; this reduction in T3 levels is strongly associated with hair loss. Consistent with this observation, hair growth is a reported side effect of administration of T4. See, e.g., Berman, "Peripheral Effects of L-Thyroxine on Hair Growth and Coloration in Cattle", *Journal of Endocrinology*, Vol. 20, pp. 282-292 (1960); and Gunaratnam, "The Effects of Thyroxine on Hair Growth in the Dog", *J. Small Anim. Pract.*, Vol. 27, pp. 17-29 (1986). Furthermore, T3 and T4 have been the subject of several patent publications relating to treatment of hair loss. See, e.g., Fischer et al., DE 1,617,477, published Jan. 8, 1970; Mortimer, GB 2,138,286, published Oct. 24, 1984; and Lindenbaum, WO 96/25943, assigned to Life Medical Sciences, Inc., published Aug. 29, 1996.

Unfortunately, however, administration of T3 or T4, or both, to treat hair loss is often not practicable because these thyroid hormones can induce significant cardiotoxicity. See, e.g., Walker et al., U.S. Pat. No. 5,284,971, assigned to Syntex, issued Feb. 8, 1994 and Emmett et al., U.S. Pat. No. 5,061,798, assigned to Smith Kline & French Laboratories, issued Oct. 29, 1991.

In an alternative approach, prostaglandins have been proposed to promote hair growth because prostaglandins may have a similar benefit to thyroid hormones, i.e., increasing hair length and changing pigmentation. Naturally occurring prostaglandins (e.g., $PGA_2$, $PGB_2$, $PGE_1$, $PGF_{2\alpha}$, and $PGI_2$) are C-20 unsaturated fatty acids. $PGF_{2\alpha}$, the naturally occurring Prostaglandin F analog in humans, is characterized by hydroxyl groups at the C9 and C11 positions on the alicyclic ring, a cis-double bond between C5 and C6, and a trans-double bond between C13 and C14. $PGF_{2\alpha}$ has the formula:

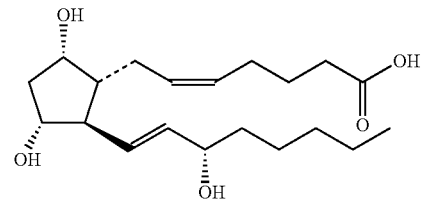 [SMILES: CCCCC[C@H](O)/C=C/[C@@H]1[C@@H](C/C=C\CCCC(=O)O)[C@@H](O)C[C@H]1O]

Analogs of naturally occurring Prostaglandin F are known in the art. For example, see U.S. Pat. No. 4,024,179 issued to Bindra and Johnson on May 17, 1977; German Patent No. DT-002,460,990 issued to Beck, Lerch, Seeger, and Teufel published on Jul. 1, 1976; U.S. Pat. No. 4,128,720 issued to Hayashi, Kori, and Miyake on Dec. 5, 1978; U.S. Pat. No. 4,011,262 issued to Hess, Johnson, Bindra, and Schaaf on Mar. 8, 1977; U.S. Pat. No. 3,776,938 issued to Bergstrom and Sjovall on Dec. 4, 1973; P. W. Collins and S. W. Djuric, "Synthesis of Therapeutically Useful Prostaglandin and Prostacyclin Analogs", *Chem. Rev.*, Vol. 93, pp. 1533-1564 (1993); G. L. Bundy and F. H. Lincoln, "Synthesis of 17-Phenyl-18,19,20-Trinorprostaglandins: I. The $PG_1$ Series", *Prostaglandin*, Vol. 9 No. 1, pp. 1-4 (1975); W. Bartman, G. Beck, U. Lerch, H. Teufel, and B. Scholkens, "Luteolytic Prostaglandin: Synthesis and Biological Activity", *Prostaglandin*, Vol. 17 No. 2, pp. 301-311 (1979); C. Iiljebris, G. Selen, B. Resul, J. Sternschantz, and U. Hacksell, "Derivatives of 17-Phenyl-18,19,20-trinorprostaglandin $F_{2\alpha}$. Isopropyl Ester: Potential Antiglaucoma Agents", *Journal of Medicinal Chemistry*, Vol. 38, No. 2, pp. 289-304 (1995).

Prostaglandins in general have a wide range of biological activities. For example, $PGE_2$ has the following properties: a) regulator of cell proliferation, b) regulator of cytokine synthesis, c) regulator of immune responses and d) inducer of vasodilatation. Vasodilatation is thought to be one of the mechanisms of how minoxidil provides a hair growth benefit. In vitro results in the literature also indicate some anti-inflammatory properties of the prostaglandins. c.f.; Tanaka, H. *Br J. Pharm.*, 116, 2298, (1995).

However, previous attempts at using prostaglandins to promote hair growth have been unsuccessful. Different prostaglandin analogs can bind to multiple receptors at various concentrations with a biphasic effect. Furthermore, administration of naturally occurring prostaglandins can cause side effects such as inflammation, surface irritation, smooth muscle contraction, pain, and bronchoconstriction. Therefore, it is an object of this invention to provide methods for using prostaglandin analogs to grow hair and to provide compositions that promote hair growth in humans and lower animals. It is a further object of this invention to provide a selection of appropriate prostaglandin analogs that will promote hair growth and that do not cause significant undesirable side effects.

SUMMARY OF THE INVENTION

This invention relates to compositions and methods for treating hair loss. The methods comprise administering the compositions comprising specific prostaglandin analogs that interact strongly with hair-selective receptors, such as the FP receptor. The choice of prostaglandin analog is important because the prostaglandin analogs must selectively activate the FP receptor and not activate any other receptors that would negate the effect of activating the FP receptor. The compositions comprise: component A) the prostaglandin analog, component B) a carrier, and optionally component C) an activity enhancer.

DETAILED DESCRIPTION OF THE INVENTION

This invention relates to compositions and methods using prostaglandin F analogs ("PGF's") to treat hair loss in mammals. "Treating hair loss" includes arresting hair loss or reversing hair loss, or both, and promoting hair growth.

Publications and patents are referred to throughout this disclosure. All U.S. Patents cited herein are hereby incorporated by reference.

All percentages, ratios, and proportions used herein are by weight unless otherwise specified.

DEFINITION AND USAGE OF TERMS

The following is a list of definitions for terms, as used herein:

"Activate" means binding and signal transduction of a receptor.

"Acyl group" means a monovalent group suitable for acylating a nitrogen atom to form an amide or carbamate, an alcohol to form a carbonate, or an oxygen atom to form an ester group. Preferred acyl groups include benzoyl, acetyl, tert-butyl acetyl, para-phenyl benzoyl, and trifluoroacetyl. More preferred acyl groups include acetyl and benzoyl. The most preferred acyl group is acetyl.

"Aromatic group" means a monovalent group having a monocyclic ring structure or fused bicyclic ring structure. Monocyclic aromatic groups contain 5 to 10 carbon atoms, preferably 5 to 7 carbon atoms, and more preferably 5 to 6 carbon atoms in the ring. Bicyclic aromatic groups contain 8 to 12 carbon atoms, preferably 9 or 10 carbon atoms in the ring. Aromatic groups are unsubstituted. The most preferred aromatic group is phenyl. Bicyclic aromatic groups include ring systems wherein one ring in the system is aromatic. Preferred bicyclic aromatic groups are ring systems wherein both rings in the system are aromatic. Preferred aromatic rings include naphthyl and phenyl. The most preferred aromatic ring is phenyl.

"Carbocyclic group" means a monovalent saturated or unsaturated hydrocarbon ring. Carbocyclic groups are monocyclic. Carbocyclic groups contain 4 to 10 carbon atoms, preferably 4 to 7 carbon atoms, and more preferably 5 to 6 carbon atoms in the ring. Carbocyclic groups are unsubstituted. Preferred carbocyclic groups include cyclopentyl, cyclohexyl, cyclohexenyl, cycloheptyl, and cyclooctyl. More preferred carbocyclic groups include cyclohexyl, cycloheptyl, and cyclooctyl. The most preferred carbocyclic group is cycloheptyl. Carbocyclic groups are not aromatic.

"FP agonist" means a compound that activates the FP receptor.

"FP receptor" means known human FP receptors, their splice variants, and undescribed receptors that have similar binding and activation profiles as the known human FP receptors. "FP" means the receptor is of the class which has the highest affinity for $PGF_{2\alpha}$ of all the naturally occurring prostaglandins. FP refers to a known protein.

"Halogen atom" means F, Cl, Br, or I. Preferably, the halogen atom is F, Cl, or Br; more preferably Cl or F; and most preferably F.

"Halogenated heterogenous group" means a substituted heterogenous group or a substituted heterocyclic group, wherein at least one substituent is a halogen atom. Halogenated heterogenous groups can have a straight, branched, or cyclic structure. Preferred halogenated heterogenous groups have 1 to 12 carbon atoms, more preferably 1 to 6 carbon atoms, and most preferably 1 to 3 carbon atoms. Preferred halogen atom substituents are Cl and F.

"Halogenated hydrocarbon group" means a substituted monovalent hydrocarbon group or a substituted carbocyclic group, wherein at least one substituent is a halogen atom. Halogenated hydrocarbon groups can have a straight, branched, or cyclic structure. Preferred halogenated hydrocarbon groups have 1 to 12 carbon atoms, more preferably 1 to 6 carbon atoms, and most preferably 1 to 3 carbon atoms. Preferred halogen atom substituents are Cl and F. The most preferred halogenated hydrocarbon group is trifluoromethyl.

"Heteroaromatic group" means an aromatic ring containing carbon and 1 to 4 heteroatoms in the ring. Heteroaromatic groups are monocyclic or fused bicyclic rings. Monocyclic heteroaromatic groups contain 5 to 10 member atoms (i.e., carbon and heteroatoms), preferably 5 to 7, and more preferably 5 to 6 in the ring. Bicyclic heteroaromatic rings contain 8 to 12 member atoms, preferably 9 or 10 in the ring. Heteroaromatic groups are unsubstituted. Bicyclic heteroaromatic groups include ring systems in which only one ring is aromatic. Preferred bicyclic heteroaromatic groups are ring systems in which both rings are aromatic. Preferred monocyclic heteroaromatic groups include thienyl, thiazolyl, purinyl, pyrimidyl, pyridyl, and furanyl. More preferred monocyclic heteroaromatic groups include thienyl, furanyl, and pyridyl. The most preferred monocyclic heteroaromatic group is thienyl. Preferred bicyclic heteroaromatic rings include benzothiazolyl, benzothiophenyl, quinolinyl, quinoxalinyl, benzofuranyl, benzimidazolyl, benzoxazolyl, indolyl, and anthranilyl. More preferred bicyclic heteroaromatic rings include benzothiazolyl, benzothiophenyl, and benzoxazolyl.

"Heteroatom" means an atom other than carbon in the ring of a heterocyclic group or the chain of a heterogeneous group. Preferably, heteroatoms are selected from the group consisting of nitrogen, sulfur, and oxygen atoms. Groups containing more than one heteroatom may contain different heteroatoms.

"Heterocyclic group" means a saturated or unsaturated ring structure containing carbon and 1 to 4 heteroatoms in the ring. No two heteroatoms are adjacent in the ring, and no carbon in the ring that has a heteroatom bonded to it also has a hydroxyl, amino, or thiol group bonded to it. Heterocyclic groups are not aromatic. Heterocyclic groups are monocyclic.

Heterocyclic groups contain 4 to 10 member atoms (i.e., including both carbon atoms and at least 1 heteroatom), preferably 4 to 7, and more preferably 5 to 6 in the ring. Heterocyclic groups are unsubstituted. Preferred heterocyclic groups include piperzyl, morpholinyl, tetrahydrofuranyl, tetrahydropyranyl, and piperdyl.

"Heterogeneous group" means a saturated or unsaturated chain containing 1 to 18 member atoms (i.e., including both carbon and at least one heteroatom). No two heteroatoms are adjacent. Preferably, the chain contains 1 to 12 member atoms, more preferably 1 to 6. "Lower heterogeneous" means a heterogeneous group having 1 to 6, preferably 1 to 3, member atoms. The chain may be straight or branched. Preferred branched heterogeneous groups have one or two branches, preferably one branch. Preferred heterogeneous groups are saturated. Unsaturated heterogeneous groups have one or more double bonds, one or more triple bonds, or both. Preferred unsaturated heterogeneous groups have one or two double bonds or one triple bond. More preferably, the unsaturated heterogeneous group has one double bond. Heterogeneous groups are unsubstituted.

"Monovalent hydrocarbon group" means a chain of 1 to 18, preferably 1 to 12, carbon atoms. "Lower monovalent hydrocarbon group" means a monovalent hydrocarbon group having 1 to 6, preferably 1 to 3, carbon atoms. Monovalent hydrocarbon groups may have a straight chain or branched chain structure. Preferred monovalent hydrocarbon groups have one or two branches, preferably 1 branch. Preferred monovalent hydrocarbon groups are saturated. Unsaturated monovalent hydrocarbon groups have one or more double bonds, one or more triple bonds, or combinations thereof. Preferred unsaturated monovalent hydrocarbon groups have one or two double bonds or one triple bond; more preferred unsaturated monovalent hydrocarbon groups have one double bond.

"Pharmaceutically acceptable" means suitable for use in a human or other mammal.

"Prostaglandin" means a fatty acid derivative which has a variety of potent biological activities of a hormonal or regulatory nature.

"Protecting group" is a group that replaces the active hydrogen of a hydroxyl moiety thus preventing undesired side reaction at the hydroxyl moiety. Use of protecting groups in organic synthesis is well known in the art. Examples of protecting groups are found in Chapter 2 *Protecting Groups in Organic Synthesis* by Greene, T. W. and Wuts, P. G. M., $2^{nd}$ ed., Wiley & Sons, Inc., 1991. Preferred protecting groups include silyl ethers, alkoxymethyl ethers, tetrahydropyranyl, tetrahydrofuranyl, esters, and substituted or unsubstituted benzyl ethers.

"Safe and effective amount" means a quantity of a prostaglandin high enough to provide a significant positive modification of the subject's condition to be treated, but low enough to avoid serious side effects (at a reasonable benefit/risk ratio).

"Selective" means having a binding or activation preference for a specific receptor over other receptors which can be quantitated based upon receptor binding or activation assays.

"Subject" means a living, vertebrate, hair- or fur-bearing animal such as a mammal (preferably human) in need of treatment.

"Substituted aromatic group" means an aromatic group wherein 1 to 4 of the hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, substituted heterogeneous groups, aromatic groups, substituted aromatic groups, or any combination thereof. More preferred substituents include halogen atoms, halogenated monovalent hydrocarbon groups, phenyl groups, and phenoxy groups. Preferred substituted aromatic groups include naphthyl. The substituents may be substituted at the ortho, meta, or para position on the ring, or any combination thereof. The preferred substitution pattern on the ring is ortho or meta. The most preferred substitution pattern is ortho.

"Substituted carbocyclic group" means a carbocyclic group wherein 1 to 4 hydrogen atoms bonded to carbon atoms in the ring have been replaced with other substituents. Preferred substituents include: halogen atoms, cyano groups, monovalent hydrocarbon groups, monovalent heterogeneous groups, substituted monovalent hydrocarbon groups, substituted heterogeneous groups, aromatic groups, substituted aromatic groups, or any combination thereof. More preferred substituents include halogen atoms, halogenated monovalent hydrocarbon groups, phenyl groups, and phenoxy groups.

"Substituted heteroaromatic group" means a heteroaromatic group wherein 1 to 4 hydrogen atoms bonded to carbon atoms in the ring have been replaced with other substituents. The substituents include halogen atoms, acyl groups, cyano groups, monovalent hydrocarbon groups, substituted monovalent hydrocarbon groups, heterogeneous groups, substituted heterogeneous groups, aromatic groups, substituted aromatic groups, heteroaromatic groups, substituted heteroaromatic groups, and any combination thereof. Preferred substituents include halogen atoms, cyano groups, monovalent hydrocarbon groups, substituted monovalent hydrocarbon groups, heterogeneous groups, substituted heterogeneous groups, phenyl groups, phenoxy groups, or any combination thereof. More preferred substituents include halogen atoms, halogenated hydrocarbon groups, monovalent hydrocarbon groups, halogenated heterogenous groups, and phenyl groups.

"Substituted heterocyclic group" means a heterocyclic group wherein 1 to 4 hydrogen atoms bonded to carbon atoms in the ring have been replaced with other substituents. Preferred substituents include: halogen atoms, cyano groups, monovalent hydrocarbon groups, substituted monovalent hydrocarbon groups, heterogeneous groups, substituted heterogeneous groups, aromatic groups, substituted aromatic groups, or any combination thereof. More preferred substituents include halogen atoms, halogenated hydrocarbon groups, phenyl groups, phenoxy groups, or any combination thereof. Substituted heterocyclic groups are not aromatic.

"Substituted heterogeneous group" means a heterogeneous group, wherein 1 to 4 of the hydrogen atoms bonded to carbon atoms in the chain have been replaced with other substituents. Preferably substituted heterogeneous groups are mono, di, or trisubstituted. Preferred substituents include halogen atoms, hydroxy groups, carboxy groups, aryloxy groups (e.g., phenoxy, chlorophenoxy, tolyloxy, methoxyphenoxy, benzyloxy, alkyloxycarbonylphenoxy, and acyloxyphenoxy), acyloxy groups (e.g., propionyloxy, benzoyloxy, and acetoxy), aromatic groups (e.g., phenyl and tolyl), substituted aromatic groups (e.g., alkoxyphenyl, alkoxycarbonylphenyl, and halophenyl), heterocyclic groups, heteroaromatic groups, substituted heterocyclic groups, and amino groups (e.g., amino, mono- and di-alkylamino having 1 to 3 carbon atoms, methylphenylamino, methylbenzylamino, alkanylamido groups of 1 to 3 carbon atoms, carbamamido, ureido, and guanidino).

"Substituted monovalent hydrocarbon group" means a monovalent hydrocarbon group wherein 1 to 4 of the hydrogen atoms bonded to carbon atoms in the chain have been replaced with other substituents. Preferred substituted monovalent hydrocarbon groups are mono, di, or trisubstituted. Preferred substituents include halogen atoms; lower monovalent hydrocarbon groups; hydroxy groups; aryloxy groups (e.g., phenoxy, chlorophenoxy, tolyloxy, methoxyphenoxy, benzyloxy, alkyloxycarbonylphenoxy, and acyloxyphenoxy); acyloxy groups (e.g., propionyloxy, benzyloxy, and acetoxy); carboxy groups; monocyclic aromatic groups; monocyclic heteroaromatic groups; monocyclic carbocyclic groups, monocyclic heterocyclic groups, and amino groups (e.g., amino, mono- and di-alkanylamino groups of 1 to 3 carbon atoms, methylphenylamino, methylbenzylamino, alkanylamido groups of 1 to 3 carbon atoms, carbamamido, ureido, and guanidino).

Prostaglandins Used in the Invention

This invention relates to the use of prostaglandin F analogs (PGF's) to treat hair loss. Suitable PGF's can have a structure selected from the group consisting of:

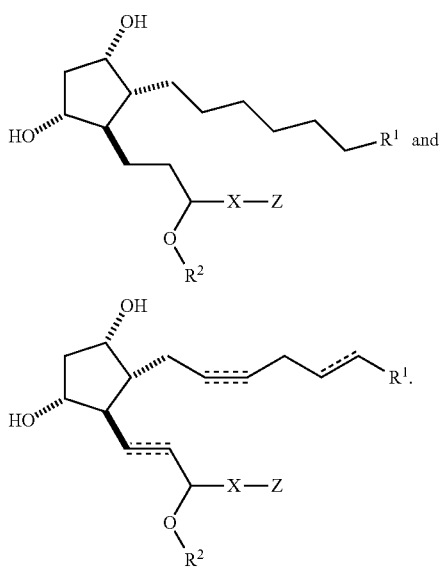

The PGF can also be selected from the group consisting of pharmaceutically acceptable salts and hydrates of the structures above; biohydrolyzable amides, esters, and imides of the structures above; and optical isomers, diastereomers, and enantiomers of the structures above. Thus, at all stereocenters where stereochemistry is not defined ($C_{11}$, $C_{12}$, and $C_{15}$), both epimers are envisioned. Preferred stereochemistry at all such stereocenters of the compounds of the invention mimic that of naturally occurring $PGF_{2\alpha}$. A combination of two or more PGF's can also be used.

$R^1$ is selected from the group consisting of C(O)OH, C(O)NHOH, C(O)$OR^3$, $CH_2OH$, S(O)$_2R^3$, C(O)$NHR^3$, C(O)NHS(O)$_2R^4$, tetrazole, a cationic salt moiety, a pharmaceutically acceptable amine or ester comprising 2 to 13 carbon atoms, and a biometabolizable amine or ester comprising 2 to 13 atoms. Preferably, $R^1$ is selected from the group consisting of $CO_2H$, C(O)NHOH, $CO_2R^3$, C(O)NHS(O)$_2R^4$, and tetrazole. More preferably, $R^1$ is selected from the group consisting of $CO_2H$ and $CO_2R^3$.

$R^2$ is selected from the group consisting of a hydrogen atom, a lower heterogenous group, and lower monovalent hydrocarbon groups. Preferably, $R^2$ is a hydrogen atom.

$R^3$ is selected from the group consisting of a monovalent hydrocarbon group, a heterogeneous group, a carbocyclic group, a heterocyclic group, an aromatic group, a heteroaromatic group, a substituted monovalent hydrocarbon group, a substituted heterogeneous group, a substituted carbocyclic group, a substituted heterocyclic group, a substituted aromatic group, and a substituted heteroaromatic group. Preferably, $R^3$ is selected from the group consisting of methyl, ethyl, and isopropyl $R^4$ is selected from the group consisting of a monovalent hydrocarbon group, a heterogeneous group, a carbocyclic group, a heterocyclic group, an aromatic group, a heteroaromatic group, a substituted monovalent hydrocarbon group, a substituted heterogeneous group, a substituted carbocyclic group, a substituted heterocyclic group, a substituted aromatic group, and a substituted heteroaromatic group. Preferably, $R^4$ is a phenyl group.

X is divalent. X is selected from the group consisting of —C≡C—, a covalent bond, —CH═C═CH—, —CH═CH—, —CH═N—, —C(O)—, —C(O)Y—, —(CH$_2$)$_n$—, wherein n is 2 to 4, —CH$_2$NH—, —CH$_2$S—, and —CH$_2$O—.

Y is selected from the group consisting of O, S, and NH.

Z is selected from the group consisting of a carbocyclic group, a heterocyclic group, an aromatic group, a heteroaromatic group, a substituted carbocyclic group, a substituted heterocyclic group, a substituted aromatic group, and a substituted heteroaromatic group.

Preferably, when X is a covalent bond, Z is selected from the group consisting of an aromatic group, a heteroaromatic group, a substituted aromatic group, and a substituted heteroaromatic group. More preferably, when X is a covalent bond, Z is a bicyclic heteroaromatic group.

Preferably, when X is —C≡C—, Z is a monocyclic aromatic group. More preferably, when X is —C≡C—, Z is selected from the group consisting of furanyl, thienyl, and phenyl.

Bonds shown as dashed lines in the second structure above indicate that those bonds may optionally be double or triple bonds. For example, when $R^1$ is C(O)OH in the structure:

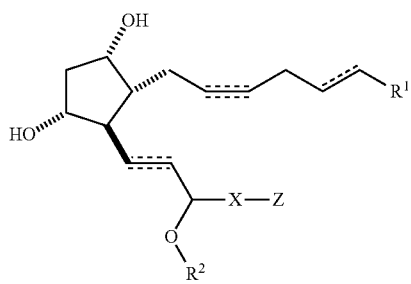

The bond at the C2-C3 position may be a single bond or a double bond. The bond at the C5-C6 position may be a single, double, or triple bond. The bond at the C13-C14 position may be a single, double, or triple bond.

Examples of PGF's' having the structure:

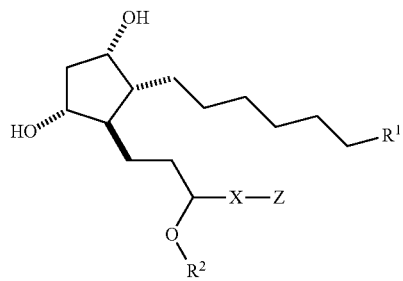

which are suitable for component A) are shown below in Tables 1 and 2.

TABLE 1

Examples of Suitable PGF's for Component A)

13,14-dihydro-16,17-Z-didehyro-17-(2-fluorophenyl)-17-trinor PGF$_{1\alpha}$

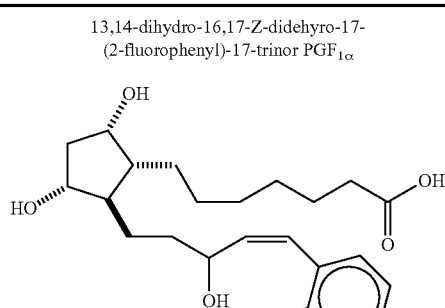

13,14-dihydro-16,17-E-didehyro-17-(2-fluorophenyl)-17-trinor PGF$_{1\alpha}$

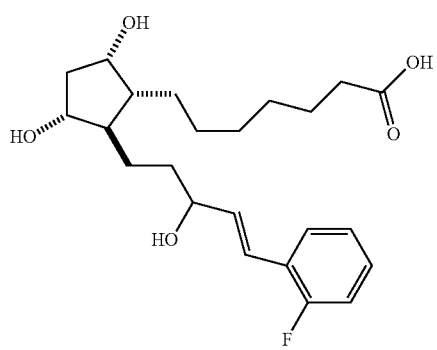 [SMILES: O=C(O)CCCCCC[C@@H]1[C@@H](CCC(O)/C=C/c2ccccc2F)[C@H](O)C[C@@H]1O]

13,14-dihydro-E-16,17-didehyro-17-phenyl-17-trinor PGF$_{1\alpha}$

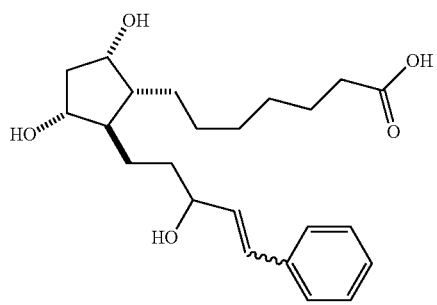 [SMILES: O=C(O)CCCCCC[C@@H]1[C@@H](CCC(O)C=Cc2ccccc2)[C@H](O)C[C@@H]1O]

TABLE 1-continued

Examples of Suitable PGF's for Component A)

13,14-dihydro-E-16,17-didehyro-17-(2-fluoro-4-methylphenyl)-17-trinor PGF$_{1\alpha}$

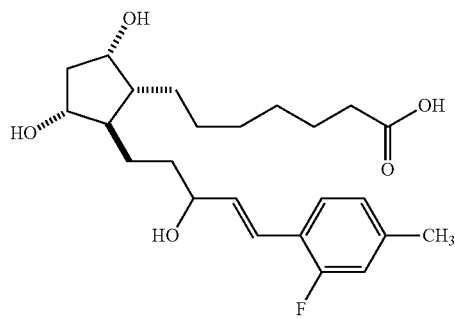 [SMILES: Cc1ccc(/C=C/C(O)CC[C@@H]2[C@@H](CCCCCCC(=O)O)[C@@H](O)C[C@H]2O)c(F)c1]

13,14-dihydro-E-16,17-didehyro-17-(2,4-dichlorophenyl)-17-trinor PGF$_{1\alpha}$

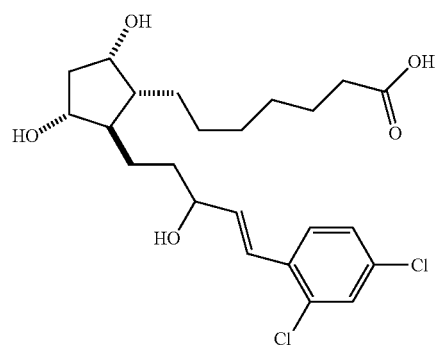 [SMILES: O=C(O)CCCCCC[C@@H]1[C@@H](CCC(O)/C=C/c2ccc(Cl)cc2Cl)[C@H](O)C[C@@H]1O]

13,14-dihydro-E-16,17-didehyro-17-(2-fluoro-5-chlorophenyl)-17-trinor PGF$_{1\alpha}$

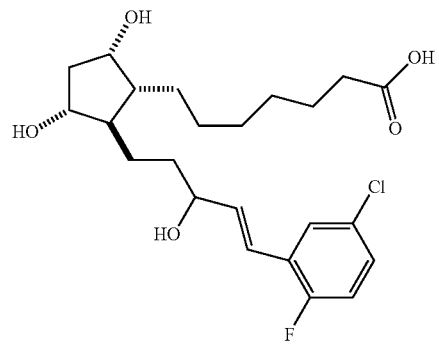 [SMILES: O=C(O)CCCCCC[C@@H]1[C@@H](CCC(O)/C=C/c2cc(Cl)ccc2F)[C@H](O)C[C@@H]1O]

13,14-dihydro-E-16,17-didehyro-17-(2,5-difluorophenyl)-17-trinor PGF$_{1\alpha}$

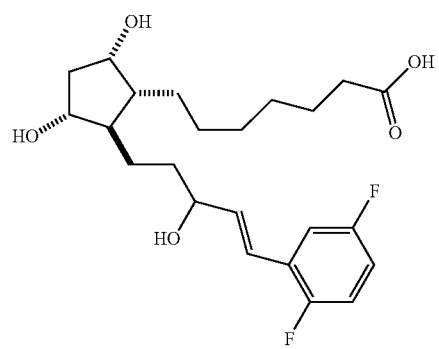 [SMILES: O=C(O)CCCCCC[C@@H]1[C@@H](CCC(O)/C=C/c2cc(F)ccc2F)[C@H](O)C[C@@H]1O]

TABLE 1-continued

Examples of Suitable PGF's for Component A)

13,14-dihydro-E-16,17-didehyro-17-
(2-fluoro-3-methoxyphenyl)-17-trinor PGF$_{1\alpha}$

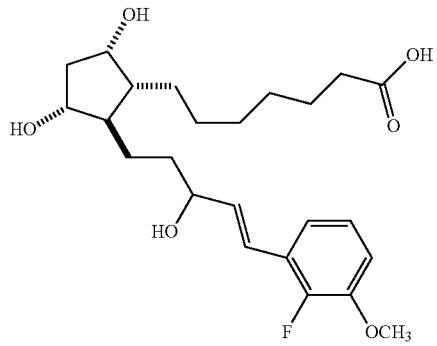 [SMILES: COc1cccc(/C=C/C(O)CC[C@@H]2[C@@H](CCCCCCC(=O)O)[C@@H](O)C[C@H]2O)c1F]

13,14-dihydro-16,17-didehyro-17-(4-
fluorophenyl)-17-trinor PGF$_{1\alpha}$

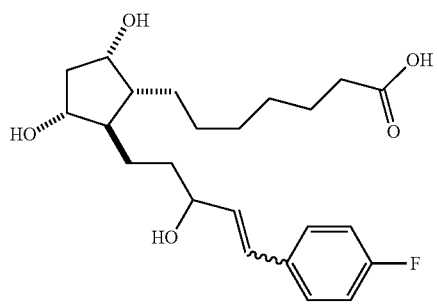 [SMILES: O=C(O)CCCCCC[C@@H]1[C@@H](CCC(O)C=Cc2ccc(F)cc2)[C@H](O)C[C@@H]1O]

13,14-dihydro-E-16,17-didehyro-17-
(2-fluoro-3-chlorophenyl)-17-trinor PGF$_{1\alpha}$

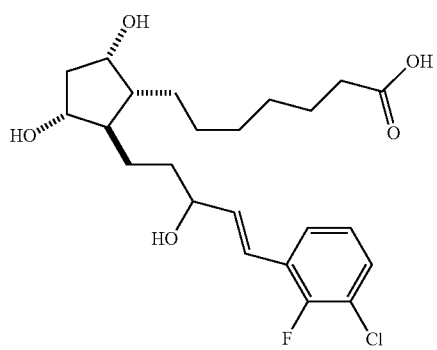 [SMILES: O=C(O)CCCCCC[C@@H]1[C@@H](CCC(O)/C=C/c2cccc(Cl)c2F)[C@H](O)C[C@@H]1O]

13,14-dihydro-16,17-didehyro-17-
(3-fluorophenyl)-17-trinor PGF$_{1\alpha}$

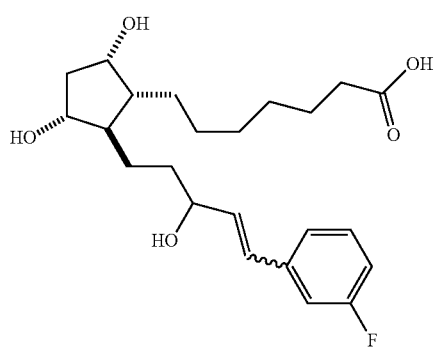 [SMILES: O=C(O)CCCCCC[C@@H]1[C@@H](CCC(O)C=Cc2cccc(F)c2)[C@H](O)C[C@@H]1O]

TABLE 1-continued

Examples of Suitable PGF's for Component A)

13,14-dihydro-E-16,17-didehyro-17-
(3-trifluoromethylphenyl)-17-trinor PGF$_{1\alpha}$

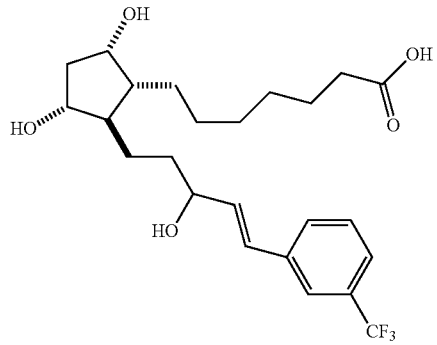 [SMILES: O=C(O)CCCCCC[C@@H]1[C@@H](CCC(O)/C=C/c2cccc(C(F)(F)F)c2)[C@H](O)C[C@@H]1O]

13,14-dihydro-16,17,17,18-dienyl-18-
phenyl-18-dinor PGF$_{1\alpha}$

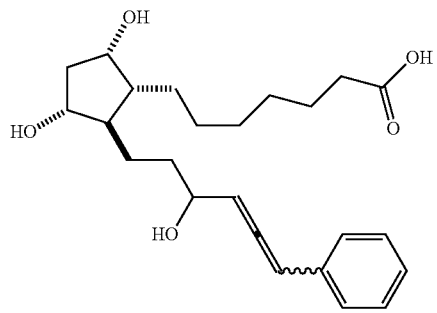

13,14-dihydro-16,17,17,18-dienyl-18-
(2,4-difluorophenyl)-18-dinor PGF$_{1\alpha}$

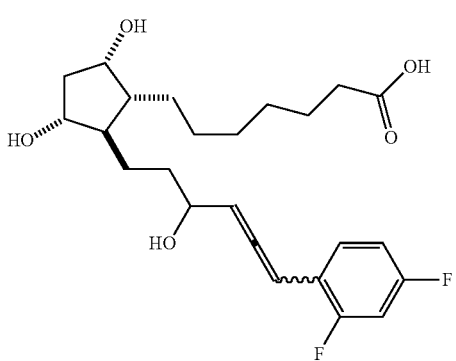

13,14-dihydro-16,17,17,18-dienyl-18-
(4-methoxyphenyl)-18-dinor PGF$_{1\alpha}$

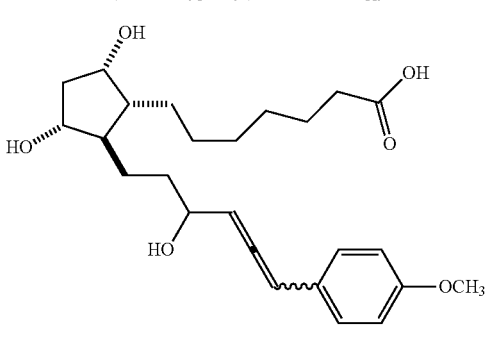

TABLE 1-continued

Examples of Suitable PGF's for Component A)

13,14-dihydro-16,17,17,18-dienyl-
18-(2-fluorophenyl)-18-dinor PGF$_{1\alpha}$

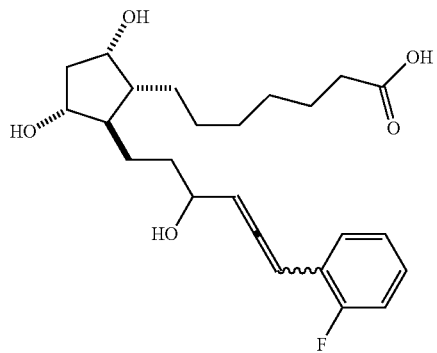

13,14-dihydro-16,17,17,18-dienyl-
18-(3-trifluoromethylphenyl)-18-dinor PGF$_{1\alpha}$

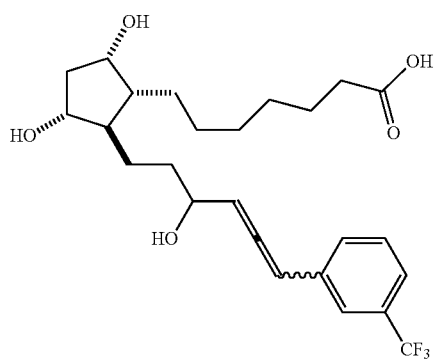

13,14-dihydro-16,17-didehydro-17-(2-fluorophenyl)-
17-trinor PGF$_{1\alpha}$ 1-hydroxamic acid

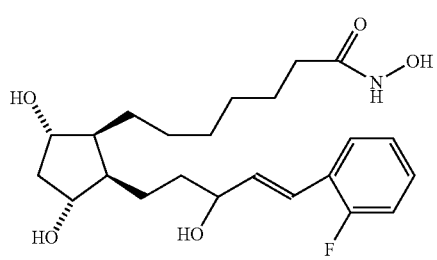 [SMILES: O=C(CCCCCC[C@H]1[C@@H](CCC(O)/C=C/c2ccccc2F)[C@H](O)C[C@@H]1O)NO]

13,14-dihydro-16,17,17,18-dienyl-18-
phenyl-18-dinor PGF$_{2\alpha}$ 1-hydroxamic acid

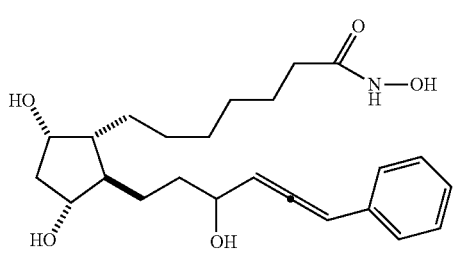

13,14-dihydro-16-oxo-16-phenyl-16-
tetranorPGF$_{1\alpha}$

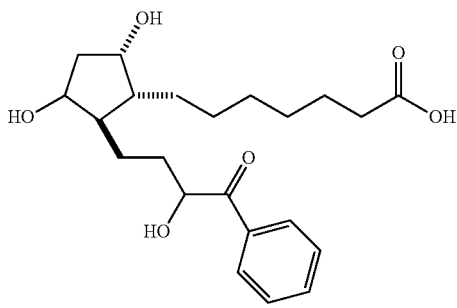 [SMILES: O=C(O)CCCCCC[C@H]1[C@@H](O)CC(O)[C@@H]1CCC(O)C(=O)c1ccccc1]

13,14-dihydro-16,17-didehydro-17-3-fluorophenyl-
17-trinor PGF$_{1\alpha}$ 1-N-methanesulfonamide

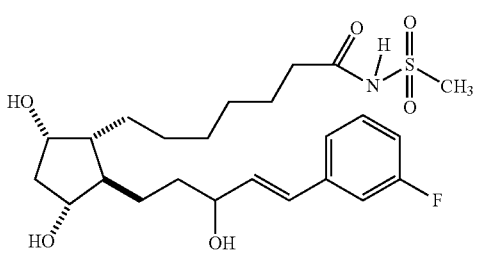 [SMILES: CS(=O)(=O)NC(=O)CCCCCC[C@@H]1[C@@H](CCC(O)/C=C/c2cccc(F)c2)[C@H](O)C[C@@H]1O]

13,14-dihydro-16-oxo-16-(3,5-
difluorophenyl)-16-tetranor PGF$_{1\alpha}$

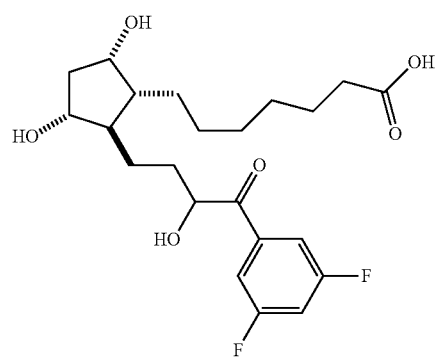 [SMILES: O=C(O)CCCCCC[C@@H]1[C@@H](CCC(O)C(=O)c2cc(F)cc(F)c2)[C@H](O)C[C@@H]1O]

13,14-dihydro-16-oxo-16-(2-furanyl)-
16-tetranor PGF$_{1\alpha}$

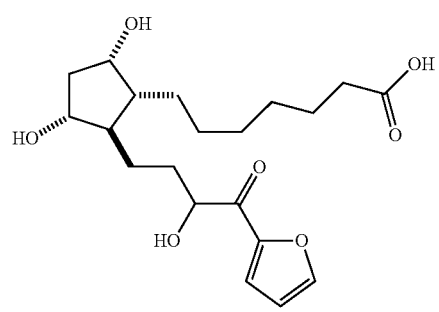 [SMILES: O=C(O)CCCCCC[C@@H]1[C@@H](CCC(O)C(=O)c2ccco2)[C@H](O)C[C@@H]1O]

TABLE 1-continued

Examples of Suitable PGF's for Component A)

13,14-dihydro-16-oxo-16-(6-fluorobenzo-
[b]-furanyl-16-(tetranor PGF$_{1\alpha}$ 13,14-dihydro-16-oxo16-(2-
benzothiazolyl)-16-tetranor PGF$_{1\alpha}$ 13,14-dihydro-16-oxo-16-(3-chloro-
5-methylphenyl)-16-tetranor PGF$_{1\alpha}$

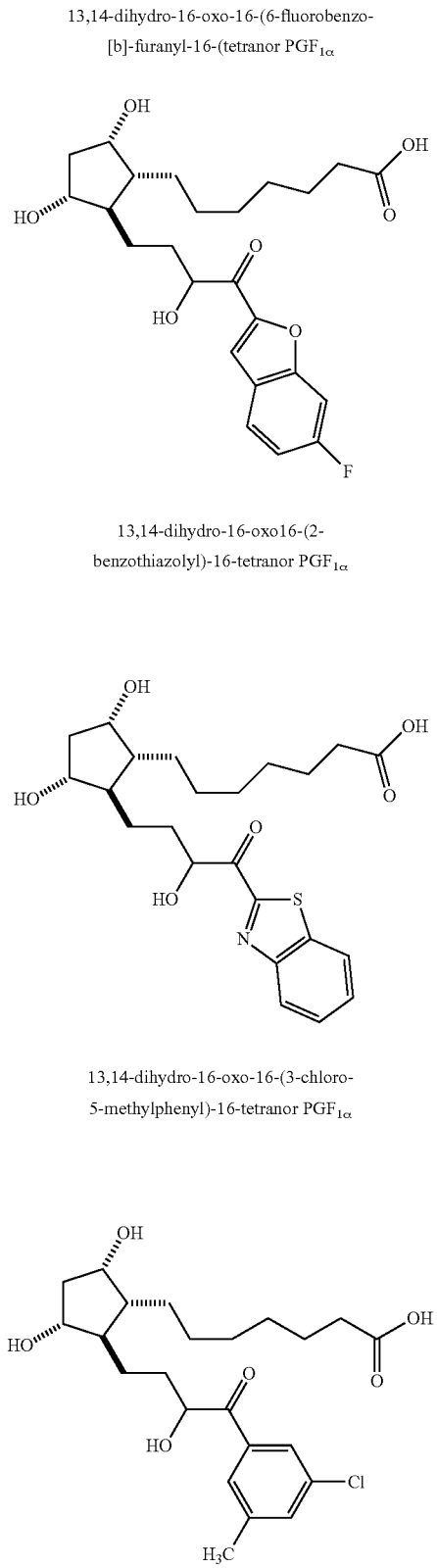

TABLE 1-continued

Examples of Suitable PGF's for Component A)

13,14-dihydro-16-oxo-16-(2-
benzo[b]thienyl)-16-tetranor PGF$_{1\alpha}$ 13,14-dihydro-16-oxo-16-(3,5-difluorophenyl)-
16-tetranor PGF$_{1\alpha}$ 1-hydroxamic acid 13,14-dihydro-16-oxo-16-(4-methylphenyl)-
16-tetranor PGF$_{1\alpha}$ 1-hydroxamic acid 13,14-dihydro-16-oxo-17-aza-17-
phenyl-17-trinor PGF$_{1\alpha}$

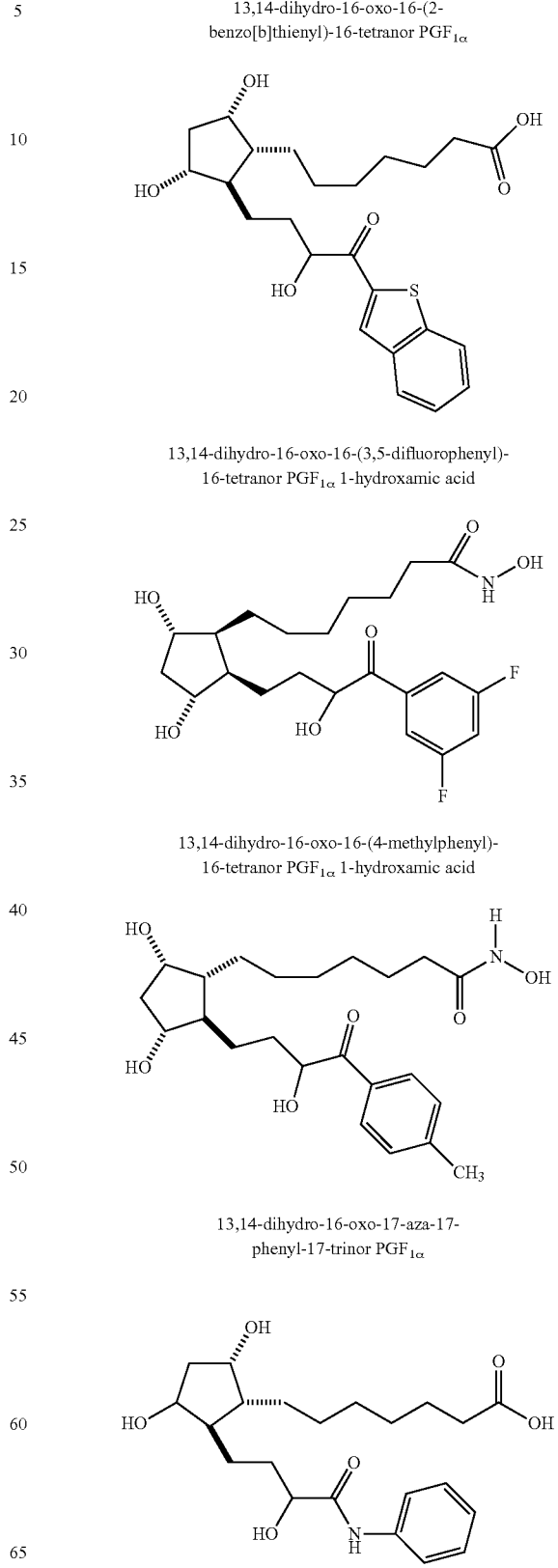

TABLE 1-continued

Examples of Suitable PGF's for Component A)

13,14-dihydro-16-oxo-17-aza-17-(2-furyl)-17-trinor PGF$_{1\alpha}$

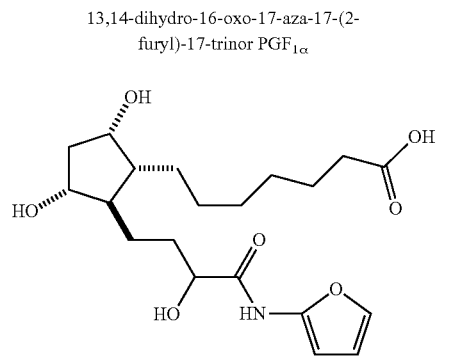

13,14-dihydro--16-oxo-16-(2-benzo[b]thienyl)-16-tretranor PGF$_{1\alpha}$ 1-N-methanesulfonamide

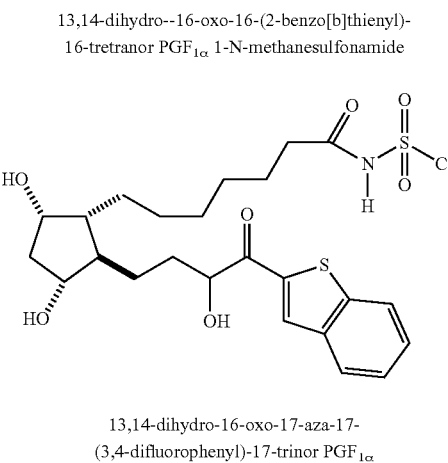

13,14-dihydro-16-oxo-17-aza-17-(3,4-difluorophenyl)-17-trinor PGF$_{1\alpha}$

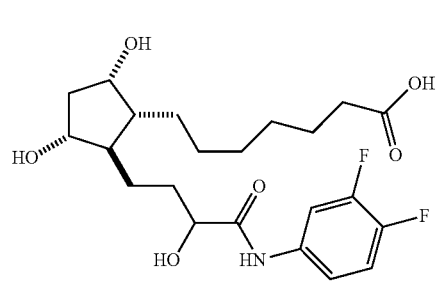 [SMILES: O=C(O)CCCCCC[C@@H]1[C@@H](CCC(O)C(=O)Nc2ccc(F)c(F)c2)[C@H](O)C[C@@H]1O]

13,14-dihydro-16-oxo-17-aza-17-(2-fluorophenyl)-17-trinor PGF$_{1\alpha}$

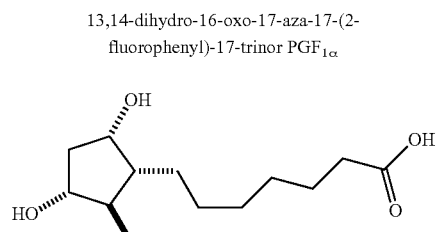
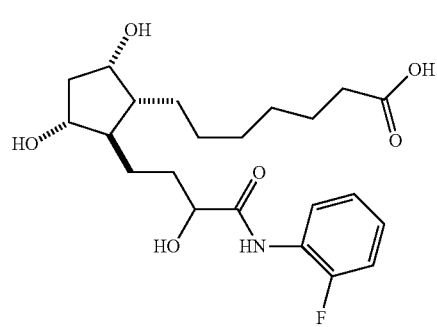 [SMILES: O=C(O)CCCCCC[C@@H]1[C@@H](CCC(O)C(=O)Nc2ccccc2F)[C@H](O)C[C@@H]1O]

TABLE 1-continued

Examples of Suitable PGF's for Component A)

13,14-dihydro-16-oxo-16-phenoxy-16-tetranor PGF$_{1\alpha}$

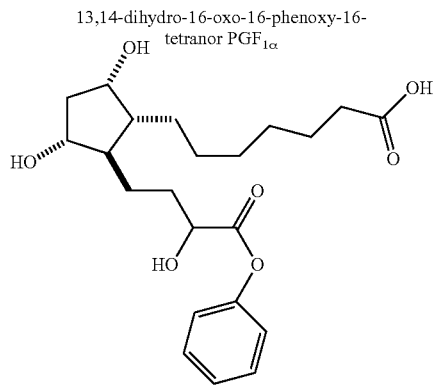

13,14-dihydro-16-oxo-16-(3-trifluoromethylphenoxy)-16-tetranor PGF$_{1\alpha}$

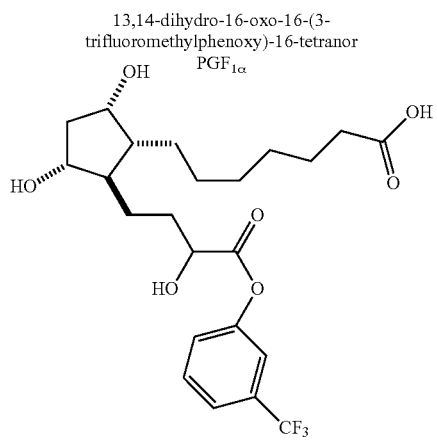
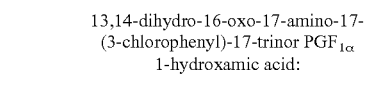

13,14-dihydro-16-oxo-17-amino-17-(3-chlorophenyl)-17-trinor PGF$_{1\alpha}$ 1-hydroxamic acid:

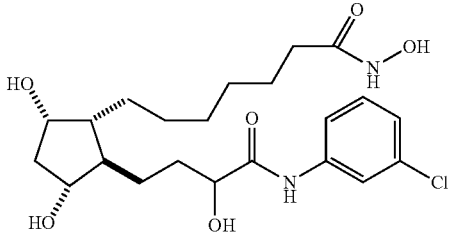 [SMILES: O=C(CCCCCC[C@@H]1[C@@H](CCC(O)C(=O)Nc2cccc(Cl)c2)[C@H](O)C[C@@H]1O)NO]
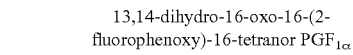

13,14-dihydro-16-oxo-16-(2-fluorophenoxy)-16-tetranor PGF$_{1\alpha}$

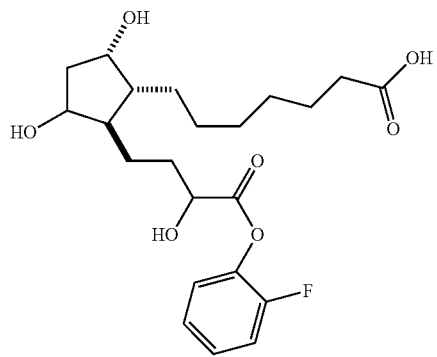 [SMILES: O=C(O)CCCCCC[C@H]1[C@@H](O)CC(O)[C@@H]1CCC(O)C(=O)Oc1ccccc1F]

TABLE 1-continued

Examples of Suitable PGF's for Component A)

13,14-dihydro-16-oxo-17-aza-17-
(3,4-difluorophenyl)-17-trinor
PGF$_{1\alpha}$ 1-hydroxamic acid

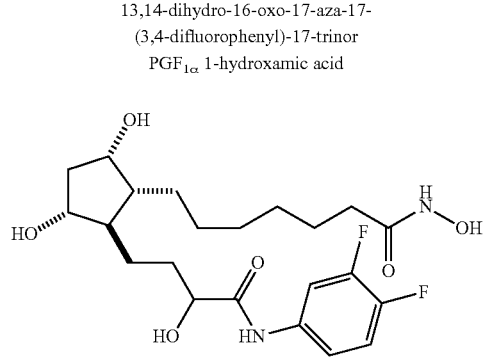

13,14-dihydro-16-oxo-17-amino-17-
phenyl-17-trinor PGF$_{1\alpha}$ 1-methane
sulfonamide

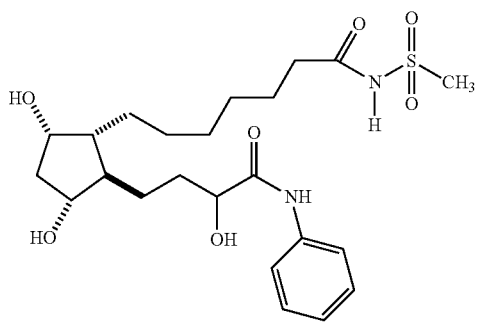 [SMILES: CS(=O)(=O)NC(=O)CCCCCC[C@@H]1[C@@H](CCC(O)C(=O)Nc2ccccc2)[C@H](O)C[C@@H]1O]

13,14-dihydro-16,17-didehydro-17-
aza-17-phenyl-17-trinor PGF$_{1\alpha}$

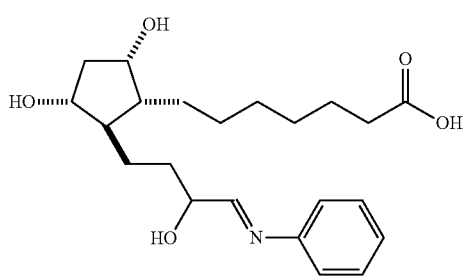 [SMILES: O=C(O)CCCCCC[C@@H]1[C@@H](CCC(O)/C=N/c2ccccc2)[C@H](O)C[C@@H]1O]

13,14-dihydro-16,17-didehydro-17-
aza-17-(2-furanyl)-17-trinor PGF$_{1\alpha}$

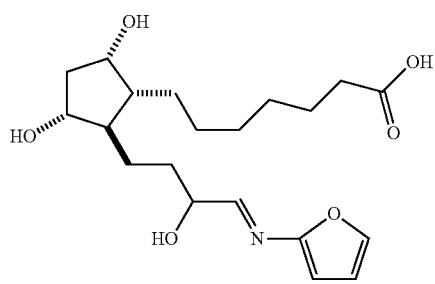 [SMILES: O=C(O)CCCCCC[C@@H]1[C@@H](CCC(O)/C=N/c2ccco2)[C@H](O)C[C@@H]1O]

13,14-dihydro-16,17-didehydro-17-
aza-17-(3-fluorophenyl)-17-trinor PGF$_{1\alpha}$

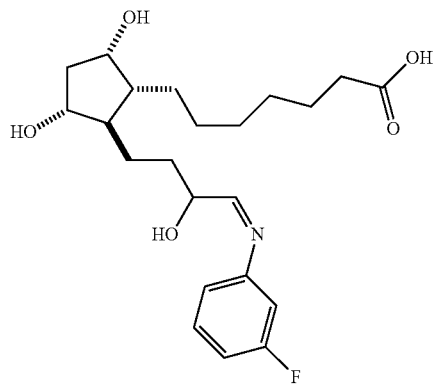 [SMILES: O=C(O)CCCCCC[C@@H]1[C@@H](CCC(O)/C=N\c2cccc(F)c2)[C@H](O)C[C@@H]1O]

13,14-dihydro-16,17-didehydro-17-
aza-17-(2-fluorophenyl)-17-trinor PGF$_{1\alpha}$

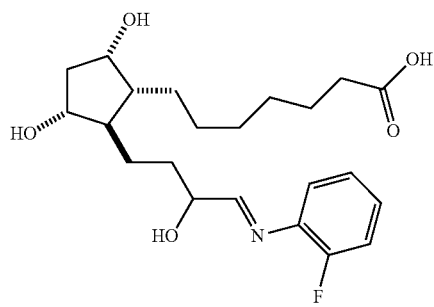 [SMILES: O=C(O)CCCCCC[C@@H]1[C@@H](CCC(O)/C=N/c2ccccc2F)[C@H](O)C[C@@H]1O]

13,14-dihydro-16-oxo-17-aza-17-
(4-phenylphenyl)-17-trinor PGF$_{1\alpha}$

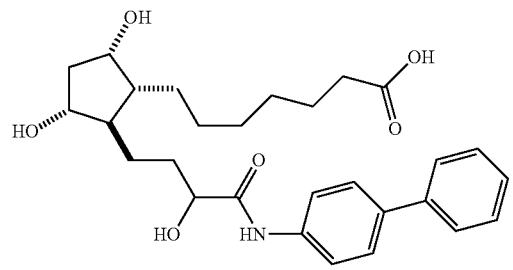 [SMILES: O=C(O)CCCCCC[C@@H]1[C@@H](CCC(O)C(=O)Nc2ccc(-c3ccccc3)cc2)[C@H](O)C[C@@H]1O]

13,14-dihydro-16,17-didehydro-17-aza-17-
(2-furanyl)-17-trinor PGF$_{1\alpha}$ 1-hydroxamic acid

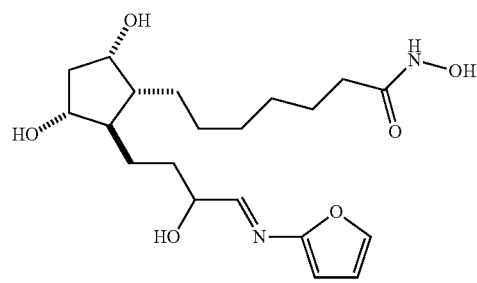 [SMILES: O=C(CCCCCC[C@@H]1[C@@H](CCC(O)/C=N/c2ccco2)[C@H](O)C[C@@H]1O)NO]

TABLE 1-continued

Examples of Suitable PGF's for Component A)

13,14-dihydro-16,17-didehydro-17-aza-17-(3-chlorophenyl)-17-trinor PGF$_{1\alpha}$ 1-hydroxamic acid

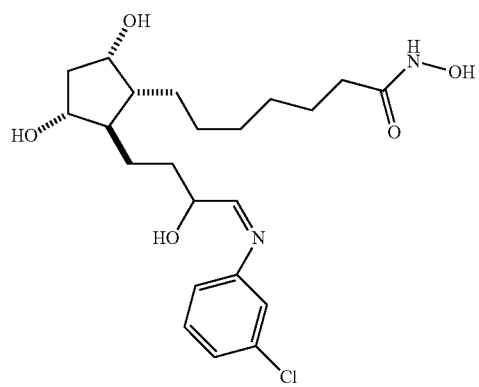 [SMILES: O=C(CCCCCC[C@@H]1[C@@H](CCC(O)/C=N\c2cccc(Cl)c2)[C@H](O)C[C@@H]1O)NO]

13,14-dihydro-16,17-didehydro-17-aza-17-(2-thienyl)-17-trinor PGF$_{1\alpha}$ 1-methanesulfonamide

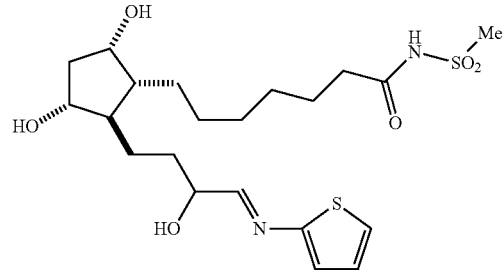 [SMILES: CS(=O)(=O)NC(=O)CCCCCC[C@@H]1[C@@H](CCC(O)/C=N/c2cccs2)[C@H](O)C[C@@H]1O]

Where Me in the table above represents a methyl group.

The PGF's in Table 1 can be prepared using conventional organic syntheses. Preferred syntheses are carried out using reaction schemes 1, 2, and 3. Scheme 1 describes a general reaction scheme for making PGFs wherein X is —CH=CH— (Formula I) or —CH=C=CH— (Formula II). Scheme 2 describes a general reaction scheme for making PGFs wherein X is —C(O)— (Formula III) or —C(O)Y— (Formula IV). Scheme 3 describes a general reaction scheme for making PGFs wherein X is —CH=N— (Formula V).

Scheme 1

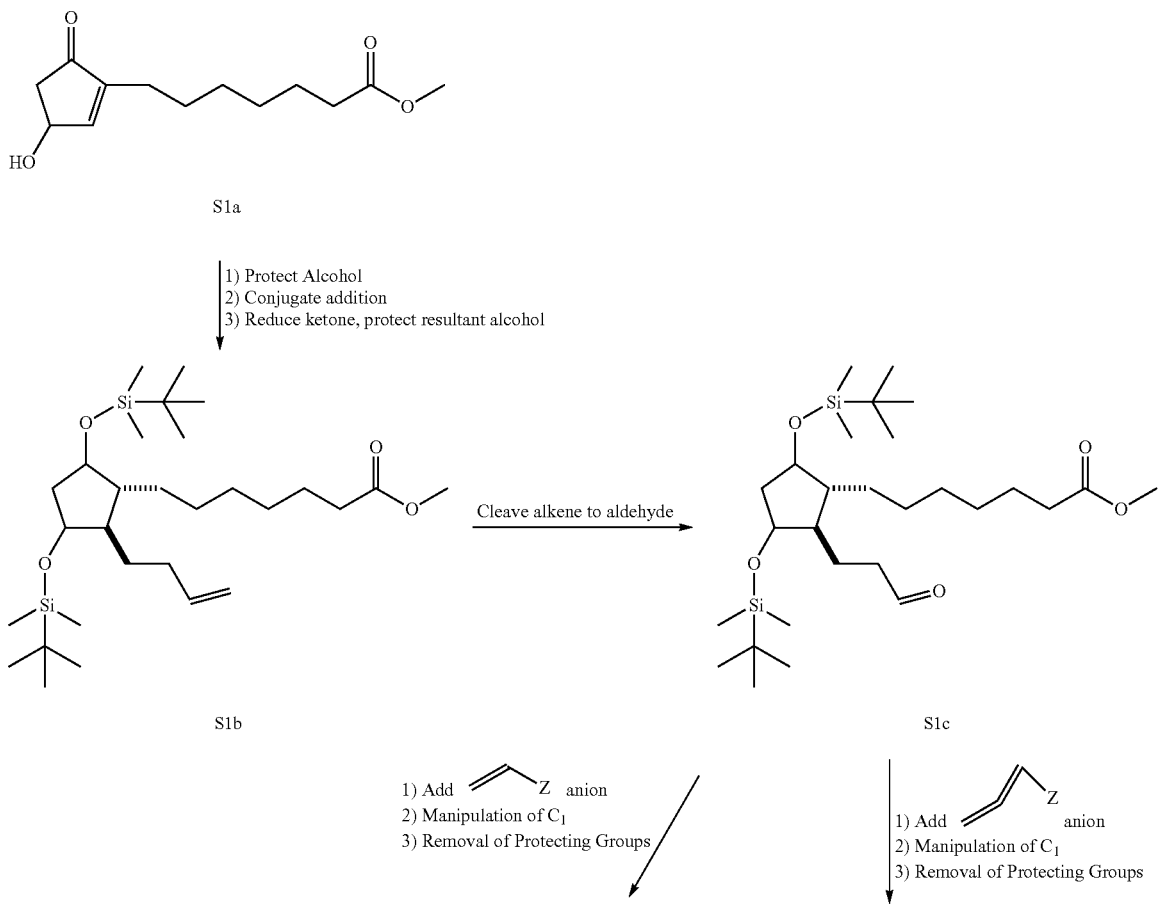

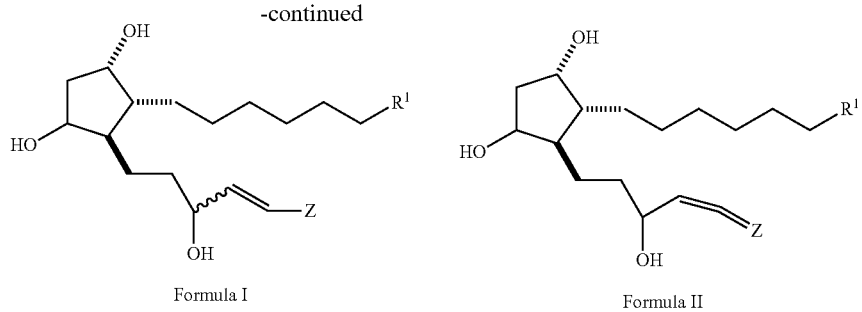

Formula I

Formula II

In Scheme 1, $R^1$ and Z are as defined above. The methyl 7(3-(R)-hydroxy-5-oxo-1-cyclopent-1-yl) heptanoate (S1a) depicted as starting material for Scheme 1 is commercially available (such as from Sumitomo Chemical or Cayman Chemical).

In Scheme 1, methyl 7-(3-(R)-hydroxy-5-oxo-1-cyclopent-1-yl) heptanoate (S1a) is reacted with a silylating agent and base in a solvent that will allow the silylation to proceed. Preferred silylating agents include tert-butyldimethylsilyl chloride and tert-butyldimethylsilyl trifluoromethanesulphonate. The most preferred silylating agent is tert-butyldimethylsilyl trifluoromethanesulphonate. Preferred bases include triethylamine, trimethylamine, and 2,6-lutidine. More preferred bases include triethylamine and 2,6-lutidine. The most preferred base is 2,6-lutidine. Preferred solvents include halogenated hydrocarbon solvents with dichloromethane being the most preferred solvent. The reaction is allowed to proceed at a temperature of preferably −100° C. to 100° C., more preferably −80° C. to 80° C., and most preferably −70° C. to 23° C.

The resulting silylated compound is isolated by methods known to one of ordinary skill in the art. Such methods include extraction, solvent evaporation, distillation, and crystallization. Preferably, the silyl ether is purified after isolation by distillation under vacuum.

The silylated compound is then reacted with the cuprate generated via Grignard formation of the appropriate alkenyl bromide as disclosed, for example, in the following references: H. O. House et. al., "The Chemistry of Carbanions: A Convenient Precursor for the Generation of Lithium Organocuprates", J. Org. Chem. Vol. 40 (1975) pp. 1460-69; and P. Knochel et. al., "Zinc and Copper Carbenoids as Efficient and Selective a¹/d¹ Multicoupling Reagents", J. Amer. Chem. Soc. Vol. 111 (1989) p. 6474-76. Preferred alkenyl bromides include 4-bromo-1-butene, 4-bromo-1-butyne, 4-bromo-2-methyl-1-butene, and 4-bromo-2-ethyl-1-butene. The most preferred alkenyl bromide is 4-bromo-1-butene. Preferred solvents include ethereal solvents, of which diethyl ether and tetrahydrofuran are preferred. The most preferred solvent is tetrahydrofuran. The Grignard reagent is allowed to form at a temperature of 100° C. to 23° C., more preferably 85° C. to 30° C., and most preferably 75° C. to 65° C. The reaction time is preferably 1 to 6 hours, more preferably 2 to 5 hours, and most preferably 3 to 4 hours.

Once the Grignard reagent is formed, the cuprate is generated from the alkenyl magnesium species. The temperature range for cuprate formation is −100° C. to 0° C. The preferred temperature range is −80° C. to −20° C. The more preferred temperature range is −75° C. to −50° C. The preferred reaction time is 30 minutes to 6 hours, more preferably 45 minutes to 3 hours. The most preferred reaction time is 1 to 1.5 hours.

The alkene thus formed is isolated by methods known to one of ordinary skill in the art. Such methods include extraction, solvent evaporation, distillation, and crystallization. Preferably, the alkene is purified by flash chromatography on silica gel (Merck, 230-400 mesh) using 10% EtOAc/hexanes as the eluent. (EtOAc represents ethyl acetate.)

The alkene is then reacted with a hydride reducing agent and a polar, protic solvent to give the C-9 alcohol. Preferred reducing agents include lithium aluminum hydride, sodium borohydride, and L-selectride. More preferred reducing agents include sodium borohydride, and L-selectride. The most preferred reducing agent is sodium borohydride. Preferred solvents include methanol, ethanol, and butanol. The most preferred solvent is methanol. The reduction is carried out at a temperature of −100° C. to 23° C. The preferred temperature range is −60° C. to 0° C. The most preferred temperature range is −45° C. to −20° C.

The resulting alcohol is isolated by methods known to one of ordinary skill in the art. Such methods include extraction, solvent evaporation, distillation, and crystallization. Preferably, the alcohol is purified by flash chromatography on silica gel (Merck, 230-400 mesh) using 20% EtOAc/hexanes as the eluent.

The resultant alcohol can be protected as described previously herein. Preferred silylating agents in this case also include tert-butyldimethylsilyl chloride and tert-butyldimethylsilyl trifluoromethanesulfonate. The most preferred silylating agent is tert-butyldimethylsilyl trifluoromethanesulfonate. Preferred bases include triethylamine, trimethylamine, and 2,6-lutidine. More preferred bases include triethylamine and 2,6-lutidine. The most preferred base is 2,6-lutidine. Preferred solvents include halogenated hydrocarbon solvents with dichloromethane being the most preferred solvent. The reaction is allowed to proceed at a temperature of preferably −100° C. to 100° C., more preferably −80° C. to 80° C., and most preferably −70° C. to 23° C.

The resulting silylated compound, S1b is isolated by methods known to one of ordinary skill in the art. Such methods include extraction, solvent evaporation, distillation, and crystallization. Preferably, the silyl ether is purified after isolation by distillation under vacuum, giving compound S1b.

The protected alcohol is then treated with a form of osmium and sodium periodate in a solvent in which both are soluble. Preferred forms of osmium include osmium tetraoxide and potassium osmate. Preferred solvent systems include 1:1 mixtures of acetic acid and water and 1:1:2 mixtures of water, acetic acid and THF. (THF represents tetrahydrofuran.) The result of this treatment is the aldehyde, S1c.

The compound S1c is isolated by methods known to one of ordinary skill in the art. Such methods include extraction, solvent evaporation, distillation, and crystallization. Preferably, S1c is purified by flash chromatography on silica gel (Merck, 230-400 mesh) using 20% EtOAc/hexanes as the eluent.

The key intermediate aldehyde depicted as S1c can be reacted with a variety of unsaturated alkenyl anion nucleophiles to provide the C-9 and C-11-protected 13,14-dihydro-prostaglandin $F_{1\alpha}$ derivatives.

The resulting compounds can be isolated, but are generally deprotected using techniques known to one of ordinary skill in the art, and optionally, manipulated at C-1 to provide the desired acid derivative at $R^1$. For example, the condensation of a methyl ester with an amine or a hydroxylamine provides an amide or a hydroxamic acid compound, respectively. After any such manipulation at C-1, the compounds are isolated as the final 13,14-dihydro-15-substituted-15-pentanor prostaglandin $F_{1\alpha}$ derivative, Formula I.

Compounds depicted by Formula II can be made directly from intermediate S1c in a manner similar to that for compounds depicted by Formula I substituting the appropriate allene anion. With allene nucleophiles, the reaction is carried out preferably at −80° C. to 0° C., more preferably −80° C. to −20° C., and most preferably −80° C. to −40° C. Preferred bases for the reaction include n-butyl lithium, s-butyl lithium, and t-butyl lithium. The most preferred base is n-butyl lithium. Preferred solvents for the reaction are ether solvents. Preferred solvents include diethyl ether, and tetrahydrofuran. The most preferred solvent is tetrahydrofuran. With heterocyclic nucleophiles, preferred solvents include ethereal solvents. More preferred ethereal solvents include diethyl ether, dibutyl ether and tetrahydrofuran. The most preferred ethereal solvent is tetrahydrofuran. After isolation, similar C-1 manipulations and/or deprotection of the functional groups ensues using techniques known to one of ordinary skill in the art.

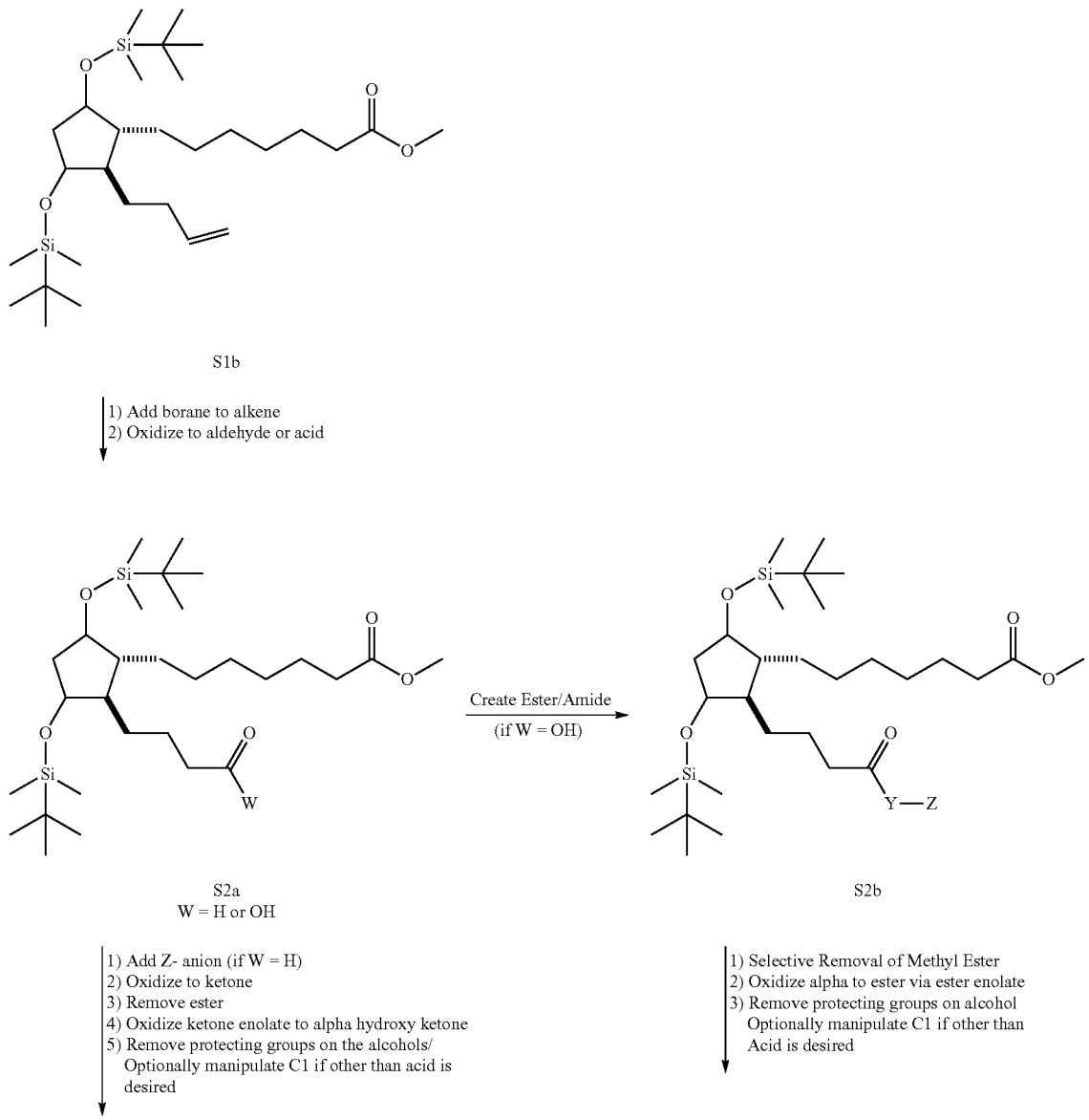

Scheme 2

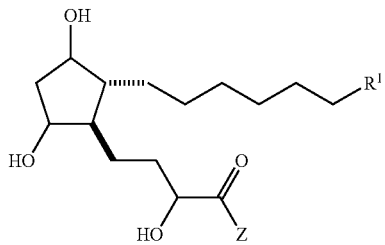

Formula III

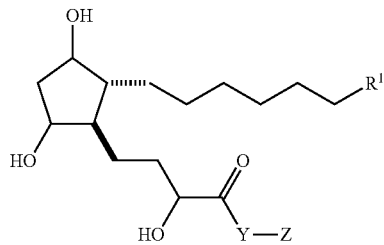

Formula IV

In Scheme 2, $R^1$, Y, and Z are as defined above. The protected alcohol S1b (from Scheme 1) is treated with a hydroborating reagent in an ethereal solvent, followed by oxidative removal of the boron reagent with a suitable oxidant to give a compound of the type S2a. Preferred hydroborating reagents include monochloroborane-dimethylsulfide, diborane, borane-tetrahydrofuran and borane-dimethylsulfide. The most preferred hydroborating reagent is borane-dimethylsulfide. Preferred ethereal solvents include THF and diethyl ether. The most preferred solvent is THF. The reaction is carried out from about 1 to about 24 hours at a temperature of about −20° C. to about +30° C. The preferred temperature range is about 0° C. to about +20° C. The hydroborated product of this reaction may then be oxidatively removed to the alcohol using alkaline hydrogen peroxide (See *Boranes in Organic Chemistry*, H. C. Brown, Cornell University Press, Ithaca, N.Y. 1972, pp. 321-325), which may then be oxidized to either the aldehyde (W═H) or to the acid (W═OH) using methods known to one of ordinary skill in the art. Alternatively, the hydroborated product may be directly oxidized to the aldehyde or acid by treatment with chromic acid or a Cr(VI) salt. Such salts include pyridinium chlorochromate (PCC) and dichrochromate. See Brown, H. C.; Kulkarni, Rao, and Patil, Tetrahedron, 1986, 45515. The preferred method is treatment of the hydroborated product with PCC in dichloromethane at room temperature. The result of these manipulations is a compound of the type S2a.

The compound S2a is isolated by methods known to one of ordinary skill in the art. Such methods include extraction, solvent evaporation, distillation, and crystallization. Preferably, S2a is purified by flash chromatography on silica gel (Merck, 230-400 mesh) using 20% EtOAc/hexanes as the eluent with 0.1% acetic acid added if W═OH.

The key intermediate aldehyde depicted as S2a can be reacted with a variety unsaturated carbon nucleophiles to provide the C-9 and C-11-protected 13,14-dihydro-16-tetranor prostaglandin $F_{1\alpha}$ derivatives of Formula III.

With aromatic and heteroaromatic nucleophiles, the reaction is carried out preferably at −80° C. to 0° C., more preferably −80° C. to −20° C., and most preferably −80° C. to −40° C. Preferred bases for the reaction include n-butyl lithium, s-butyl lithium, lithium diisopropylamide, and t-butyl lithium. The most preferred base is n-butyl lithium. Preferred solvents for the reaction are ether solvents. Preferred solvents include diethyl ether, and tetrahydrofuran. The most preferred solvent is tetrahydrofuran. With heterocyclic nucleophiles, preferred solvents include ethereal solvents. More preferred ethereal solvents include diethyl ether, dibutyl ether and tetrahydrofuran. The most preferred ethereal solvent is tetrahydrofuran.

The resulting alcohol can be isolated, but is generally oxidized as a crude isolate. The oxidation of benzylic alcohols to benzylic ketones is well known in the art. The preferred reagents to effect this reaction include $KMnO_4$, $MnO_2$, chromic acid, Jones' reagent, Collins' reagent, and PCC. The most preferred method is oxidation at room temperature in dichloromethane with PCC for about 4 hours. The ketones are isolated by column chromatography using 20% hexanes/ethyl acetate as solvent. The ester is then removed using standard conditions. See Greene and Wuts, *Protecting Groups in Organic Synthesis*, Wiley Interscience, NY pp. 224-276. The free acid is then treated with 2.1 equivalents of a strong nitrogen base to effect deprotonation both of the acid and adjacent to the benzylic ketone. Such bases include LDA. This enolate is reacted with a peroxidizing agent which has the effect of oxidizing the compound to deliver the alpha-hydroxy ketone. Such reagents include meta-chloroperoxybenzoic acid, dimethyl dioxirane, Davis' reagent and peracetic acid. The crude product may be isolated or the remaining protecting groups may be removed. At this point manipulation of the acid at C-1 may take place. For example, re-esterifying, making the amide, the hydroxamic acid or the sulfonamide using methods known to one of ordinary skill in the art may be performed to yield compounds according to Formula III.

Compounds depicted by Formula IV can be made from intermediate S2b. In this case, condensation of the free acid is readily achieved with a variety of alcohols and amines, either by the use of coupling agents such as dicyclohexylcarbodiimide ("DCC"), or by activating the acid with, for example, oxalyl chloride. Following this is the selective removal of the methyl esters as described in Greene and Wuts, *Protecting Groups in Organic Synthesis*, Wiley Interscience, NY pp. 224-276, and the oxidation of the ester enolates using the same technique described above for the ketone intermediates. Similarly, as described above, the remaining protecting groups are removed and the desired manipulation of C-1 is effected, yielding compounds of Formula IV.

Scheme 3

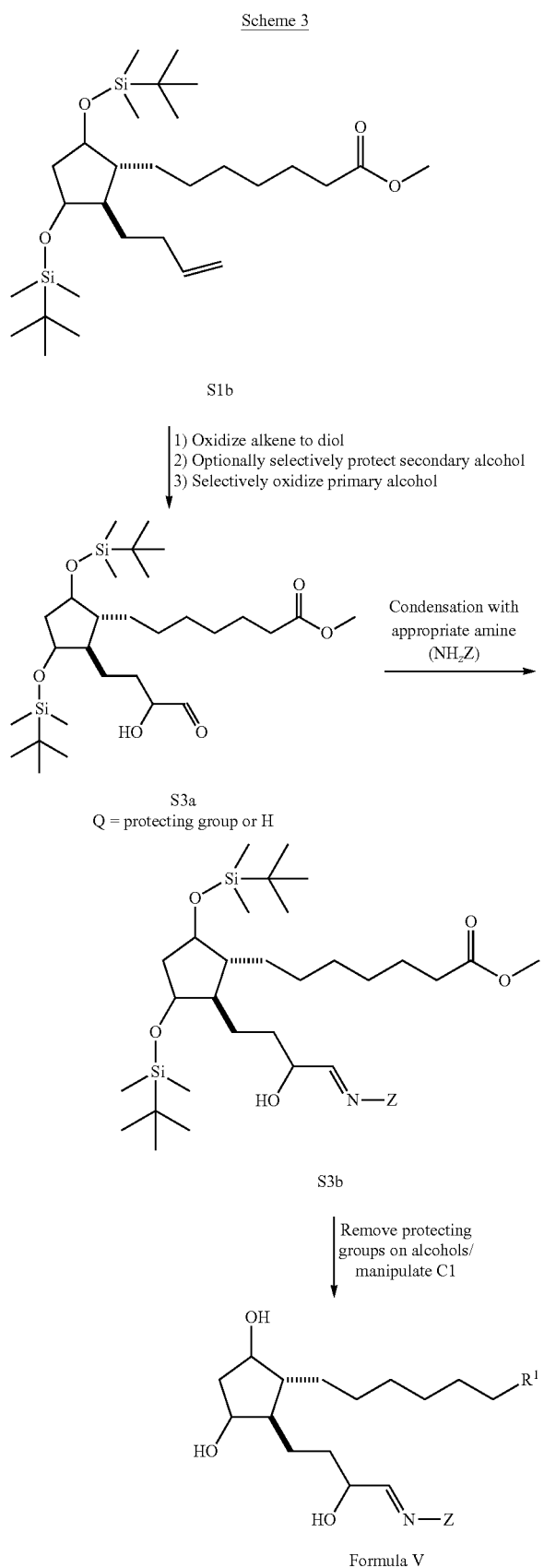

In Scheme 3, $R^1$ and Z are as defined above. The alkene S1b (from Scheme 1) is treated with an osmium salt and with an optional catalyst reoxidant, preferably N-methyl morpholine N-oxide ("NMO"), to give the diol. This diol is isolated by extraction and purified by silica gel chromatography. The diol is then oxidized selectively to the alpha hydroxy aldehyde. This may be accomplished in several ways. For example, a selective oxidant such as DMSO-oxalyl chloride may be used. ("DMSO" represents dimethylsulfoxide.) Alternatively, the primary alcohol may be selectively protected, then the secondary alcohol protected, then the protection on the primary alcohol may then be removed and the alcohol oxidized as described above in Scheme II. However, the preferred method is the addition of a o-bromo-benzyl bromide protecting group, which can be removed with concomitant oxidation by tributyl tin hydride and like reagents. This technique yields compounds of the type S3a, wherein Q=H. From this step follows the condensation of the aldehyde with an amine to form an imine of the type S3b. Appropriate removal of protecting groups and manipulation of C-1 as stated above in Schemes I and II yields compounds of Formula V.

TABLE 2

Examples of Suitable PGF's 13,14-dihydro-15-(2-benzothienyl)-15-pentanor $PGF_{1\alpha}$

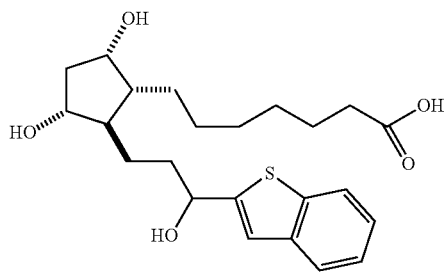 [SMILES: O=C(O)CCCCCC[C@@H]1[C@@H](CCC(O)c2cc3ccccc3s2)[C@H](O)C[C@@H]1O]

13,14-dihydro-15-(2-benzothiazolyl)-15-pentanor $PGF_{1\alpha}$

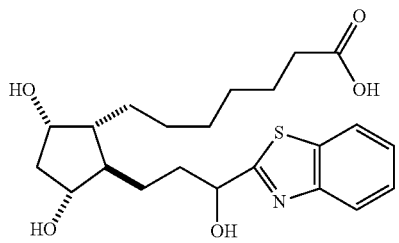 [SMILES: O=C(O)CCCCCC[C@@H]1[C@@H](CCC(O)c2nc3ccccc3s2)[C@H](O)C[C@@H]1O]

13,14-dihydro-15-(8-fluoro-2-benzothiazolyl)-15-pentanor $PGF_{1\alpha}$

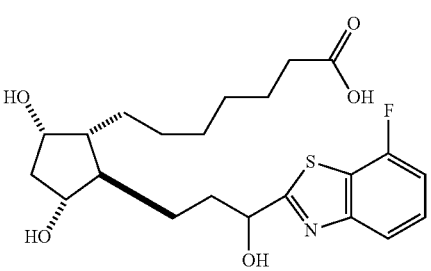 [SMILES: O=C(O)CCCCCC[C@@H]1[C@@H](CCC(O)c2nc3cccc(F)c3s2)[C@H](O)C[C@@H]1O]

TABLE 2-continued

Examples of Suitable PGF's 13,14-dihydro-16,17-ynyl-17-(2,3-difluorophenyl)-17-trinor PGF$_{1\alpha}$ 13,14-dihydro-16,17-ynyl-17-(3,4-difluorophenyl)-17-trinor PGF$_{1\alpha}$ 13,14-dihydro-16,17-ynyl17-(2,5-difluorophenyl)-17-trinor PGF$_{1\alpha}$ 13,14-dihydro-16,17-ynyl-17-(3,5-difluorophenyl)-17-trinor PGF$_{1\alpha}$

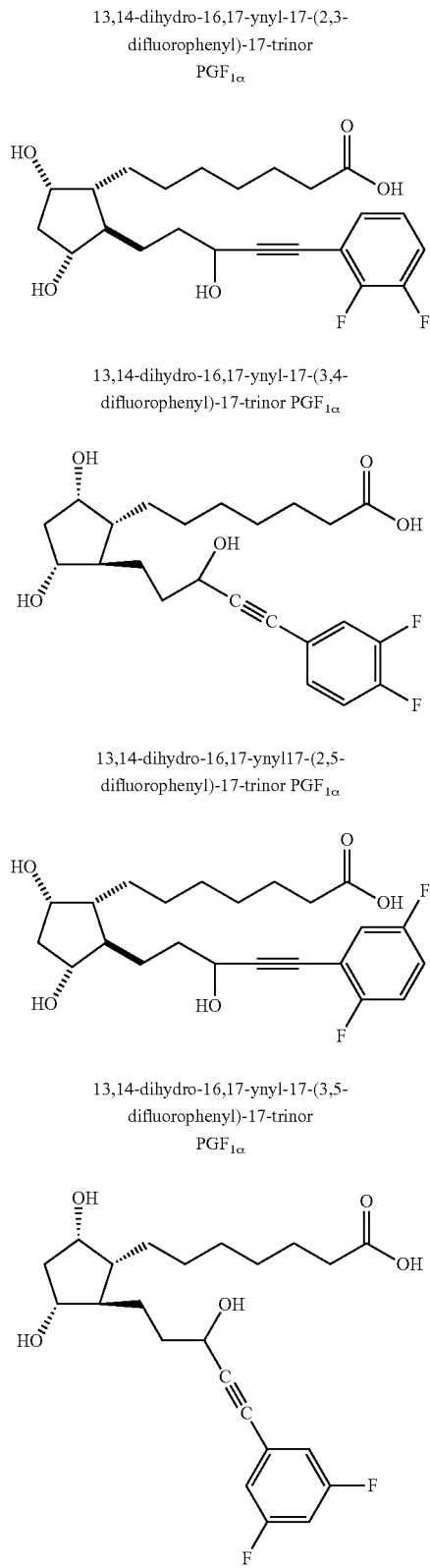

13,14-dihydro-15-(6-fluoro-2-benzothienyl)-15-pentanor PGF$_{1\alpha}$ 3,14-dihydro-16,17-ynyl-17-(2,4-difluorophenyl)-17-trinor PGF$_{1\alpha}$ 13,14-dihydro-16,17-ynyl-17-(2-fluoro-4-methylphenyl)-17-trinor PGF$_{1\alpha}$ 13,14-dihydro-16,17-ynyl-17-phenyl-17-trinor PGF$_{1\alpha}$ isopropyl ester 13,14-dihydro-16,17-ynyl-17-(3-fluorophenyl)-17-trinor PGF$_{1\alpha}$ methyl ester

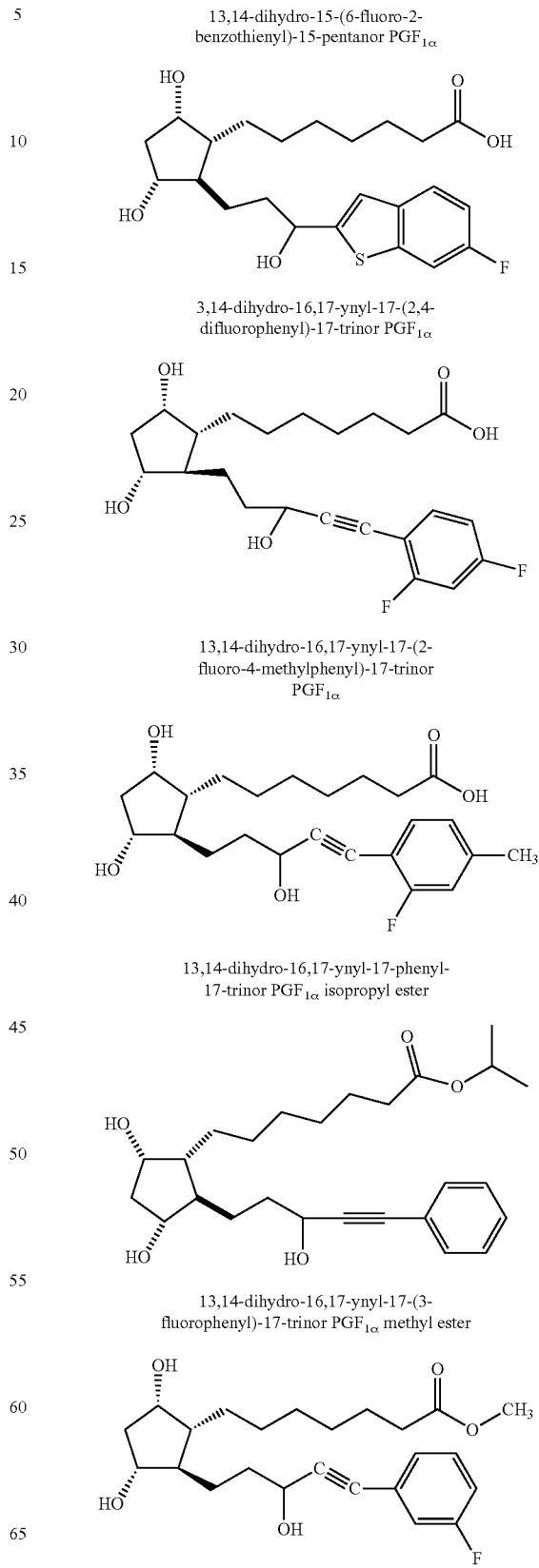

TABLE 2-continued

Examples of Suitable PGF's 13,14-dihydro-16,17-ynyl-17-(4-chlorophenyl)-17-trinor PGF$_{1\alpha}$

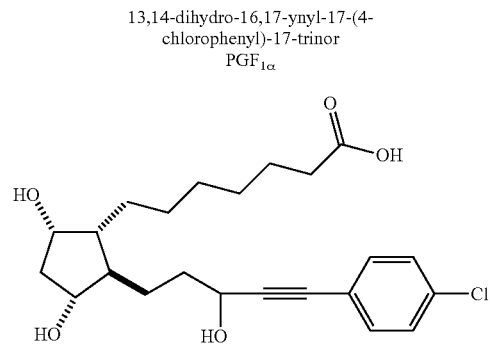

13,14-dihydro-16,17-ynyl-17-(4-fluorophenyl)-17-trinor PGF$_{1\alpha}$ ethyl ester

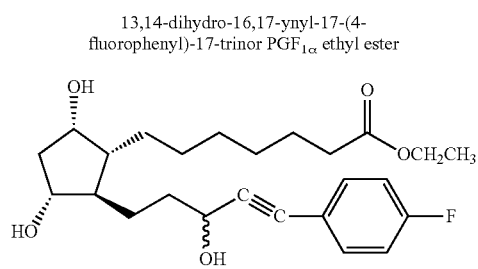

13,14-dihydro-15-(5-fluoro-2-benzothiazolyl)-15-pentanor PGF$_{1\alpha}$ isopropyl ester

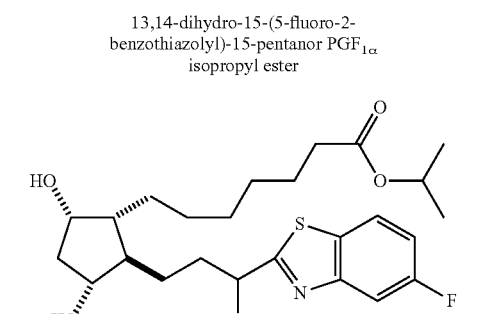

13,14-dihydro-16,17-ynyl-17-(2-fluorophenyl)-17-trinor PGF$_{1\alpha}$ methyl ester

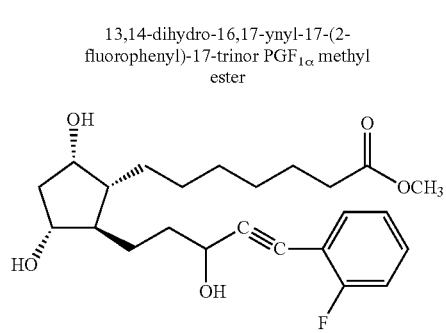

13,14-dihydro-16,17-ynyl-17-(4-phenyl-phenyl)-17-trinor PGF$_{1\alpha}$

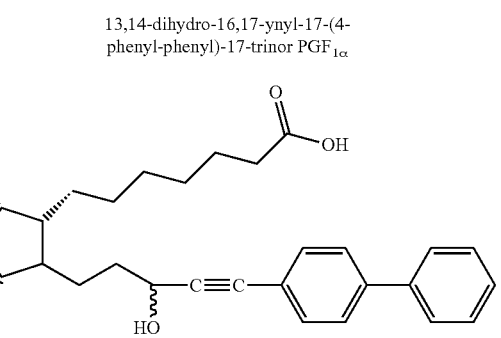

13,14-dihydro-16,17-ynyl-17-(2-chlorophenyl)-17-trinor PGF$_{1\alpha}$

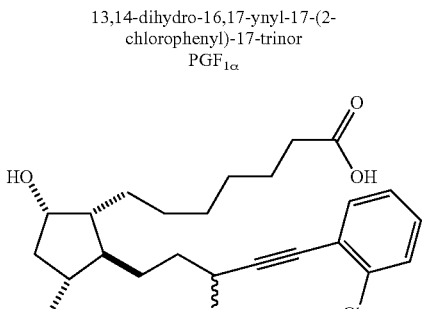

13,14-dihydro-16,17-ynyl-17-(2-fluorophenyl)-17-trinor PGF$_{1\alpha}$

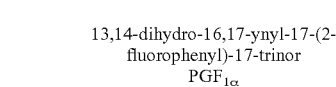

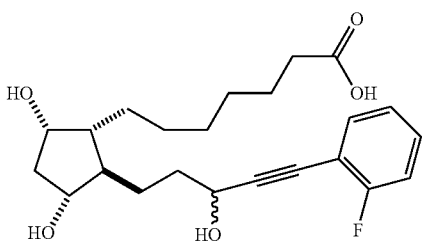 [SMILES: O=C(O)CCCCCC[C@@H]1[C@@H](CCC(O)C#Cc2ccccc2F)[C@H](O)C[C@@H]1O]

13,14-dihydro-16,17-ynyl-18-phenyl-18-dinor PGF$_{1\alpha}$

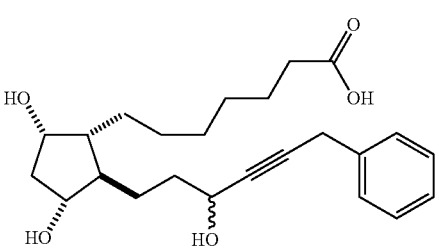 [SMILES: O=C(O)CCCCCC[C@@H]1[C@@H](CCC(O)C#CCc2ccccc2)[C@H](O)C[C@@H]1O]

13,14-dihydro-16,17-ynyl-17-(4-methylphenyl)-17-trinor PGF$_{1\alpha}$

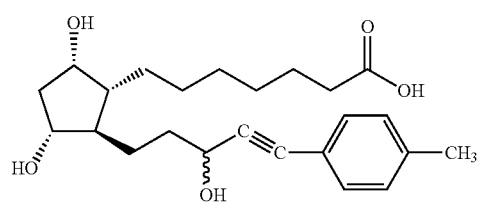 [SMILES: Cc1ccc(C#CC(O)CC[C@@H]2[C@@H](CCCCCCC(=O)O)[C@@H](O)C[C@H]2O)cc1]

13,14-dihydro-15-phenyl-15-pentanor PGF$_{1\alpha}$

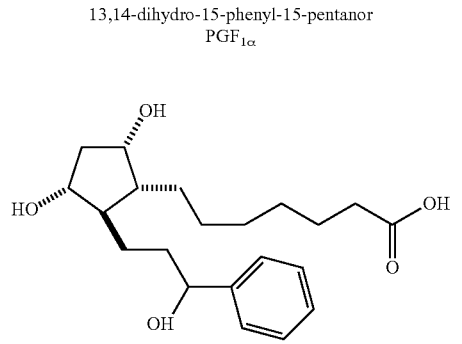

TABLE 2-continued

Examples of Suitable PGF's 13,14-dihydro-15-(4-trifluoromethylphenyl)-15-pentanor PGF$_{1\alpha}$

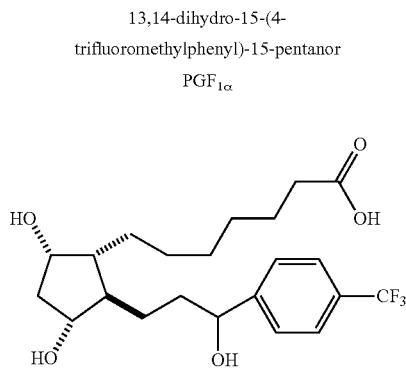

13,14-dihydro-16,17-ynyl-18-(2-fluorophenyl)-18-dinor PGF$_{1\alpha}$

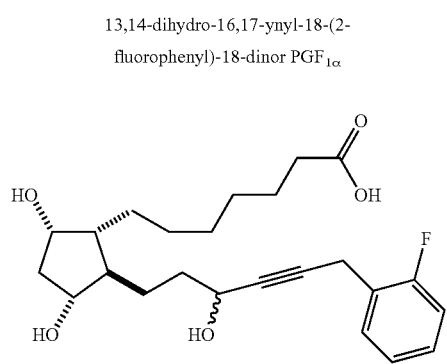

13,14-dihydro-15-(4-methylphenyl)-15-pentanor PGF$_{1\alpha}$

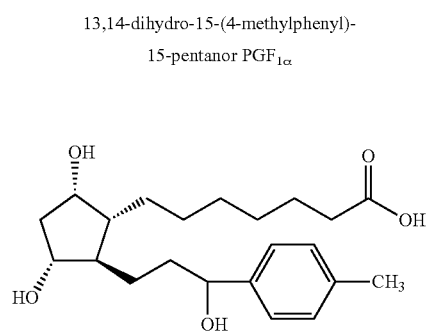

13,14-dihydro-15-(3-trifluoromethylphenyl)-15-pentanor PGF$_{1\alpha}$

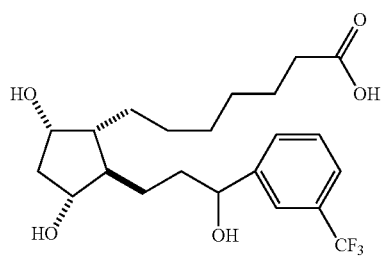 [SMILES: O=C(O)CCCCCC[C@@H]1[C@@H](CCC(O)c2cccc(C(F)(F)F)c2)[C@H](O)C[C@@H]1O]

TABLE 2-continued

Examples of Suitable PGF's 13,14-dihydro-15-(2-fluorophenyl)-15-pentanor PGF$_{1\alpha}$

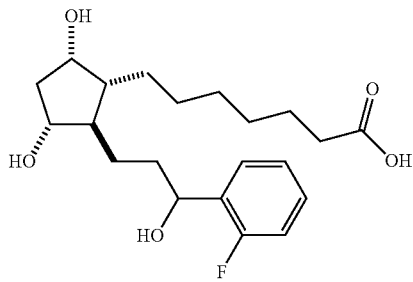 [SMILES: O=C(O)CCCCCC[C@@H]1[C@@H](CCC(O)c2ccccc2F)[C@H](O)C[C@@H]1O]

13,14-dihydro-15-(3-chloro-4-fluoro-6-methylphenyl)-15pentanor PGF$_{1\alpha}$

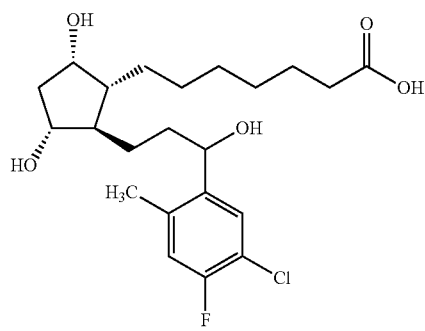 [SMILES: Cc1cc(F)c(Cl)cc1C(O)CC[C@@H]1[C@@H](CCCCCCC(=O)O)[C@@H](O)C[C@H]1O]

13,14-dihydro-15-(2-chlorophenyl)-15-pentanor PGF$_{1\alpha}$

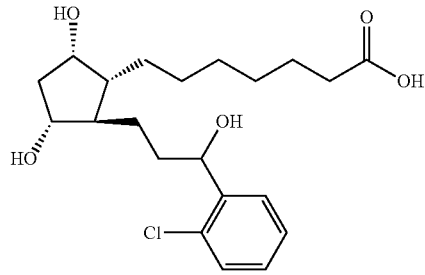 [SMILES: O=C(O)CCCCCC[C@@H]1[C@@H](CCC(O)c2ccccc2Cl)[C@H](O)C[C@@H]1O]

13,14-dihydro-15-(3,5 difluorophenyl)-15-pentanor PGF$_{1\alpha}$ ethyl ester

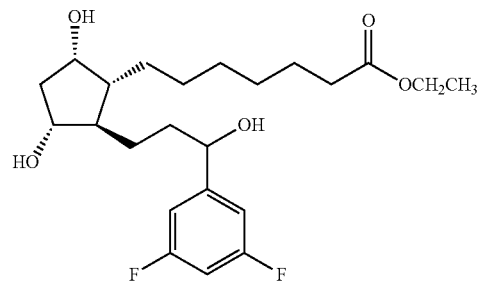 [SMILES: CCOC(=O)CCCCCC[C@@H]1[C@@H](CCC(O)c2cc(F)cc(F)c2)[C@H](O)C[C@@H]1O]

TABLE 2-continued

Examples of Suitable PGF's 13,14-dihydro-15-(3-pyridinyl)-15-pentanor PGF$_{1\alpha}$ 13,14-dihydro-15-(4-phenylphenyl)-15-pentanor PGF$_{1\alpha}$ methyl ester 13,14-dihydro-15-S-(2-fluorophenyl)-15-pentanor PGF$_{1\alpha}$ 13,14-dihydro-15-(3-fluoro-4-pyridyl)-15-pentanor PGF$_{1\alpha}$ isopropyl ester 13,14-dihydro-15-(benzo(b)thiophen-5-yl)-15-pentanor PGF$_{1\alpha}$

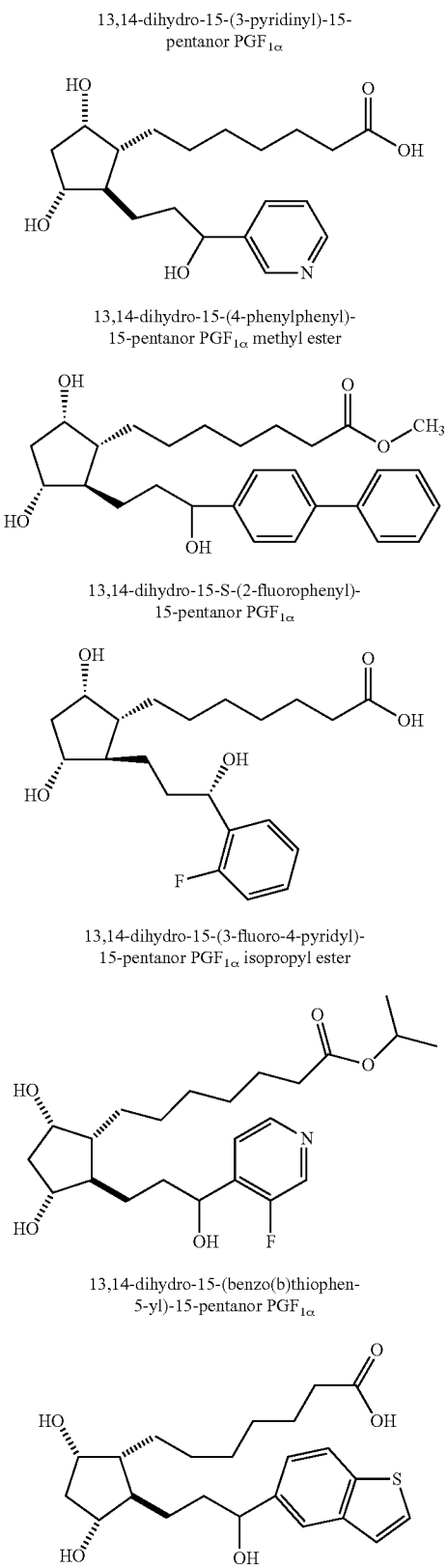

13,14-dihydro-15-S-(2-fluoronaphthyl)-15-pentanor PGF$_{1\alpha}$ 13,14-dihydro-15-(6-methylnaphth-2-yl)-15-pentanor PGF$_{1\alpha}$ 13,14-dihydro-15-(6-benzothiazol-5-yl)-15-pentanor PGF$_{1\alpha}$ 13,14-dihydro-15-(benzofuran-5-yl)-15-pentanor PGF$_{1\alpha}$ methyl ester

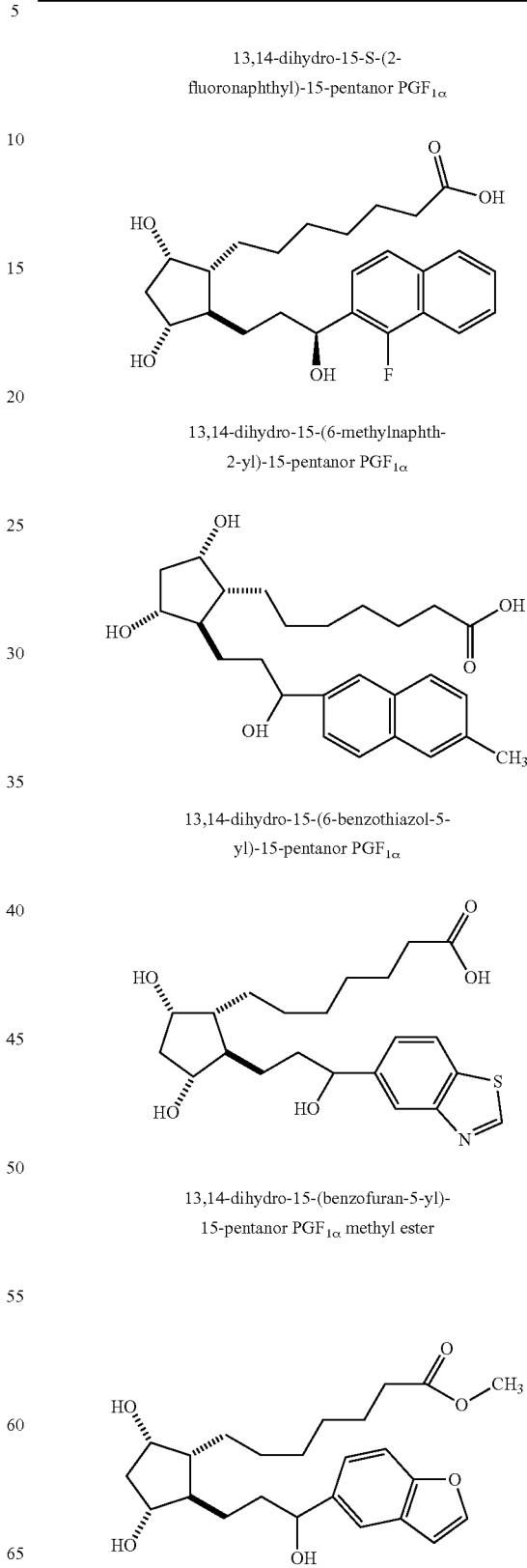

TABLE 2-continued

Examples of Suitable PGF's 13,14-dihydro-15-(8-fluoro-2-naphthyl)-15-pentanor PGF$_{1\alpha}$

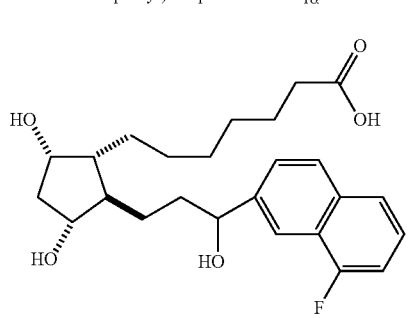

13,14-dihydro-15-(1-fluoro-3-trifluoromethyl-2-naphthyl)-15-pentanor PGF$_{1\alpha}$ isopropyl ester

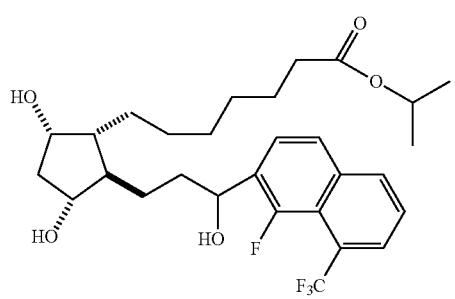 [SMILES: CC(C)OC(=O)CCCCCC[C@@H]1[C@@H](CCC(O)c2ccc3cccc(C(F)(F)F)c3c2F)[C@H](O)C[C@@H]1O]

13,14-dihydro-15-(5-fluoronaphth-1-yl)-15-pentanor PGF$_{1\alpha}$

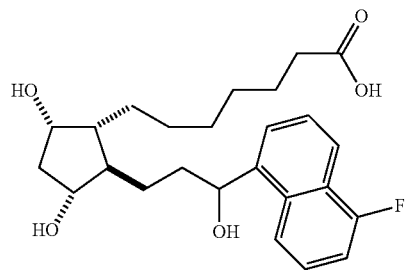

13,14-dihydro-15-(8-trifluoromethyl-2-naphthyl)-15-pentanor PGF$_{1\alpha}$

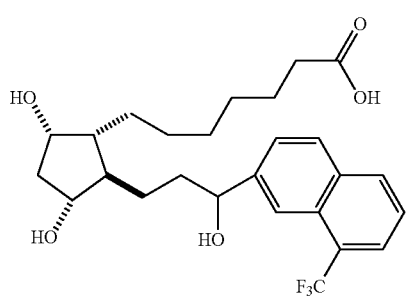 [SMILES: O=C(O)CCCCCC[C@@H]1[C@@H](CCC(O)c2ccc3cccc(C(F)(F)F)c3c2)[C@H](O)C[C@@H]1O]

TABLE 2-continued

Examples of Suitable PGF's 13,14-dihydro-16,17-ynyl-17-(2-fluorophenyl)-17-trinor PGF$_{1\alpha}$ 1-hydroxamic acid

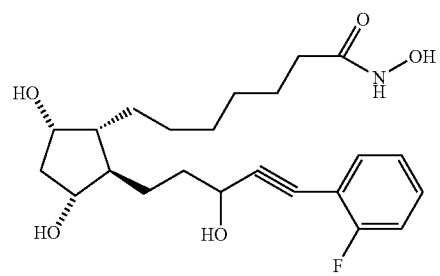 [SMILES: O=C(CCCCCC[C@@H]1[C@@H](CCC(O)C#Cc2ccccc2F)[C@H](O)C[C@@H]1O)NO]

13,14-dihydro-15-(benzothiazolyl)-15-pentanor PGF$_{1\alpha}$ 1-hydroxamic acid

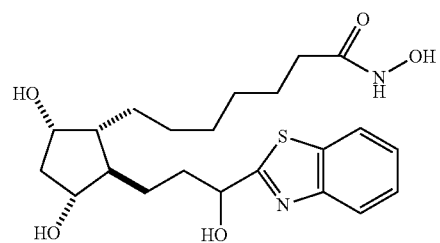 [SMILES: O=C(CCCCCC[C@@H]1[C@@H](CCC(O)c2nc3ccccc3s2)[C@H](O)C[C@@H]1O)NO]

13,14-dihydro-15-(4-fluoro-2-benzothienyl)-15-pentanor PGF$_{1\alpha}$ 1-hydroxamic acid

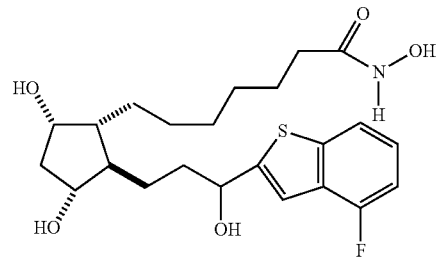 [SMILES: O=C(CCCCCC[C@@H]1[C@@H](CCC(O)c2cc3c(F)cccc3s2)[C@H](O)C[C@@H]1O)NO]

13,14-dihydro-15-(2-benzothienyl)-15-pentanor PGF$_{1\alpha}$ 1-N-methanesulfonamide

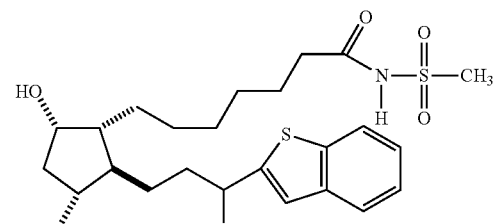

The PGF's in Table 2 can be prepared by conventional organic syntheses. A preferred synthesis is reaction scheme 4.

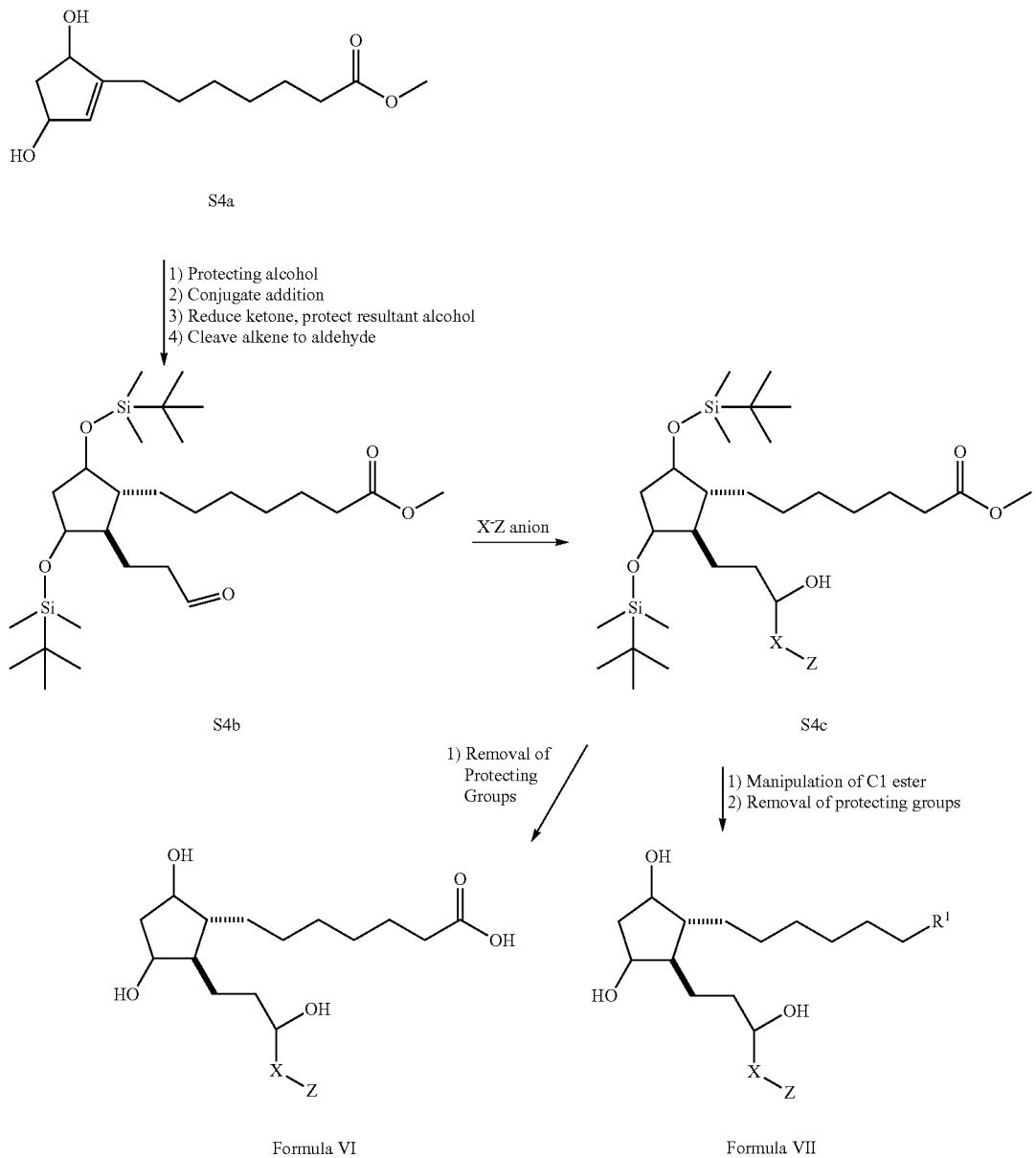

Scheme 4

S4a

S4b

S4c

Formula VI

Formula VII

In Scheme 4, $R^1$, $R^2$, X, and Z are as defined above. The methyl 7(3-(R)-hydroxy-5-oxo-1-cyclopent-1-yl) heptanoate (S4a) depicted as starting material for Scheme 4 is commercially available (such as from Sumitomo Chemical or Cayman Chemical).

The $C_{11}$ alcohol of methyl 7-(3-(R)-hydroxy-5-oxo-1-cyclopent-1-yl) heptanoate (S4a) is protected with a suitable protecting group. The most preferred protecting group is a silyl group. In the above Scheme 4, methyl 7-(3-(R)-hydroxy-5-oxo-1-cyclopent-1-yl) heptanoate (S4a) is reacted with a silylating agent and base in a solvent that will allow the silylation to proceed. Preferred silylating agents include tert-butyldimethylsilyl chloride and tert-butyldimethylsilyl trifluoromethanesulphonate. The most preferred silylating agent is tert-butyldimethylsilyl trifluoromethanesulphonate. Preferred bases include triethylamine, trimethylamine, and 2,6-lutidine. More preferred bases include triethylamine and 2,6-lutidine. The most preferred base is 2,6-lutidine. Preferred solvents include halogenated hydrocarbon solvents with dichloromethane being the most preferred solvent. The reaction is allowed to proceed at a temperature of preferably −100° C. to 100° C., more preferably −80° C. to 80° C., and most preferably −70° C. to 23° C.

The resulting silylated compound is isolated by methods known to those of ordinary skill in the art. Such methods include extraction, solvent evaporation, distillation, and crystallization. Preferably, the silyl ether is purified after isolation by distillation under vacuum.

The silylated compound is then reacted with the cuprate generated via Grignard formation of the appropriate alkenyl bromide as disclosed, for example, in the following references: H. O. House et. al., "The Chemistry of Carbanions: A Convenient Precursor for the Generation of Lithium Organocuprates", *J. Org. Chem.*, Vol. 40, pp. 1460-69 (1975); and P. Knochel et. al., "Zinc and Copper Carbenoids as Efficient and Selective a'/d' Multicoupling Reagents", *J. Amer. Chem. Soc.*, Vol. 111, p. 6474-76 (1989). Preferred alkenyl bromides include 4-bromo-1-butene, 4-bromo-1-butyne, 4-bromo-2-methyl-1-butene, and 4-bromo-2-ethyl-1-butene. The most preferred alkenyl bromide is 4-bromo-1-butene. Preferred solvents include ethereal solvents, of which diethyl ether and tetrahydrofuran are preferred. The most preferred solvent is tetrahydrofuran. The Grignard reagent is allowed to form at a temperature of 100° C. to 23° C., more preferably 85° C. to 30° C., and most preferably 75° C. to 65° C. The reaction time is preferably 1 to 6 hours, more preferably 2 to 5 hours, and most preferably 3 to 4 hours.

Once the Grignard reagent is formed, the cuprate is generated from the alkenyl magnesium species. The temperature range for cuprate formation is −100° C. and 0° C.

The preferred temperature range is −80° C. to −20° C., more preferably −75° C. to −50° C. The preferred reaction time is 30 minutes to 6 hours, more preferably 45 minutes to 3 hours, and most preferably 1 to 1.5 hours.

The alkene thus formed is isolated by methods known to one of ordinary skill in the art. Such methods include, but are not limited to, extraction, solvent evaporation, distillation, and crystallization. Preferably, the alkene is purified by flash chromatography on silica gel (Merck, 230-400 mesh) using 10% EtOAc/hexanes as the eluent. The alkene is then reacted with a hydride reducing agent and a polar, protic solvent to give the C-9 alcohol. Preferred reducing agents include lithium aluminum hydride, sodium borohydride, and L-selectride. More preferred reducing agents include sodium borohydride, and L-selectride. The most preferred reducing agent is sodium borohydride. Preferred solvents include methanol, ethanol, and butanol. The most preferred solvent is methanol. The reduction is carried out at a temperature between −100° C. and 23° C. The preferred temperature range is −60° C. to 0° C. The most preferred temperature range is −45° C. to −20° C.

The resulting alcohol is isolated by methods known to one of ordinary skill in the art. Such methods include, but are not limited to, extraction, solvent evaporation, distillation, and crystallization. Preferably, the alcohol is purified by flash chromatography on silica gel (Merck, 230-400 mesh) using 20% EtOAc/hexanes as the eluent.

The resultant alcohol can be protected as described previously herein. Preferred silylating agents in this case also include tert-butyldimethylsilyl chloride and tert-butyldimethylsilyl trifluoromethanesulfonate. The most preferred silylating agent is tert-butyldimethylsilyl trifluoromethanesulfonate. Preferred bases include triethylamine, trimethylamine, and 2,6-lutidine. More preferred bases include triethylamine and 2,6-lutidine. The most preferred base is 2,6-lutidine. Preferred solvents include halogenated hydrocarbon solvents with dichloromethane being the most preferred solvent. The reaction is allowed to proceed at a temperature of preferably −100° C. to 100° C., more preferably −80° C. to 80° C., and most preferably −70° C. to 23° C.

The resulting silylated compound is isolated by methods known to those of ordinary skill in the art. Such methods include, but are not limited to, extraction, solvent evaporation, distillation, and crystallization. Preferably, the silyl ether is purified after isolation by distillation under vacuum The protected or alcohol is then treated with a form of osmium, and sodium periodate in a solvent where they are both soluble. Preferred forms of osmium include osmium tetraoxide and potassium osmate. Preferred solvent systems include 1:1 mixtures of acetic acid and water and 1:1:2 mixtures of water, acetic acid and THF. The result of this treatment is the aldehyde, S4b.

The compound S4b is isolated by methods known to one of ordinary skill in the art. Such methods include, but are not limited to, extraction, solvent evaporation, distillation, and crystallization. Preferably, S4b is purified by flash chromatography on silica gel (Merck, 230-400 mesh) using 20% EtOAc/hexanes as the eluent.

The key intermediate aldehyde depicted as S4b can be reacted with a variety unsaturated carbon nucleophiles to provide the C-9 and C-11-protected 13,14-dihydro-16-tetranor prostaglandin $F_{1\alpha}$ derivatives depicted as S4c.

With alkyne nucleophiles, the reaction is carried out preferably at −80° C. to 0° C., more preferably −80° C. to −20° C., and most preferably −80° C. to −40° C. Preferred bases for the reaction include n-butyl lithium, s-butyl lithium, t-butyl lithium, and lithium diisopropyl amide ("LDA"). Preferred solvents for the reaction are ether solvents. Preferred solvents include diethyl ether, and tetrahydrofuran. The most preferred solvent is tetrahydrofuran. With heterocyclic nucleophiles, preferred solvents include ethereal solvents. More preferred ethereal solvents include diethyl ether, dibutyl ether and tetrahydrofuran. The most preferred ethereal solvent is tetrahydrofuran.

The resulting compounds depicted as S4c can then be deprotected using techniques known to one of ordinary skill in the art, and isolated yielding the 13,14-dihydro-15-substituted-15-pentanor prostaglandin $F_{1\alpha}$ derivatives depicted by Formula VI.

Compounds depicted by Formula VII can be made directly from the C-9 and C-11-protected 13,14-dihydro-16-tetranor prostaglandin $F_{1\alpha}$ derivatives depicted as S4c by methods known to one of ordinary skill in the art. For example, the condensation of methyl esters of S4c with amines or hydroxylamine provides compounds depicted by Formula VII. These compounds are isolated by methods known to one of ordinary skill in the art. Such methods include extraction, solvent evaporation, distillation, and crystallization.

Examples of PGF's having the structure:

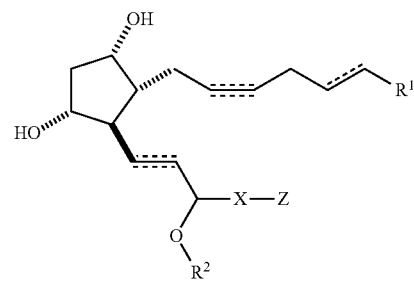

which are suitable for component A) include: cloprostenol (estrumate), fluprostenol (equimate), tiaprost, alfaprostol, delprostenate, froxiprost, 9-alpha, 11-alpha, 15-alpha-trihydroxy-16-(3-chlorophenoxy)-omega-tetranor-prosta-4-cis-13-trans-dienoic acid, latanoprost and their analogs; and 13,14-dihydro-16-((3-trifluoromethyl)phenoxy)-16-tetranor prostaglandin $F_{1\alpha}$, 17-((3-trifluoromethyl)phenyl)-17-trinor-prostaglandin $F_{2\alpha}$ and its analogs, 13,14-dihydro-18-thienyl-18-dinor prostaglandin $F_{1\alpha}$ and their analogs. Additional PGF's are also disclosed in *CRC Handbook of Eicosanoids: Prostaglandins and Related Lipids*, Volume I, Chemical and Biochemical Aspects, Part B. Ed. by Anthony L. Willis, CRC Press, Boca Raton, Table Four, pp. 80-97 (1987) and references therein.

Preferred PGF's of the present invention are further selective for the FP receptor over an excitatory prostaglandin receptor in a ratio of 1:10, preferably from 1:20, more preferably from 1:50.

Compositions of the Invention

This invention further relates to a composition for treating hair loss. "Treating hair loss" means arresting hair loss, reversing hair loss, or both, and promoting hair growth. The composition comprises component A) the PGF described above and component B) a carrier. The composition may further comprise component C) one or more optional activity enhancers.

The composition can be a pharmaceutical or cosmetic composition, administered for treatment or prophylaxis of hair loss. Standard pharmaceutical formulation techniques are used, such as those disclosed in *Remington's Pharmaceutical Sciences*, Mack Publishing Company, Easton, Pa. (1990).

The composition further comprises component B) a carrier. "Carrier" means one or more compatible substances that are suitable for administration to a mammal. Carrier includes solid or liquid diluents, hydrotopes, surface-active agents, and encapsulating substances. "Compatible" means that the components of the composition are capable of being commingled with the PGF's, and with each other, in a manner such that there is no interaction which would substantially reduce the efficacy of the composition under ordinary use situations. Carriers must be of sufficiently high purity and sufficiently low toxicity to render them suitable for administration to the mammal being treated. The carrier can be inert, or it can possess pharmaceutical benefits, cosmetic benefits, or both.

The choice of carrier for component B) depends on the route by which A) the PGF will be administered and the form of the composition. The composition may be in a variety of forms, suitable, for example, for systemic administration (e.g., oral, rectal, nasal, sublingual, buccal, or parenteral) or topical administration (e.g., local application on the skin, ocular, liposome delivery systems, or iontophoresis). Topical administration directly to the locus of desired hair growth is preferred.

Carriers for systemic administration typically comprise one or more ingredients selected from the group consisting of a) diluents, b) lubricants, c) binders, d) disintegrants, e) colorants, f) flavors, g) sweeteners, h) antioxidants, j) preservatives, k) glidants, m) solvents, n) suspending agents, o) surfactants, combinations thereof, and others.

Ingredient a) is a diluent. Suitable diluents include sugars such as glucose, lactose, dextrose, and sucrose; polyols such as propylene glycol; calcium carbonate; sodium carbonate; glycerin; mannitol; sorbitol; and maltodextrin.

Ingredient b) is a lubricant. Suitable lubricants are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma.

Ingredient c) is a binder. Suitable binders include polyvinylpyrrolidone; magnesium aluminum silicate; starches such as corn starch and potato starch; gelatin; tragacanth; and cellulose and its derivatives, such as sodium carboxymethylcellulose, ethylcellulose, methylcellulose, microcrystalline cellulose, and hydroxypropylmethylcellulose; carbomer; providone; acacia; guar gum; and xanthan gum.

Ingredient d) is a disintegrant. Suitable disintegrants include agar, alginic acid and the sodium salt thereof, effervescent mixtures, croscarmelose, crospovidone, sodium carboxymethyl starch, sodium starch glycolate, clays, and ion exchange resins.

Ingredient e) is a colorant such as an FD&C dye.

Ingredient f) is a flavor such as menthol, peppermint, and fruit flavors.

Ingredient g) is a sweetener such as saccharin and aspartame.

Ingredient h) is an antioxidant such as butylated hydroxyanisole, butylated hydroxytoluene, and vitamin E.

Ingredient j) is a preservative such as phenol, alkyl esters of parahydroxybenzoic acid, benzoic acid and the salts thereof, boric acid and the salts thereof, sorbic acid and the salts thereof, chorbutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben, and sodium benzoate.

Ingredient k) is a glidant such as silicon dioxide.

Ingredient m) is a solvent, such as water, isotonic saline, ethyl oleate, alcohols such as ethanol, glycerin, glycols (e.g., polypropylene glycol and polyethylene glycol), and buffer solutions (e.g., phosphate, potassium acetate, boric carbonic, phosphoric, succinic, malic, tartaric, citric, acetic, benzoic, lactic, glyceric, gluconic, glutaric and glutamic).

Ingredient n) is a suspending agent. Suitable suspending agents include AVICEL® RC-591 from FMC Corporation of Philadelphia, Pa. and sodium alginate.

Ingredient o) is a surfactant such as lecithin, polysorbate 80, sodium lauryl sulfate, polyoxyethylene sorbitan fatty acid esters, polyoxyethylene monoalkyl ethers, sucrose monoesters, lanolin esters, and lanolin ethers. Suitable surfactants are known in the art and commercially available, e.g., the TWEENS® from Atlas Powder Company of Wilmington, Del.

Compositions for parenteral administration typically comprise A) 0.1 to 10% of a PGF and B) 90 to 99.9% of a carrier comprising a) a diluent, and m) a solvent. Preferably, component a) is propylene glycol and m) is ethanol or ethyl oleate.

Compositions for oral administration can have various dosage forms. For example, solid forms include tablets, capsules, granules, and bulk powders. These oral dosage forms comprise a safe and effective amount, usually at least 5%, and preferably from 25% to 50%, of A) the PGF. The oral dosage compositions further comprise B) 50 to 95% of a carrier, preferably 50 to 75%.

Tablets can be compressed, tablet triturates, enteric-coated, sugar-coated, film-coated, or multiple-compressed. Tablets typically comprise A) the PGF, and B) a carrier comprising ingredients selected from the group consisting of a) diluents, b) lubricants, c) binders, d) disintegrants, e) colorants, f) flavors, g) sweeteners, k) glidants, and combinations thereof. Preferred diluents include calcium carbonate, sodium carbonate, mannitol, lactose and cellulose. Preferred binders include starch, gelatin, and sucrose. Preferred disintegrants include alginic acid, and croscarmelose. Preferred lubricants include magnesium stearate, stearic acid, and talc. Preferred colorants are the FD&C dyes, which can be added for appearance. Chewable tablets preferably contain g) sweeteners such as aspartame and saccharin, or f) flavors such as menthol, peppermint, and fruit flavors.

Capsules (including time release and sustained release formulations) typically comprise A) the PGF, and B) a carrier comprising one or more a) diluents disclosed above in a capsule comprising gelatin. Granules typically comprise A) the PGF, and preferably further comprise k) glidants such as silicon dioxide to improve flow characteristics.

The selection of ingredients in the carrier for oral compositions depends on secondary considerations like taste, cost, and shelf stability, which are not critical for the purposes of this invention. One skilled in the art can optimize appropriate ingredients without undue experimentation.

The solid compositions may also be coated by conventional methods, typically with pH or time-dependent coatings, such that A) the PGF is released in the gastrointestinal tract at various times to extend the desired action. The coatings typically comprise one or more components selected from the group consisting of cellulose acetate phthalate, polyvinylacetate phthalate, hydroxypropyl methyl cellulose phthalate, ethyl cellulose, acrylic resins such as EUDRAGIT® coatings (available from Rohm & Haas G.M.B.H. of Darmstadt, Germany), waxes, shellac, polyvinylpyrrolidone, and other commercially available film-coating preparations such as Dri-Klear, manufactured by Crompton & Knowles Corp., Mahwah, N.J. or OPADRY® manufactured by Colorcon, Inc., of West Point, Pa.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise A) the PGF and B) a carrier comprising ingredients selected from the group consisting of a) diluents, e) colorants, and f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject compounds include sublingual, buccal and nasal dosage forms. Such compositions typically comprise one or more soluble filler substances such as a) diluents including sucrose, sorbitol and mannitol; and c) binders such as acacia, microcrystalline cellulose, carboxymethylcellulose, and hydroxypropylmethylcellulose. Such compositions may further comprise b) lubricants, e) colorants, f) flavors, g) sweeteners, h) antioxidants, and k) glidants.

The compositions may further comprise component C) an optional activity enhancer. Component C) is preferably selected from the group consisting of i) hair growth stimulants (other than the PGF) and ii) penetration enhancers.

Component i) is an optional hair growth stimulant. Component i) is exemplified by vasodilators, antiandrogens, cyclosporins, cyclosporin analogs, antimicrobials, anti-inflammatories, thyroid hormones, thyroid hormone derivatives, and thyroid hormone analogs, non-selective prostaglandin agonists or antagonists, retinoids, triterpenes, combinations thereof, and others. "Non-selective prostaglandin" agonists and antagonists differ from component A) in that they do not selectively activate the FP receptor, and they may activate other receptors.

Vasodilators such as potassium channel agonists including minoxidil and minoxidil derivatives such as aminexil and those described in U.S. Pat. Nos. 3,382,247, 5,756,092, 5,772,990, 5,760,043, 5,466,694, 5,438,058, 4,973,474, and cromakalin and diazoxide can be used as optional hair growth stimulants in the composition.

Examples of suitable antiandrogens include 5-α-reductase inhibitors such as finasteride and those described in U.S. Pat. No. 5,516,779, and in Nane et al., *Cancer Research* 58, "Effects of Some Novel Inhibitors of C17,20-Lyase and 5α-Reductase in vitro and in vivo and Their Potential Role in the Treatment of Prostate Cancer," as well as cyproterone acetate, azelaic acid and its derivatives and those compounds described in U.S. Pat. No. 5,480,913, flutamide, and those compounds described in U.S. Pat. Nos. 5,411,981, 5,565,467, and 4,910,226.

Antimicrobials include selenium sulfide, ketoconazole, triclocarbon, triclosan, zinc pyrithione, itraconazole, asiatic acid, hinokitiol, mipirocin and those described in EPA 0,680, 745, clinacycin hydrochloride, benzoyl peroxide, benzyl peroxide and minocyclin.

Examples of suitable anti-inflammatories include glucocorticoids such as hydrocortisone, mometasone furoate and prednisolone, nonsteroidal anti-inflammatories including cyclooxygenase or lipoxygenase inhibitors such as those described in U.S. Pat. No. 5,756,092, and benzydamine, salicylic acid, and those compounds described in EPA 0,770,399, published May 2, 1997, WO 94/06434, published Mar. 31, 1994, and FR 2,268,523, published Nov. 21, 1975.

3,5,3'-Triiodothyronine is an example of a suitable thyroid hormone.

Examples of suitable non-selective prostaglandins agonists and antagonists include compounds such as those described in WO 98/33497, Johnstone, published Aug. 6, 1998, WO 95/11003, Stjernschantz, published Apr. 27, 1995, JP 97-100091, Ueno and JP 96-134242, Nakamura.

Suitable retinoids include isotretinoin, acitretin, and tazarotene.

Other optional hair growth stimulants for component i) include benzalkonium chloride, benzethonium chloride, phenol, estradiol, chlorpheniramine maleate, chlorophyllin derivatives, cholesterol, salicylic acid, cysteine, methionine, red pepper tincture, benzyl nicotinate, D,L-menthol, peppermint oil, calcium pantothenate, panthenol, castor oil, prednisolone, resorcinol, chemical activators of protein kinase C, glycosaminoglycan chain cellular uptake inhibitors, inhibitors of glycosidase activity, glycosaminoglycanase inhibitors, esters of pyroglutamic acid, hexosaccharic acids or acylated hexosaccharic acids, aryl-substituted ethylenes, N-acylated amino acids, flavinoids, ascomycin derivatives and analogs, histamine antagonists such as diphenhydramine hydrochloride, triterpenes such as oleanolic acid and ursolic acid and those described in U.S. Pat. Nos. 5,529,769, 5,468, 888, 5,631,282, and 5,679,705, JP 10017431, WO 95/35103, JP 09067253, WO 92/09262, JP 62093215, and JP 08193094; saponins such as those described in EP 0,558,509 to Bonte et al., published Sep. 8, 1993 and WO 97/01346 to Bonte et al, published Jan. 16, 1997, proteoglycanase or glycosaminoglycanase inhibitors such as those described in U.S. Pat. Nos. 5,015,470, 5,300,284, and 5,185,325, estrogen agonists and antagonists, pseudoterins, cytokine and growth factor promoters, analogs or inhibitors such as interleukin1 inhibitors, interleukin-6 inhibitors, interleukin-10 promoters, and tumor necrosis factor inhibitors, vitamins such as vitamin D analogs and parathyroid hormone antagonists, Vitamin B12 analogs and panthenol, interferon agonists and antagonists, hydroxy-acids such as those described in U.S. Pat. No. 5,550,158, benzophenones, and hydantoin anticonvulsants such as phenyloin, and combinations thereof.

Other additional hair growth stimulants are described in JP 09-157,139 to Tsuji et al., published Jun. 17, 1997; EP 0277455 A1 to Mirabeau, published Aug. 10, 1988; WO 97/05887 to Cabo Soler et al., published Feb. 20, 1997; WO 92/16186 to Bonte et al., published Mar. 13, 1992; JP 62-93215 to Okazaki et al., published Apr. 28, 1987; U.S. Pat. No. 4,987,150 to Kurono et al., issued Jan. 22, 1991; JP 290811 to Ohba et al., published Oct. 15, 1992; JP 05-286, 835 to Tanaka et al., published Nov. 2, 1993, FR 2,723,313 to Greff, published Aug. 2, 1994, U.S. Pat. No. 5,015,470 to Gibson, issued May 14, 1991, U.S. Pat. No. 5,559,092, issued Sep. 24, 1996, U.S. Pat. No. 5,536,751, issued Jul. 16, 1996, U.S. Pat. No. 5,714,515, issued Feb. 3, 1998, EPA 0,319,991, published Jun. 14, 1989, EPA 0,357,630, published Oct. 6, 1988, EPA 0,573,253, published Dec. 8, 1993, JP 61-260010, published Nov. 18, 1986, U.S. Pat. No. 5,772,990, issued Jun. 30, 1998, U.S. Pat. No. 5,053,410, issued Oct. 1, 1991, and U.S. Pat. No. 4,761,401, issued Aug. 2, 1988.

The most preferred activity enhancers are minoxidil and finasteride, most preferably minoxidil.

Component ii) is a penetration enhancer that can be added to all of the compositions for systemic administration. The amount of component ii), when present in the composition, is typically 1 to 5%. Examples of penetration enhancers include 2-methyl propan-2-ol, propan-2-ol, ethyl-2-hydroxypropanoate, hexan-2,5-diol, polyoxyethylene(2) ethyl ether, di(2-hydroxypropyl)ether, pentan-2,4-diol, acetone, polyoxyethylene(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, polyoxyethylene ester of oleyl alcohol, oleyl alcohol, lauryl alcohol, dioctyl adipate, dicapryl adipate, di-isopropyl adipate, diisopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethylhexyl pelargonate, isopropyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hydroxyoctanoic acid, dimethyl sulphoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one, omega three fatty acids and fish oils, and combinations thereof.

In a preferred embodiment of the invention, the PGF's are topically administered. Topical compositions that can be applied locally to the skin may be in any form including solutions, oils, creams, ointments, gels, lotions, shampoos, leave-on and rinse-out hair conditioners, milks, cleansers, moisturizers, sprays, skin patches, and the like. Topical compositions comprise: component A) the PGF described above and component B) a carrier. The carrier of the topical composition preferably aids penetration of the PGF's into the skin to reach the environment of the hair follicle. Topical compositions preferably further comprise C) one or more of the optional activity enhancers described above.

The exact amounts of each component in the topical composition depend on various factors. The amount of component A) depends on the $IC_{50}$ of the PGF selected. "$IC_{50}$" means inhibitory concentration $50^{th}$ percentile. The amount of component A) added to the topical composition is:

$$IC_{50} \times 10^{-2} \geq \% \text{ of component } A) \geq IC_{50} \times 10^{-3},$$

where $IC_{50}$ is expressed in nanomolar units. For example, if the $IC_{50}$ of the PGF is 1 nM, the amount of component A) will be 0.001 to 0.01%. If the $IC_{50}$ of the PGF is 10 nM, the amount of component A) will be 0.01 to 0.1%. If the $IC_{50}$ of the PGF is 100 nM, the amount of component A) will be 0.1 to 1.0%. If the $IC_{50}$ of the PGF is 1000 nM, the amount of component A) will be 1.0 to 10%, preferably 1.0 to 5%. If the amount of component A) is outside the ranges specified above (i.e., either higher or lower), efficacy of the treatment may be reduced. $IC_{50}$ can be calculated according to the method in Reference Example 1, below. One skilled in the art can calculate $IC_{50}$ without undue experimentation.

The topical composition preferably further comprises 1 to 20% component C), and a sufficient amount of component B) such that the amounts of components A), B), and C), combined equal 100%. The amount of B) the carrier employed in conjunction with the PGF is sufficient to provide a practical quantity of composition for administration per unit dose of the compound. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Component B) the carrier may comprise a single ingredient or a combination of two or more ingredients. In the topical compositions, component B) is a topical carrier. Preferred topical carriers comprise one or more ingredients selected from the group consisting of water, alcohols, aloe vera gel, allantoin, glycerin, vitamin A and E oils, mineral oil, propylene glycol, polypropylene glycol-2 myristyl propionate, dimethyl isosorbide, combinations thereof, and the like. More preferred carriers include propylene glycol, dimethyl isosorbide, and water.

The topical carrier may comprise one or more ingredients selected from the group consisting of q) emollients, r) propellants, s) solvents, t) humectants, u) thickeners, v) powders, and w) fragrances in addition to, or instead of, the preferred topical carrier ingredients listed above. One skilled in the art would be able to optimize carrier ingredients for the topical compositions without undue experimentation.

Ingredient q) is an emollient. The amount of ingredient q) in the topical composition is typically 5 to 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petrolatum, mineral oil, butyl myristate, isostearic acid, palmitic acid, isopropyl linoleate, lauryl lactate, myristyl lactate, decyl oleate, myristyl myristate, polydimethylsiloxane, and combinations thereof. Preferred emollients include stearyl alcohol and polydimethylsiloxane.

Ingredient r) is a propellant. The amount of ingredient r) in the topical composition is typically 5 to 95%. Suitable propellants include propane, butane, isobutane, dimethyl ether, carbon dioxide, nitrous oxide, and combinations thereof.

Ingredient s) is a solvent. The amount of ingredient s) in the topical composition is typically 5 to 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Preferred solvents include ethyl alcohol.

Ingredient t) is a humectant. The amount of ingredient t) in the topical composition is typically 5 to 95%. Suitable humectants include glycerin, sorbitol, sodium 2-pyrrolidone-5-carboxylate, soluble collagen, dibutyl phthalate, gelatin, and combinations thereof. Preferred humectants include glycerin.

Ingredient u) is a thickener. The amount of ingredient u) in the topical composition is typically 0 to 95%.

Ingredient v) is a powder. The amount of ingredient v) in the topical composition is typically 0 to 95%. Suitable powders include chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate, and combinations thereof.

Ingredient w) is a fragrance. The amount of ingredient w) in the topical composition is typically 0.001 to 0.5%, preferably 0.001 to 0.1%.

Component C) the optional activity enhancer is as described above. Any of the i) hair growth stimulants and ii) penetration enhancers may be added to the topical compositions. Preferably, the topical composition comprises 0.01 to 15% of component i) the optional hair growth stimulant. More preferably, the composition comprises 0.1 to 10%, and most preferably 0.5 to 5% of component i). Preferably, the topical composition comprises 1 to 5% of component ii).

In an alternative embodiment of the invention, topical pharmaceutical compositions for ocular administration are prepared by conventional methods. Topical pharmaceutical compositions for ocular administration typically comprise A) a PGF, B) a carrier, such as purified water, and one or more ingredients selected from the group consisting of y) sugars such as dextrans, particularly dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethyl cellulose, ethyl cellulose, methyl cellulose, and hydroxypropylmethylcellulose. Hydroxypropylmethylcellulose is preferred.

Examples of aa) salts suitable for use in the for use in the topical pharmaceutical composition for ocular administration include sodium chloride, potassium chloride, and combinations thereof.

Examples of cc) pH adjusting additives include HCl or NaOH in amounts sufficient to adjust the pH of the topical pharmaceutical composition for ocular administration to 7.2-7.5.

This invention further relates to a method for darkening hair, thickening hair, and reversing hair graying. The method comprises applying the topical composition for treating hair loss to hair, to skin in the locus of hair, or both. For example, the topical composition may be applied to hair growing on the scalp or eyelashes. The topical composition can be, for example, a cosmetic composition prepared as described above. An example of a composition that may be applied to eyelashes is a mascara. The PGF may be added to mascara compositions known in the art, such as the mascara described in U.S. Pat. No. 5,874,072, which is hereby incorporated by reference. The mascara further comprises dd) a water-insoluble material, ee) a water-soluble, film-forming polymer, ff) a wax, o) a surfactant, gg) a pigment, and s) a solvent.

Ingredient dd) is a water-insoluble material selected from the group consisting of acrylate copolymers; styrene/acrylate/methacrylate copolymers; acrylic latex; styrene/acrylic ester copolymer latex; polyvinylacetate latex; vinyl acetate/ethylene copolymer latex; styrene/butadiene copolymer latex; polyurethane latex; butadiene/acrylonitrile copolymer latex; styrene/acrylate/acrylonitrile copolymer latex; and mixtures thereof, wherein the acrylate copolymers, and the styrene/acrylate/methacrylate copolymers additionally comprise ammonia, propylene glycol, a preservative and a surfactant.

Ingredient ee) is a water-soluble, film-forming polymer. Ingredient ee) is selected from the group consisting of vinyl alcohol/poly(alkyleneoxy)acrylate, vinyl alcohol/vinyl acetate/poly-(alkyleneoxy)acrylate, polyethylene oxide, polypropylene oxide, acrylates/octyl-acrylamide copolymers and mixtures thereof.

Ingredient ff) is a wax. "Wax" means a lower-melting organic mixture or compound of high molecular weight, solid at room temperature and generally similar in composition to fats and oils except that they contain no glycerides. Some are hydrocarbons, others are esters of fatty acids and alcohols. Waxes useful in this invention are selected from the group consisting of animal waxes, vegetable waxes, mineral waxes, various fractions of natural waxes, synthetic waxes, petroleum waxes, ethylenic polymers, hydrocarbon types such as Fischer-Tropsch waxes, silicone waxes, and mixtures thereof wherein the waxes have a melting point between 55 and 100° C.

Ingredient o) is surfactant, as described above. Ingredient o) in the mascara is preferably a surfactant having an HLB from 3 to 15. Suitable surfactants include those disclosed in the *C.T.F.A. Cosmetic Ingredient Handbook*, pp. 587-592 (1992); *Remington's Pharmaceutical Sciences*, 15th ed., pp. 335-337 (1975); and *McCutcheon's Volume 1, Emulsifiers & Detergents*, North American Edition, pp. 236-239 (1994).

Ingredient gg) is a pigment. Suitable pigments include inorganic pigments, organic lake pigments, pearlescent pigments, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510); and mixtures thereof.

The organic pigments and lakes useful in this invention include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), and the dye or lakes based on Cochineal Carmine (CI 75,570), and mixtures thereof.

The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

Ingredient s) is a solvent described above, preferably water.

The amount of A) the PGF added to the mascara is as described above for topical compositions.

The PGF's may also be administered in the form of liposome delivery systems, such as small unilamellar vesicles, large unilamellar vesicles, and multilamellar vesicles.

Liposomes can be formed from a variety of phospholipids, such as cholesterol, stearylamine or phosphatidylcholines. A preferred formulation for topical delivery of the present compounds uses liposomes as described in Dowton et al., "Influence of Liposomal Composition on Topical Delivery of Encapsulated Cyclosporin A: I. An in vitro Study Using Hairless Mouse Skin", S.T.P. Pharma Sciences, Vol. 3, pp. 404-407 (1993); Wallach and Philippot, "New Type of Lipid Vesicle: Novasome®", Liposome Technology, Vol. 1, pp. 141-156 (1993); Wallach, U.S. Pat. No. 4,911,928, assigned to Micro-Pak, Inc., issued Mar. 27, 1990; and Weiner et al., U.S. Pat. No. 5,834,014, assigned to The University of Michigan and Micro-Pak, Inc., issued Nov. 10, 1998 (with respect to Weiner et al., with a compound as described herein administered in lieu of, or in addition to, minoxidil).

The PGF's may also be administered by iontophoresis. See, e.g., Internet site www.unipr.it/arpa/dipfarm/erasmus/erasml4.html; Banga et al., "Hydrogel-based Iontotherapeutic Delivery Devices for Transdermal Delivery of Peptide/Protein Drugs", Pharm. Res., Vol. 10 (5), pp. 697-702 (1993); Ferry, "Theoretical Model of Iontophoresis Utilized in Transdermal Drug Delivery", Pharmaceutical Acta Helvetiae, Vol 70, pp. 279-287 (1995); Gangarosa et al., "Modern Iontophoresis for Local Drug Delivery", Int. J. Pharm., Vol. 123, pp. 159-171 (1995); Green et al., "Iontophoretic Delivery of a Series of Tripeptides Across the Skin in vitro", Pharm. Res., Vol 8, pp. 1121-1127 (1991); Jadoul et al., "Quantification and Localization of Fentanyl and TRH Delivered by Iontophoresis in the Skin", Int. J. Pharm., Vol. 120, pp. 221-8 (1995); O'Brien et al., "An Updated Review of its Antiviral Activity, Pharmacokinetic Properties and Therapeutic Efficacy", Drugs, Vol. 37, pp. 233-309 (1989); Parry et al., "Acyclovir Bioavailability in Human Skin", J. Invest. Dermatol., Vol. 98 (6), pp. 856-63 (1992); Santi et al., "Drug Reservoir Composition and Transport of Salmon Calcitonin in Transdermal Iontophoresis", Pharm. Res., Vol 14 (1), pp. 63-66 (1997); Santi et al., "Reverse Iontophoresis—Parameters Determining Electroosmotic Flow: I. pH and Ionic Strength", J. Control. Release, Vol. 38, pp. 159-165 (1996); Santi et al., "Reverse Iontophoresis—Parameters Determining Electroosmotic Flow: II. Electrode Chamber Formulation", J. Control. Release, Vol. 42, pp. 29-36 (1996); Rao et al., "Reverse Iontophoresis: Noninvasive Glucose Monitoring in vivo in Humans", Pharm. Res., Vol. 12 (12), pp. 1869-1873 (1995); Thysman et al., "Human Calcitonin Delivery in Rats by Iontophoresis", J. Pharm. Pharmacol., Vol. 46, pp. 725-730 (1994); and Volpato et al., "Iontophoresis Enhances the Transport of Acyclovir through Nude Mouse Skin by Electrorepulsion and Electroosmosis", Pharm. Res., Vol. 12 (11), pp. 1623-1627 (1995).

The PGF's may be included in kits comprising a PGF, a systemic or topical composition described above, or both; and information, instructions, or both that use of the kit will provide treatment for hair loss in mammals (particularly humans). The information and instructions may be in the form of words, pictures, or both, and the like. In addition or in the alternative, the kit may comprise a PGF, a composition, or both; and information, instructions, or both, regarding methods of application of the PGF or composition, preferably with the benefit of treating hair loss in mammals.

Methods of the Invention

This invention further relates to a method for treating hair loss in mammals. The method comprises administering to a mammal (preferably a human) suffering from hair loss, a PGF described above. For example, a mammal diagnosed with alopecia including male pattern baldness and female pattern baldness can be treated by the methods of this invention. Preferably, a systemic or topical composition comprising A) the PGF and B) a carrier is administered to the mammal. More preferably, the composition is a topical composition comprising A) the PGF, B) the carrier, and C) an optional activity enhancer.

The dosage of the PGF administered depends on the method of administration. For systemic administration, (e.g., oral, rectal, nasal, sublingual, buccal, or parenteral), typically, 0.5 mg to 300 mg, preferably 0.5 mg to 100 mg, more preferably 0.1 mg to 10 mg, of a PGF described above is administered per day. These dosage ranges are merely exemplary, and daily administration can be adjusted depending on various factors. The specific dosage of the PGF to be administered, as well as the duration of treatment, and whether the treatment is topical or systemic are interdependent. The dosage and treatment regimen will also depend upon such factors as the specific PGF used, the treatment indication, the efficacy of the compound, the personal attributes of the subject (such as, for example, weight, age, sex, and medical condition of the subject), compliance with the treatment regimen, and the presence and severity of any side effects of the treatment.

For topical administration (e.g., local application on the skin, ocular, liposome delivery systems, or iontophoresis), the topical composition is typically administered once per day. The topical compositions are administered daily for a relatively short amount of time (i.e., on the order of weeks). Generally, 6 to 12 weeks is sufficient. The topical compositions are preferably leave-on compositions. In general, the topical composition should not be removed for at least several hours after administration.

In addition to the benefits in treating hair loss, the inventors have surprisingly found that the PGF's in the compositions and methods of this invention also darken and thicken hair and may reverse hair graying. This invention further relates to a method for darkening and thickening hair. The method comprises applying the topical composition for treating hair loss to growing hair and skin in the locus of the growing hair. In a preferred embodiment of the invention, the topical composition, such as the mascara composition described above, is applied to eyelashes.

EXAMPLES

These examples are intended to illustrate the invention to those skilled in the art and should not be interpreted as limiting the scope of the invention set forth in the claims.

Reference Example 1

Radioligand Binding Assay $IC_{50}$ of a PGF can be determined relative to $PGF_{2\alpha}$ using the Radioligand Binding Assay. As a control, the $IC_{50}$ for $PGF_{2\alpha}$ itself should be no lower than 1.0 nM and no higher than 5.0 nM.

In this assay, COS-7 cells are transiently transfected with the hFP recombinant plasmid using LipofectAMINE Reagent. Forty-eight hours later, the tranfected cells are washed with Hank's Balanced Salt Solution (HBSS, without $CaCl_2$, $MgCl_2$, $MgSO_4$, or phenol red). The cells are detached with versene, and HBSS is added. The mixture is centrifuged at 200 g for 10 minutes, at 4° C. to pellet the cells. The pellet is resuspended in Phosphate-Buffered Saline-EDTA buffer (PBS; 1 mM EDTA; pH 7.4; 4° C.). The cells are disrupted by nitrogen cavitation (Parr model 4639), at 800 psi, for 15 minutes at 4° C. The mixture is centrifuged at 1000 g for 10 minutes at 4° C. The supernatant is centrifuged at 100,000 g for 60 minutes at 4° C. The pellet is resuspended to 1 mg protein/mL TME buffer (50 mM Tris; 10 mM $MgCl_2$; 1 mM EDTA; pH 6.0; 4° C.) based on protein levels measured using the Pierce BCA Protein Assay kit. The homogenate is mixed for 10 seconds using a Kinematica POLYTRON® (available from KINEMATICA AG, Luzernerstrassel47A CH-6014 Littau, Switzerland). The membrane preparations are then stored at −80° C., until thawed for assay use.

The receptor competition binding assays are developed in a 96 well format. Each well contains 100 g of hFP membrane, 5 nM (3H) PGF2, and the various competing compounds in a total volume of 200 L. The plates are incubated at 23° C. for 1 hour. The incubation is terminated by rapid filtration using the Packard Filtermate 196 harvester through Packard UNI-FILTER® GF/B filters (available from Packard Instrument Co., Inc. of Downers Grove Ill.) pre-wetted with TME buffer. The filter is washed four times with TME buffer. Packard Microscint 20, a high efficiency liquid scintillation cocktail, is added to the filter plate wells and the plates remain at room temperature for three hours prior to counting. The plates are read on a Packard TOPCOUNT® Microplate Scintillation Counter (also available from Packard Instrument Co., Inc.)

Reference Example 2

Telogen Conversion Assay

PGF's are tested for their potential to grow hair using the Telogen Conversion Assay. The Telogen Conversion Assay measures the potential of a PGF to convert mice in the resting stage of the hair growth cycle ("telogen"), to the growth stage of the hair growth cycle ("anagen").

Without intending to be limited by theory, there are three principal phases of the hair growth cycle: anagen, catagen, and telogen. It is believed that there is a longer telogen period in C3H mice (Harlan Sprague Dawley, Inc., Indianapolis, Ind.) from approximately 40 days of age until about 75 days of age, when hair growth is synchronized. It is believed that after 75 days of age, hair growth is no longer synchronized. Wherein about 40 day-old mice with dark fur (brown or black) are used in hair growth experiments, melanogenesis occurs along with hair (fur) growth wherein the topical application of hair growth inducers are evaluated. The Telogen Conversion Assay herein is used to screen PGF's for potential hair growth by measuring melanogenesis.

Three groups of 44 day-old C3H mice are used: a vehicle control group, a positive control group, and a test PGF group, wherein the test PGF group is administered a PGF used in the method of this invention. The length of the assay is 24 days with 15 treatment days (wherein the treatment days occur Mondays through Fridays). Day 1 is the first day of treatment. A typical study design is shown in Table 3 below. Typical dosage concentrations are set forth in Table 3, however the skilled artisan will readily understand that such concentrations may be modified.

TABLE 3

Assay Parameters

| Group # | Animal # | Compound | Concentration | Application volume | Length of Study |
|---|---|---|---|---|---|
| 1 | 1-10 | Test Compound | 0.01% in vehicle** | 400 μL topical | 26 days |
| 2 | 11-20 | Positive Control (T3)* | 0.01% in vehicle** | 400 μL topical | 26 days |
| 3 | 21-30 | Vehicle** | N/A | 400 μL topical | 26 days |

*T3 is 3,5,3'-triiodothyronine.

**The vehicle is 60% ethanol, 20% propylene glycol, and 20% dimethyl isosorbide (commercially available from Sigma Chemical Co., St. Louis, MO).

The mice are treated topically Monday through Friday on their lower back (base of tail to the lower rib). A pipettor and tip are used to deliver 400 μL to each mouse's back. The 400 μL application is applied slowly while moving hair on the mouse to allow the application to reach the skin.

While each treatment is being applied to the mouse topically, a visual grade of from 0 to 4 will be given to the skin color in the application area of each animal. As a mouse converts from telogen to anagen, its skin color will become more bluish-black. As indicated in Table 4, the grades 0 to 4 represent the following visual observations as the skin progresses from white to bluish-black.

TABLE 4

Evaluation Criteria

| Visual Observation | Grade |
|---|---|
| Whitish Skin Color | 0 |
| Skin is light gray (indication of initiation of anagen) | 1 |
| Appearance of Blue Spots | 2 |
| Blue Spots are aggregating to form one large blue area | 3 |
| Skin is dark blue (almost black) with color covering majority of treatment area (indication of mouse in full anagen) | 4 |

Example 1

13,14-dihydro-15-(2-benzathiozolyl)pentanor Prostaglandin $F_{1\alpha}$, having the structure

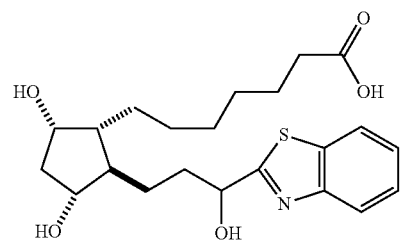 [SMILES: O=C(O)CCCCCC[C@@H]1[C@@H](CCC(O)c2nc3ccccc3s2)[C@H](O)C[C@@H]1O]

was tested according to the method Reference Example 1. 13,14-dihydro-15-(2-benzathiozolyl)pentanor Prostaglandin $F_{1\alpha}$ grew hair and had $IC_{50}$ of 45 nM.

Comparative Example 1

Latanoprost, having the structure:

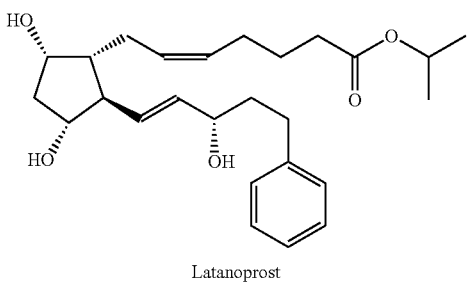 [SMILES: CC(C)OC(=O)CCC/C=C\C[C@@H]1[C@@H](/C=C/[C@@H](O)CCc2ccccc2)[C@H](O)C[C@@H]1O]

Latanoprost was tested according to the method Reference Example 1. Latanoprost was active at 0.01% and 0.1%. Grades representing the average animal score on day 26 are reported in Table 5.

However, latanoprost is nonselective. Although latanoprost does not negate the effect of activating the FP receptor, latanoprost also activates the $EP_1$ receptor, which which results in the side effect of causing pain.

Example 2

Fluprostenol Methyl Ester having the structure:

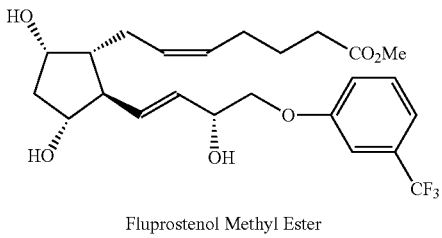 [SMILES: COC(=O)CCC/C=C\C[C@@H]1[C@@H](/C=C/[C@@H](O)COc2cccc(C(F)(F)F)c2)[C@H](O)C[C@@H]1O]

Fluprostenol Methyl Ester was tested according to the method Reference Example 1. Fluprostenol grew hair at 0.01% and 0.1%. Grades representing the average animal score on day 26 are reported in Table 5.

TABLE 5

| | | Grades | |
|---|---|---|---|
| Example | PGF | 0.01% | 0.1% |
| Comparative Example 1 | latanaprost | 0.71 | 2.9 |
| Example 2 | fluprostenol methyl ester | 3.9 | 2.6 |

Comparative Example 2

A composition containing 0.01% of a T3 compound was prepared and tested according to the method of Reference Example 1. The T3 compound grew hair.

Example 3

Compositions for topical administration are made, comprising:

| Component | 3-1 | 3-2 | 3-3 |
|---|---|---|---|
| PGF (wt %) | 0.019 | 0.027 | 0.045 |
| $IC_{50}$ the PGF (nM) | 19 | 27 | 45 |
| Ethanol (wt %) | 59.988 | 59.983 | 59.973 |
| Propylene Glycol (wt %) | 19.996 | 19.995 | 19.991 |
| Dimethyl Isosorbide (wt %) | 19.996 | 19.995 | 19.991 |

The PGFs in the compositions are as follows:

| Sample | PGF |
|---|---|
| 3-1 | (structure with fluorophenyl alkyne) |
| 3-2 | (structure with benzothiophene) |
| 3-3 | (structure with benzothiazole) |

A human male subject suffering from male pattern baldness is treated by a method of this invention. Specifically, for 6 weeks, one of the above compositions is daily administered topically to the subject to induce hair growth.

Example 4

A composition for topical administration is made according to the method of Dowton et al., "Influence of Liposomal Composition on Topical Delivery of Encapsulated Cyclosporin A: I. An in vitro Study Using Hairless Mouse Skin", *S.T.P. Pharma Sciences*, Vol. 3, pp. 404-407 (1993), using a PGF in lieu of cyclosporin A and using the NOVA-SOME® 1 (available from Micro-Pak, Inc. of Wilmington, Del.) for the non-ionic liposomal formulation.

A human male subject suffering from male pattern baldness is treated each day with the above composition. Specifically, for 6 weeks, the above composition is administered topically to the subject.

Example 5

Shampoos are made, comprising:

| Component | Ex. 5-1 | Ex. 5-2 | Ex. 5-3 | Ex. 5-4 |
|---|---|---|---|---|
| Ammonium Lauryl Sulfate | 11.5% | 11.5% | 9.5% | 7.5% |
| Ammonium Laureth Sulfate | 4% | 3% | 2% | 2% |
| Cocamide MEA | 2% | 2% | 2% | 2% |
| Ethylene Glycol Distearate | 2% | 2% | 2% | 2% |
| Cetyl Alcohol | 2% | 2% | 2% | 2% |
| Stearyl Alcohol | 1.2% | 1.2% | 1.2% | 1.2% |
| Glycerin | 1% | 1% | 1% | 1% |
| Polyquaternium 10 | 0.5% | 0.25% | — | — |
| Polyquaternium 24 | — | — | 0.5% | 0.25% |
| Sodium Chloride | 0.1% | 0.1% | 0.1% | 0.1% |
| Sucrose Polyesters of Cottonate Fatty Acid | 3% | 3% | — | — |
| Sucrose Polyesters of Behenate Fatty Acid | 2% | 3% | — | — |
| Polydimethyl Siloxane | — | — | 3% | 2% |
| Cocaminopropyl Betaine | — | 1% | 3% | 3% |
| Lauryl Dimethyl Amine Oxide | 1.5% | 1.5% | 1.5% | 1.5% |
| Decyl Polyglucose | — | — | 1% | 1% |
| DMDM Hydantoin | 0.15% | 0.15% | 0.15% | 0.15% |
| PGF having $IC_{50}$ of 19 nM | — | 0.019% | 0.019% | — |
| PGF having $IC_{50}$ of 45 nM | 0.045% | — | — | 0.045% |
| Minoxidil | — | — | 3% | 2% |
| Phenoxyethanol | 0.5% | 0.5% | 0.5% | 0.5% |
| Fragrance | 0.5% | 0.5% | 0.5% | 0.5% |
| Water | q.s. | q.s. | q.s. | q.s. |

The PGF having $IC_{50}$ of 19 nM is the same as that in Example 3-1.
The PGF having $IC_{50}$ of 45 nM is the same as that in Example 3-3.

A human subject suffering from male pattern baldness is treated by a method of this invention. Specifically, for 12 weeks, a shampoo described above is used daily by the subject.

Example 6

A mascara composition is prepared. The composition comprises:

| Component | % W/W |
|---|---|
| WATER, DEIONIZED, USP | q.s |
| BLACK 1080 MICRONIZED TYPE | 10.000 |
| GLYCERYL MONOSTEARATE (2400 TYPE) | 8.500 |
| C18-36 ACID TRIGLYCERIDE | 5.500 |
| STEARIC ACID, TRIPLE PRESSED, LIQUID | 4.000 |
| ETHYL ALCOHOL SD 40-B, 190 PROOF/SERIAL #: | 4.000 |
| BEESWAX WHITE, FLAKES | 3.250 |
| SHELLAC, NF | 3.000 |
| LECITHIN, GRANULAR (TYPE 6450) | 2.500 |
| TRIETHANOLAMINE 99% - TANK | 2.470 |
| PARAFFIN WAX | 2.250 |
| PARAFFIN WAX 118/125 | 2.250 |
| CARNAUBA WAX, NF | 2.000 |
| POTASSIUM CETYL PHOSPHATE | 1.000 |
| PHENOXYETHANOL | 0.800 |
| OLEIC ACID NF | 0.750 |
| DL-PANTHENOL | 0.350 |
| PVP/VA COPOLYMER | 0.250 |
| METHYLPARABEN, NF | 0.200 |
| DIAZOLIDINYL UREA | 0.200 |
| SIMETHICONE | 0.200 |
| ETHYLPARABEN NF | 0.150 |
| PENTAERYTHRITYL HYDROGENATED ROSINATE | 0.150 |
| PROPYLPARABEN, NF | 0.100 |
| TRISODIUM EDTA | 0.100 |
| PGF having $IC_{50}$ of 19 nM | 0.019 |

The PGF is the same as that used in Example 3-1.
A human female subject applies the composition each day. Specifically, for 6 weeks, the above composition is administered topically to the subject to darken and thicken eyelashes.

Example 7

Pharmaceutical compositions in the form of tablets are prepared by conventional methods, such as mixing and direct compaction, formulated as follows:

| Ingredient | Quantity (mg per tablet) |
|---|---|
| PGF | 0.5 |
| Microcrystalline Cellulose | 100 |
| Sodium Starch Glycollate | 30 |
| Magnesium Stearate | 3 |

The PGF is the same as that used in Example 3-3.
The above composition is administered orally to a subject once daily for 6 to 12 weeks to promote hair growth.

Example 8

Pharmaceutical compositions in liquid form are prepared by conventional methods, formulated as follows:

| Ingredient | Quantity |
|---|---|
| PGF | 0.1 mg |
| Phosphate buffered physiological saline | 10 ml |
| Methyl Paraben | 0.05 ml |

The PGF is the same as that used in Example 3-3.
1.0 ml of the above composition is administered subcutaneously once daily at the site of hair loss for 6 to 12 weeks to promote hair growth.

Example 9

A topical pharmaceutical composition is prepared by conventional methods and formulated as follows:

| Ingredient | Amount (wt %) |
|---|---|
| PGF | 0.004 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCL and/or NaOH | pH 7.2-7.5 |
| Purified water | q.s. to 100% |

The PGF is the same as that used in Example 3-3.

The above composition is administered ocularly to a subject once per day for 6 to 12 weeks to promote eyelash growth.

EFFECTS OF THE INVENTION

The compositions and methods herein provide a cosmetic benefit with respect to hair growth and appearance in subjects desiring such treatment.

What is claimed is:

1. A method of growing hair, wherein the method comprises topically applying to mammalian skin a safe and effective amount of a composition comprising:
   A) an active ingredient selected from the group consisting of a prostaglandin F analog of the following structure:

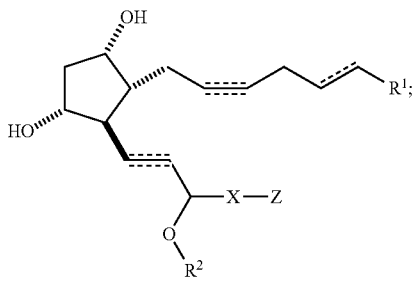

and pharmaceutically acceptable salts thereof;
   wherein $R^1$ is selected from the group consisting of C(O)NHOH, $CH_2OH$, $S(O)_2R^3$, $C(O)NHR^3$, $C(O)NHS(O)_2R^4$, and tetrazole;
   $R^2$ is selected from the group consisting of a hydrogen atom, a lower heterogeneous group, and a lower monovalent hydrocarbon group;
   $R^3$ is selected from the group consisting of a monovalent hydrocarbon group, a heterogeneous group, a carbocyclic group, a heterocyclic group, an aromatic group, a heteroaromatic group, a substituted monovalent hydrocarbon group, a substituted heterogeneous group, a substituted carbocyclic group, a substituted heterocyclic group, a substituted aromatic group, and a substituted heteroaromatic group;
   $R^4$ is selected from the group consisting of a monovalent hydrocarbon group, a heterogeneous group, a carbocyclic group, a heterocyclic group, an aromatic group, a heteroaromatic group, a substituted monovalent hydrocarbon group, a substituted heterogeneous group, a substituted carbocyclic group, a substituted heterocyclic group, a substituted aromatic group, and a substituted heteroaromatic group;
   X is selected from the group consisting of —CC—, a covalent bond, —CH=C=CH—, —CH=CH—, —CH=N—, —C(O)—, —C(O)Y—, —(CH$_2$)$_n$—, wherein n is 2 to 4, —CH$_2$NH—, —CH$_2$S—, and —CH$_2$O—;
   Y is selected from the group consisting of a sulfur atom, an oxygen atom, and NH; and
   Z is selected from the group consisting of a carbocyclic group, a heterocyclic group, an aromatic group, a heteroaromatic group, a substituted carbocyclic group, a substituted heterocyclic group, a substituted aromatic group, and a substituted heteroaromatic group.

2. The method of claim 1, wherein $R^1$ is selected from the group consisting of C(O)NHOH, C(O)NHR$^3$, and C(O)NHS(O)$_2$R$^4$, and tetrazole.

3. The method of claim 1, wherein $R^2$ is a hydrogen atom.

4. The method of claim 1, wherein $R^3$ is selected from the group consisting of methyl, ethyl, and isopropyl.

5. The method of claim 1, wherein Z is an aromatic ring.

6. The method of claim 1, wherein the composition is a topical composition in a form selected from the group consisting of solutions, oils, creams, ointments, gels, lotions, shampoos, leave-on and rinse-out hair conditioners, milks, cleansers, moisturizers, sprays, and skin patches.

7. The method of claim 1, wherein the composition is a topical composition further comprising B) a carrier, wherein the carrier is selected from the group consisting of water, alcohols, aloe vera gel, allantoin, glycerin, vitamin A and E oils, mineral oil, propylene glycol, dimethyl isosorbide, polypropylene glycol, 2 myristyl propionate, and combinations thereof.

8. The method of claim 1, wherein the composition further comprises C) an activity enhancer selected from the group consisting of i) a hair growth stimulant, ii) a penetration enhancer, and combinations thereof.

9. The method of claim 8, wherein component i) is selected from the group vasodilator, an antiandrogen, a cyclosporin, a cyclosporin analog, an antimicrobial, an anti-inflammatory, a thyroid hormone, a thyroid hormone derivative, and a thyroid hormone analog, a non-selective prostaglandin agonist, a non-selective prostaglandin antagonist, a retinoid, a triterpene, and combinations thereof.

10. The method of claim 8, wherein component ii) is selected from the group consisting of 2-methyl propan-2-ol, propan-2-ol, ethyl-2-hydroxypropanoate, hexan-2,5-diol, polyoxyethylene(2) ethyl ether, di(2-hydroxypropyl) ether, pentan-2,4-diol, acetone, polyoxyethylene(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, polyoxyethylene ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, isopropyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hydroxyoctanoic acid, dimethyl sulphoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one, and combinations thereof.

11. The method of claim 1, wherein the composition is a topical composition locally administered on the skin once per day.

12. The method of claim 11, wherein the composition is administered once per day for 6 to 12 weeks.

13. The method of claim 1, wherein the composition is topically applied directly to the locus of desired hair growth.

14. The method of claim 1, wherein the prostaglandin F analog is selective for an FP receptor over an excitatory prostaglandin receptor in a ratio of at least 1:10.

15. The method of claim 1, wherein the prostaglandin F analog is selective for an FP receptor over an excitatory prostaglandin receptor in a ratio of at least 1:20.

16. The method of claim 1, wherein the prostaglandin F analog is selective for an FP receptor over an excitatory prostaglandin receptor in a ratio of at least 1:50.

17. A method of growing hair, wherein the method comprises topically applying to mammalian skin a safe and effective amount of a composition comprising:
  A) an active ingredient selected from the group consisting of a prostaglandin F analog of the following structure:

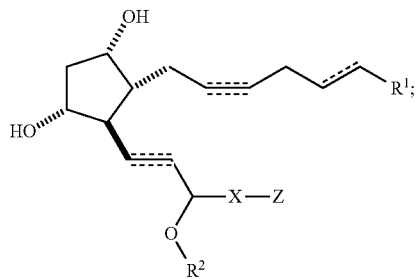

and pharmaceutically acceptable salts thereof;
   wherein $R^1$ is selected from the group consisting of C(O)NHOH, C(O)NHR$^3$, C(O)NHS(O)$_2$R$^4$ and tetrazole;
   $R^2$ is a hydrogen atom;
   $R^3$ is methyl, ethyl or isopropyl;
   $R^4$ is phenyl;
   X is selected from the group consisting of —C≡C—, a covalent bond, —CH=C=CH—, —CH=CH—, —CH=N—, —C(O)—, —C(O)Y—, and —(CH$_2$)$_n$—, wherein n is 2 to 4;
   Y is selected from the group consisting of a sulfur atom, an oxygen atom, and NH; and
   Z is selected from the group consisting of a carbocyclic group, a heterocyclic group, an aromatic group, a heteroaromatic group, a substituted carbocyclic group, a substituted heterocyclic group, a substituted aromatic group, and a substituted heteroaromatic group.

18. The method of claim 17, wherein Z is an aromatic ring.

19. The method of claim 17, wherein the composition is a topical composition in a form selected from the group consisting of solutions, oils, creams, ointments, gels, lotions, shampoos, leave-on and rinse-out hair conditioners, milks, cleansers, moisturizers, sprays, and skin patches.

20. The method of claim 17, wherein the composition is a topical composition further comprising B) a carrier, wherein the carrier is selected from the group consisting of water, alcohols, aloe vera gel, allantoin, glycerin, vitamin A and E oils, mineral oil, propylene glycol, dimethyl isosorbide, polypropylene glycol, 2 myristyl propionate, and combinations thereof.

21. The method of claim 17, wherein the composition further comprises C) an activity enhancer selected from the group consisting of i) a hair growth stimulant, ii) a penetration enhancer, and combinations thereof.

22. The method of claim 21, wherein component i) is selected from the group vasodilator, an antiandrogen, a cyclosporin, a cyclosporin analog, an antimicrobial, an anti-inflammatory, a thyroid hormone, a thyroid hormone derivative, and a thyroid hormone analog, a non-selective prostaglandin agonist, a non-selective prostaglandin antagonist, a retinoid, a triterpene, and combinations thereof.

23. The method of claim 21, wherein component ii) is selected from the group consisting of 2-methyl propan-2-ol, propan-2-ol, ethyl-2-hydroxypropanoate, hexan-2,5-diol, polyoxyethylene(2) ethyl ether, di(2-hydroxypropyl) ether, pentan-2,4-diol, acetone, polyoxyethylene(2) methyl ether, 2-hydroxypropionic acid, 2-hydroxyoctanoic acid, propan-1-ol, 1,4-dioxane, tetrahydrofuran, butan-1,4-diol, propylene glycol dipelargonate, polyoxypropylene 15 stearyl ether, octyl alcohol, polyoxyethylene ester of oleyl alcohol, oleyl alcohol, lauryl alcohol, dioctyl adipate, dicapryl adipate, di-isopropyl adipate, di-isopropyl sebacate, dibutyl sebacate, diethyl sebacate, dimethyl sebacate, dioctyl sebacate, dibutyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, isopropyl isostearate, butyl laurate, benzyl benzoate, butyl benzoate, hexyl laurate, ethyl caprate, ethyl caprylate, butyl stearate, benzyl salicylate, 2-hydroxypropanoic acid, 2-hydroxyoctanoic acid, dimethyl sulphoxide, N,N-dimethyl acetamide, N,N-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one, and combinations thereof.

24. The method of claim 17, wherein the composition is a topical composition locally administered on the skin once per day.

25. The method of claim 24, wherein the composition is administered once per day for 6 to 12 weeks.

26. The method of claim 17, wherein the composition is topically applied directly to the locus of desired hair growth.

27. The method of claim 17, wherein the prostaglandin F analog is selective for an FP receptor over an excitatory prostaglandin receptor in a ratio of at least 1:10.

28. The method of claim 17, wherein the prostaglandin F analog is selective for an FP receptor over an excitatory prostaglandin receptor in a ratio of at least 1:20.

29. The method of claim 17, wherein the prostaglandin F analog is selective for an FP receptor over an excitatory prostaglandin receptor in a ratio of at least 1:50.

\* \* \* \* \*